(12) United States Patent
Castro et al.

(10) Patent No.: US 11,607,404 B2
(45) Date of Patent: Mar. 21, 2023

(54) COMBINATIONS OF RAD51 AND PARP INHIBITORS

(71) Applicant: Cyteir Therapeutics, Inc., Lexington, MA (US)

(72) Inventors: Alfredo C. Castro, Woburn, MA (US); Melinda Day, Sudbury, MA (US); Tyler Maclay, Somerville, MA (US); Casey Cameron McComas, Phoenixville, PA (US); Kevin Mills, Acton, MA (US); Joseph Vacca, Telford, PA (US)

(73) Assignee: Cyteir Therapeutics, Inc., Lexington, MA (US)

( * ) Notice: Subject to any disclaimer, the term of this patent is extended or adjusted under 35 U.S.C. 154(b) by 16 days.

(21) Appl. No.: 16/829,099

(22) Filed: Mar. 25, 2020

(65) Prior Publication Data
US 2020/0306229 A1 Oct. 1, 2020

Related U.S. Application Data

(60) Provisional application No. 62/823,556, filed on Mar. 25, 2019.

(51) Int. Cl.
*A61K 31/426* (2006.01)
*A61K 31/502* (2006.01)

(52) U.S. Cl.
CPC .......... *A61K 31/426* (2013.01); *A61K 31/502* (2013.01)

(58) Field of Classification Search
CPC .............................. A61K 31/426; A61K 31/502
See application file for complete search history.

(56) References Cited

U.S. PATENT DOCUMENTS

| | | | |
|---|---|---|---|
| 4,522,811 A | 6/1985 | Eppstein et al. | |
| 5,837,832 A | 11/1998 | Chee et al. | |
| 8,551,984 B2 | 10/2013 | Altman et al. | |
| 10,336,746 B1 * | 7/2019 | Castro | C07D 417/14 |
| 10,590,122 B2 * | 3/2020 | Castro | C07D 277/42 |
| 11,084,812 B2 * | 8/2021 | Castro | C07D 417/04 |
| 2019/0077799 A1 | 3/2019 | Castro et al. | |
| 2020/0129484 A1 | 4/2020 | Castro et al. | |
| 2020/0291014 A1 | 9/2020 | Lapierre et al. | |
| 2020/0397760 A1 | 12/2020 | Castro et al. | |
| 2022/0056022 A1 | 2/2022 | Castro et al. | |

FOREIGN PATENT DOCUMENTS

| | | |
|---|---|---|
| EP | 0834575 | 11/2001 |
| EP | 0834576 | 1/2002 |
| WO | WO 96/31622 A1 | 10/1996 |
| WO | WO 97/10365 A1 | 3/1997 |
| WO | WO 98/30883 A2 | 7/1998 |
| WO | WO 2016/094897 A1 | 6/2016 |

OTHER PUBLICATIONS

Borchert, G.M. et al. (2011) "Repression of human activation induced cytidine deaminase by miR-93 and miR-155" *BMC Cancer*, 11:347, 9 pages.
Brown, J.S. et al. (2016) "PARP inhibitors: the race is on" *British J Cancer*, 114(7):713-715.
Chaudhuri, J. et al. (2004) "Class-Switch Recombination: Interplay of Transcription, DNA Deamination and DNA Repair" *Nature Reviews, Immunology*, 4:541-552.
Chaudhuri, J. et al. (2007) "Evolution of the Immunoglobulin Heavy Chain Class Switch Recombination Mechanism" *Advances in Immunology*, 94:157-214.
Chaudhuri, J. et al. (2004) "Replication protein A interacts with AID to promote deamination of somatic hypermutation targets" *Nature*, 430:992-998.
Crouch, E.E. et al. (2007) "Regulation of AID expression in the immune response" *The Journal of Experimental Medicine*, 204(5):1145-1156.
Engels, K. et al. (2008) "Expression of Activation-induced Cytidine Deaminase in Malignant Lymphomas Infiltrating the Bone Marrow" *Appl Immunohistochem Mol Morphol*, 16(6):521-529.
Feldhahn, N. et al. (2007) "Activation-induced cytidine deaminase acts as a mutator in BCR-ABL1—transformed acute lymphoblastic leukemia cells" *J Exp Med*, 204:1157-1166.
Greeve, J. et al. (2003) "Expression of activation-induced cytidine deaminase in human B-cell non-Hodgkin lymphomas" *Blood*, 101(9):3574-3580.
Gruber, T.A. et al. (2010) "Activation-Induced Cytidine Deaminase Accelerates Clonal Evolution in BCR-ABL1—Driven B-Cell Lineage Acute Lymphoblastic Leukemia" *Cancer Res*, 70:7411-7420.
Hancer, V.S. et al. (2011) "Activation-induced cytidine deaminase mRNA levels in chronic lymphocytic leukemia" *Leuk Lymphoma*, 52(1):79-84.
Hardianti, M.S. et al. (2004) "Activation-induced cytidine deaminase expression in follicular lymphoma: association between AID expression and ongoing mutation in FL" *Leukemia* 18:826-831.

(Continued)

*Primary Examiner* — Golam M Shameem
(74) *Attorney, Agent, or Firm* — Cooley LLP; Matthew Pavao; Chen Chen

(57) ABSTRACT

This application is directed to inhibitors of RAD51 represented by the following structural formula:

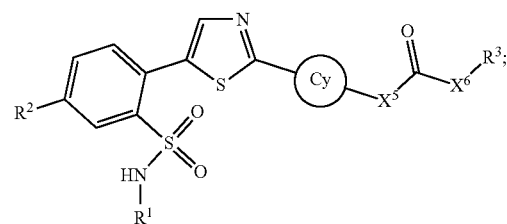

in combination with a PARP inhibitor, and methods for their use, such as to treat cancer, autoimmune diseases, immune deficiencies, or neurodegenerative diseases.

12 Claims, 17 Drawing Sheets

(56) References Cited

OTHER PUBLICATIONS

Heintel, D. et al. (2004) "High expression of activation-induced cytidine deaminase (AID) mRNA is associated with unmutated $IGV_H$ gene status and unfavourable cytogenetic aberrations in patients with chronic lymphocytic leukaemia" *Leukemia*, 18:756-762.
Hockley, S. L. et al. (2010) "Higher expression levels of activation-induced cytidine deaminase distinguish hairy cell leukemia from hairy cell leukemia-variant and splenic marginal zone lymphoma" *Leukemia*, 24:1084-1086.
Houllenberghs, H. et al. (2017) "Suspected Lynch syndrome associated MSH6 variants: A functional assay to determine their pathogenicity" *PLOS Genetics*, 13(5):e1006765, 18 pages.
Klemm, L. et al. (2009) "The B Cell Mutator AID Promotes B Lymphoid Blast Crisis and Drug Resistance in Chronic Myeloid Leukemia" *Cancer Cell*, 16:232-245.
Komori, J. et al. (2008) "Activation-Induced Cytidine Deaminase Links Bile Duct Inflammation to Human Cholangiocarcinoma" *Hepatology*, 47(3):888-896.
Kotani, A. et al. (2007) "Activation-induced cytidine deaminase (AID) promotes B cell lymphomagenesis in Emu-cmyc transgenic mice" *PNAS*, 104(5):1616-1620.
Kovalchuk, A.L. et al. (2007) "AID-deficient Bcl-xL transgenic mice develop delayed atypical plasma cell tumors with unusual Ig/Myc chromosomal rearrangements" *J Exp Med*, 204(12):2989-3001.
Kumari, S. et al. (2008) "DNA Damage: Detection Strategies" *EXCLI Journal*, 7:44-62.
Küppers, R. et al. (2001) "Mechanisms of chromosomal translocations inB cell lymphomas" *Oncogene*, 20:5580-5594.
Leuenberger, M. et al. (2010) "AID protein expression in chronic lymphocytic leukemia/small lymphocytic lymphoma is associated with poor prognosis and complex genetic alterations" *Modern Pathology*, 23:177-186.
Liu, M. et al. (2009) "Balancing AID and DNA repair during somatic hypermutation" *Trends in Immunology*, 30(4):173-181.
Liu, M. et al. (2008) "Two levels of protection for the B cell genome during somatic hypermutation" *Nature*, 451:841-845, including "Methods", 1 page.
Longerich, S. et al. (2006) "AID in somatic hypermutation and class switch recombination" *Curr Opin Immunol*, 18:164-176.
Manis, J.P. et al. (2002) "Mechanism and control of class-switch recombination" *Trends Immunol*, 23(1):31-39.
Mao, X. et al. (2001) "A case of adult T-cell leukaemia/lymphoma characterized by multiplex-fluorescence in situ hybridization, comparative genomic hybridization, fluorescence in situ hybridization and cytogenetics" *Br J Dermatol*, 145:117-122.
Marusawa, H. (2008) "Aberrant AID expression and human cancer development" *Int J Biochem Cell Biol*, 40:1399-1402.
Marusawa, H. et al. (2011) "Role of Activation-Induced Cytidine Deaminase in Inflammation-Associated Cancer Development" *Advances in Immunology*, 111:109-141.
Mills, K.D. et al. (2003) "The role of DNA breaks in genomic instability and tumorigenesis" *Immunological Reviews*, 194:77-95.
Motalleb, G. et al. (2012) "Methods for DNA Strand Breaks Detection" *Research Journal of Applied Sciences, Engineering and Technology*, 4(13):1888-1894.
Muramatsu, M. et al. (1999) "Specific Expression of Activation-induced Cytidine Deaminase (AID), a Novel Member of the RNA-editing Deaminase Family in Germinal Center B Cells" *The Journal of Biological Chemistry*, 274(26):18470-18476.
Muto, T. et al. (2006) "Negative regulation of activation-induced cytidine deaminase in B cells" *PNAS*, 103(8):2752-2757.
Nakamura, M. et al. (2011) "High levels of activation-induced cytidine deaminase expression in adult T-cell leukaemia/lymphoma" *Br J Dermatol*, 165(2):437-439.
NCBI Gene ID: 10930 (Aug. 18, 2020) "APOBEC2 apolipoprotein B mRNA editing enzyme catalytic subunit 2 [ *Homo sapiens* (human) ]" National Center for Biotechnology Information, U.S. National Library of Medicine [online]. Retrieved from: https://www.ncbi.nlm.nih.gov/gene/?term=10930, 6 printed pages.
NCBI Gene ID: 140564 (Aug. 18, 2020) "APOBEC3D apolipoprotein B mRNA editing enzyme catalytic subunit 3D [ *Homo sapiens* (human) ]" National Center for Biotechnology Information, U.S. National Library of Medicine [online]. Retrieved from: https://www.ncbi.nlm.nih.gov/gene/?term=140564, 10 printed pages.
NCBI Gene ID: 164668 (Aug. 18, 2020) "APOBEC3H apolipoprotein B mRNA editing enzyme catalytic subunit 3H [ *Homo sapiens* (human) ]" National Center for Biotechnology Information, U.S. National Library of Medicine [online]. Retrieved from: https://www.ncbi.nlm.nih.gov/gene/?term=164668, 8 printed pages.
NCBI Gene ID: 200315 (Aug. 30, 2020) "APOBEC3A apolipoprotein B mRNA editing enzyme catalytic subunit 3A [ *Homo sapiens* (human) ]" National Center for Biotechnology Information, U.S. National Library of Medicine [online]. Retrieved from: https://www.ncbi.nlm.nih.gov/gene/?term=200315, 10 printed pages.
NCBI Gene ID: 200316 (Aug. 18, 2020) "APOBEC3F apolipoprotein B mRNA editing enzyme catalytic subunit 3F [ *Homo sapiens* (human) ]" National Center for Biotechnology Information, U.S. National Library of Medicine [online]. Retrieved from: https://www.ncbi.nlm.nih.gov/gene/?term=200316, 7 printed pages.
NCBI Gene ID: 23626 (Aug. 18, 2020) "SPO11 initiator of meiotic double standard breaks [*Homo sapiens* (human)]" National Center for Biotechnology Information, U.S. National Library of Medicine [online], Retrieved from: https://www.ncbi.nlm.nih.gov/gene?cmd=Retrieve&dopt=full_report&list_uids=23626; 11 printed pages.
NCBI Gene ID: 27350 (Aug. 22, 2020) "APOBEC3C apolipoprotein B mRNA editing enzyme catalytic subunit 3C [ *Homo sapiens* (human) ]" National Center for Biotechnology Information, U.S. National Library of Medicine [online]. Retrieved from: https://www.ncbi.nlm.nih.gov/gene/?term=27350, 6 printed pages.
NCBI Gene ID: 339 (Aug. 18, 2020) "APOBEC1 apolipoprotein B mRNA editing enzyme catalytic subunit 1 [*Homo sapiens* (human)]" National Center for Biotechnology Information, U.S. National Library of Medicine [online]. Retrieved from: https://www.ncbi.nlm.nih.gov/gene/?term=339; retrieved on Aug. 31, 2020, 9 printed pages.
NCBI Gene ID: 403314 (Aug. 22, 2020) "APOBEC4 apolipoprotein B mRNA editing enzyme catalytic polypeptide like 4 [ *Homo sapiens* (human) ]" National Center for Biotechnology Information, U.S. National Library of Medicine [online]. Retrieved from: https://www.ncbi.nlm.nih.gov/gene/?term=403314, 7 printed pages.
NCBI Gene ID: 57379 (Aug. 23, 2020) "AICDA activation induced cytidine deaminase [*Homo sapiens* (human)]" National Center for Biotechnology Information, U.S. National Library of Medicine [online], Retrieved from: https://www.ncbi.nlm.nih.gov/gene/57379; retrieved on Sep. 1, 2020, 12 printed pages.
NCBI Gene ID: 5896 (Aug. 22, 2020) "RAG1 recombination activating 1 [*Homo sapiens* (human)]" National Center for Biotechnology Information, U.S. National Library of Medicine [online]. Retrieved from: https://www.ncbi.nlm.nih.gov/gene/5896; 7 printed pages.
NCBI Gene ID: 5897 (Aug. 22, 2020) "RAG2 recombination activating 2 [*Homo sapiens* (human)]" National Center for Biotechnology Information, U.S. National Library of Medicine [online]. Retrieved from: https://www.ncbi.nlm.nih.gov/gene/?term=5897; 6 printed pages.
NCBI Gene ID: 60489 (Aug. 22, 2020) "APOBEC3G apolipoprotein B mRNA editing enzyme catalytic subunit 3G [ *Homo sapiens* (human) ]" National Center for Biotechnology Information, U.S. National Library of Medicine [online]. Retrieved from: https://www.ncbi.nlm.nih.gov/gene/?term=60489, 8 printed pages.
NCBI Gene ID: 7150 (Aug. 30, 2020) "TOP1 DNA topoisomerase I [ *Homo sapiens* (human) ]" National Center for Biotechnology Information, U.S. National Library of Medicine [online]. Retrieved from: https://www.ncbi.nlm.nih.gov/gene/?term=7150, 7 printed pages.
NCBI Gene ID: 7153 (Aug. 18, 2020) "TOP2A DNA topoisomerase II alpha [ *Homo sapiens* (human) ]" National Center for Biotechnology Information, U.S. National Library of Medicine [online]. Retrieved from: https://www.ncbi.nlm.nih.gov/gene/?term=7153, 8 printed pages.

(56) References Cited

OTHER PUBLICATIONS

NCBI Gene ID: 7155 (Aug. 18, 2020) "TOP2B DNA topoisomerase II beta [ *Homo sapiens* (human) ]" National Center for Biotechnology Information, U.S. National Library of Medicine [online]. Retrieved from: https://www.ncbi.nlm.nih.gov/gene/?term=7155, 11 printed pages.

Okazaki, I. (2003) "Constitutive Expression of AID Leads to Tumorigenesis" *The Journal of Experimental Medicine*, 197(9):1173-1181.

Palacios, F. et al. (2010) "High expression of AID and active class switch recombination might account for a more aggressive disease in unmutated CLL patients: link with an activated microenvironment in CLL disease" *Blood*, 115(22):4488-4496.

Pasqualucci, L. et al. (2008) "AID is required for germinal center-derived lymphomagenesis" *Nature Genetics*, 40(1):108-112.

Pérez-Durán, P. et al. (2007) "Oncogenic events triggered by AID, the adverse effect of antibody diversification" *Carcinogenesis*, 28(12):2427-2433.

Qui, Y. et al. (2012) "Immunoglobulin G expression and its colocalization with complement proteins in papillary thyroid cancer" *Modern Pathology*, 25:36-45.

Reina-San-Martin, B. et al. (2004) "ATM Is Required for Efficient Recombination between Immunoglobulin Switch Regions" *J Exp Med*, 200(9):1103-1110.

Robbiani, D.F. (2009) "AID Produces DNA Double-Strand Breaks in Non-Ig Genes and Mature B Cell Lymphomas with Reciprocal Chromosome Translocations" *Molecular Cell*, 36:631-641.

Shen, H.M. et al. (2008) "Expression of AID transgene is regulated in activated B cells but not in resting B cells and kidney" *Molecular Immunology*, 45:1883-1892.

Shikata, H. et al. (2012) "Role of activation-induced cytidine deaminase in the progression of follicular lymphoma" *Cancer Sci*, 103(3):415-421.

Volpi, E.V. et al. (2008) "FISH glossary: an overview of the fluorescence in situ hybridization technique" *BioTechniques*, 45(4):385-409.

White, C.A. et al. (2011) "AID dysregulation in lupus-prone MRL/Fas$^{lpr/lpr}$ mice increases class switch DNA recombination and promotes interchromosomal c-Myc/IgH loci translocations: Modulation by HoxC4" *Autoimmunity*, 44(8):585-598.

Xu, X. et al. (2009) "Increased Expression of Activation-Induced Cytidine Deaminase is Associated with Anti-CCP and Rheumatoid Factor in Rheumatoid Arthritis" *Scand J Immunol*, 70:309-316.

Yoshikawa, K. et al. (2002) "AID Enzyme-Induced Hypermutation in an Actively Transcribed Gene in Fibroblasts" *Science*, 296(5575):2033-2036.

Zhang, L. et al. (2012) "Expression of immunoglobulin G in esophageal squamous cell carcinomas and its association with tumor grade and Ki67" *Human Pathology*, 43:423-434.

U.S. Appl. No. 17/552,577, filed Dec. 16, 2021, Lapierre et al.

\* cited by examiner

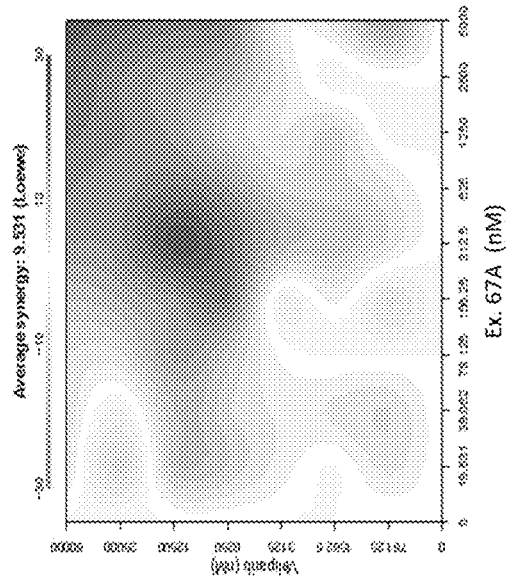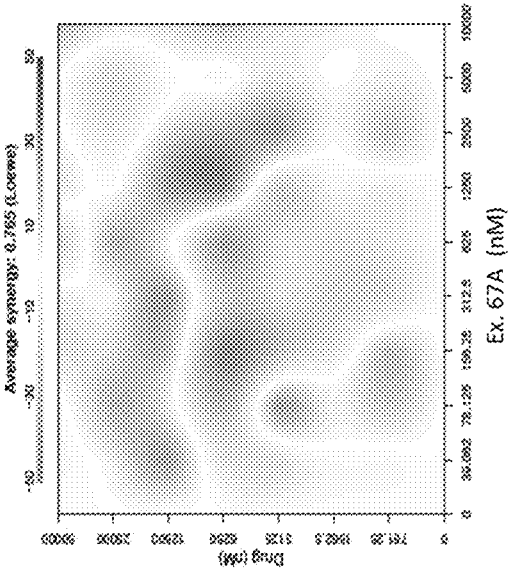
FIG. 5C
FIG. 5D
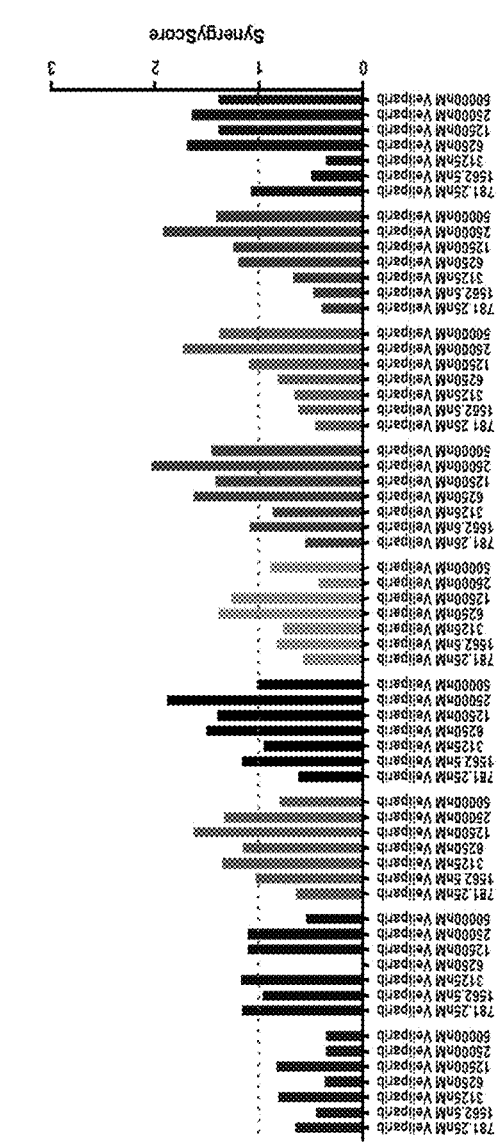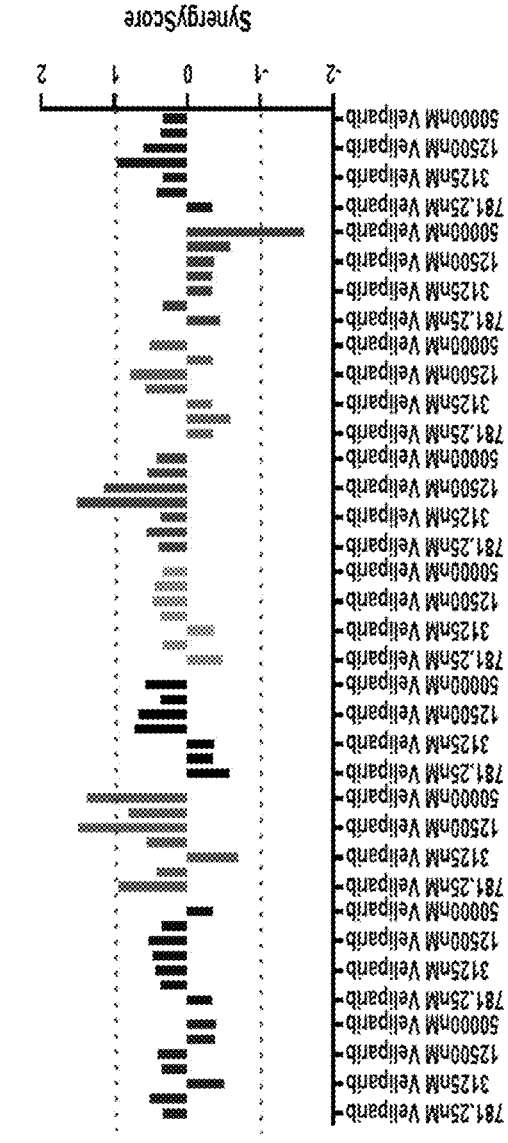

COMBINATIONS OF RAD51 AND PARP INHIBITORS

RELATED APPLICATIONS

This application claims priority to and the benefit of U.S. Provisional Application No. 62/823,556, filed on Mar. 25, 2019, the entire contents of which are incorporated herein by reference.

BACKGROUND

RAD51 is a member of the RAD51 family which promotes the repair of DNA double strand breaks (DSB). RAD51 protein is highly conserved in most eukaryotes, from yeast to humans. The human RAD51 is a 339-amino acid protein that plays a major role in DNA replication and repair by homologous recombination (HR). RAD51 catalyzes strand transfer between a broken sequence and undamaged homologous template to allow re-synthesis of the damaged region.

Studies have demonstrated sensitization to certain DNA damaging therapies associated with defects in proteins that promote HR DNA repair. This sensitization is particularly dramatic for DNA cross-linking chemotherapeutic drugs and ionizing radiation. It has been shown that HR can be partially inhibited in order to sensitize cells to DNA damaging therapies. For example, inhibition of XRCC3 (a RAD51 paralog protein) using a synthetic peptide sensitized Chinese Hamster Ovary (CHO) cells to cisplatin and inhibited the formation of sub-nuclear RAD51 foci in response to DNA damage. Researchers have inhibited the expression of the RAD51 protein itself or blocked its function by over-expressing a dominant negative BRC peptide fragment derived from BRCA2. In view of the connection between increased sensitivity to DNA damaging therapies and defects in HR DNA repair-related proteins, there is a need for compounds that inhibit RAD51.

Poly(ADP-ribose) polymerase (PARP) constitutes a super family of eighteen proteins containing PARP catalytic domains. These proteins include PARP-1, PARP-2, PARP-3, tankyrase-1, tankyrase-2, vaultPARP and TiPARP. PARP-1, the founding member, consists of three main domains: a N-terminal DNA-binding domain containing two zinc fingers, an automodification domain, and a C-terminal catalytic domain. PARP are nuclear and cytoplasmic enzymes that cleave NAD$^+$ to nicotinamide and ADP-ribose to form long and branched ADP-ribose polymers on target proteins, including topoisomerases, histones, and PARP itself.

Poly(ADP-ribosyl)ation has been implicated in several biological processes, including DNA repair, gene transcription, cell cycle progression, cell death, chromatin functions, and genomic stability. Inhibition of PARP has been shown to play a role in several disease states PARP inhibitors have been used in prophylactic therapy for elimination of BRCA2-deficient cells, treatment of inflammation diseases, acute and chronic myocardial diseases, vascular diseases, septic shock ischemic injury, and neurotoxicity, and treatment or prevention of autoimmune diseases such as Type I diabetes and diabetic complications. PARP has also been demonstrated to play a role in the pathogenesis of hemorrhagic shock.

Thus, there is a need for therapies that utilize both RAD51 inhibitors and PARP inhibitors. The present application addresses the need.

SUMMARY

The present application discloses that inhibitors of RAD51 (see Compounds 1-75, Table 1) act synergistically in combination with PARP inhibitors. The present application provides a compound represented by Structural Formula I:

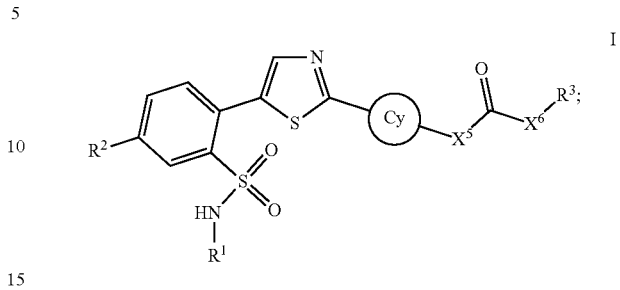

or a pharmaceutically acceptable salt thereof, for use in combination with PARP inhibitors. The definition of each variable is provided below.

The present application also provides a pharmaceutical composition comprising a compound as described herein or a pharmaceutically acceptable salt thereof and a pharmaceutically acceptable carrier or diluent.

The present application provides a method of treating a cancer, an autoimmune disease, an immune deficiency, or a neurodegenerative disease. The method comprises administering to a subject in need thereof a therapeutically effective amount of a compound disclosed herein or a pharmaceutically acceptable salt thereof or a pharmaceutical composition disclosed herein.

The present application provides the use of a compound disclosed herein, or a pharmaceutically acceptable salt thereof, or a pharmaceutical composition disclosed herein in the manufacture of a medicament for the treatment of a cancer, an autoimmune disease, an immune deficiency, or a neurodegenerative disease.

The present application provides a compound disclosed herein, or a pharmaceutically acceptable salt thereof, or a pharmaceutical composition disclosed herein for use in treating a cancer, an autoimmune disease, an immune deficiency, or a neurodegenerative disease.

The present application provides a method of treating a cancer, an autoimmune disease, an immune deficiency, or a neurodegenerative disease, wherein the method comprises administering to a subject in need thereof a therapeutically effective amount of a compound disclosed herein or a pharmaceutically acceptable salt thereof or a pharmaceutical composition disclosed herein in combination with a PARP inhibitor or a pharmaceutically acceptable salt thereof or a pharmaceutical composition comprising a PARP inhibitor.

The present application provides use of a compound disclosed herein, or a pharmaceutically acceptable salt thereof, or a pharmaceutical composition disclosed herein in combination with a PARP inhibitor, or a pharmaceutically acceptable salt thereof, or a pharmaceutical composition thereof in the manufacture of a medicament for the treatment of a cancer, an autoimmune disease, an immune deficiency, or a neurodegenerative disease.

The present application provides a compound disclosed herein, or a pharmaceutically acceptable salt thereof, or a pharmaceutical composition disclosed herein in combination with a PARP inhibitor, or a pharmaceutically acceptable salt thereof, or a pharmaceutical composition thereof for use in treating a cancer, an autoimmune disease, an immune deficiency, or a neurodegenerative disease.

The present application provides a method of treating a cancer, an autoimmune disease, an immune deficiency, or a neurodegenerative disease. The method comprises administering to a subject in need thereof a composition comprising a compound disclosed herein and a PARP inhibitor.

The present application provides a kit comprising a compound disclosed herein, or a pharmaceutically acceptable salt thereof, or a pharmaceutical composition disclosed herein, and a PARP inhibitor, or a pharmaceutically acceptable salt thereof, or a pharmaceutical composition thereof.

In some embodiments, a compound disclosed herein and the PARP inhibitor are administered in temporal proximity for treating cancer. In some embodiments, the application provides a synergistic composition of the compound disclosed herein and the PARP inhibitor, wherein the compound disclosed herein and the PARP inhibitor come into contact with each other in the human body (e.g., only in the human body).

In some embodiments, the application provides a method of preparing a composition by bringing the compound disclosed herein and the PARP inhibitor into contact with each other at a locus.

BRIEF DESCRIPTION OF THE FIGURES

The patent or application file contains at least one drawing executed in color. Copies of this patent or patent application publication with color drawing(s) will be provided by the Office upon request and payment of the necessary fee.

Bar colors represent particular concentrations of Compound # (e.g., Compound 67A). Dark purple represents 19.53125 nM, dark blue represents 39.0625 nM, brown represents 78.125 nM, black represents 156.25 nM, orange represents 312.5 nM, light purple represents 625 nM, green represents 1250 nM, red represents 2500 nM and light blue represents 5000 nM.

FIG. 5C shows veliparib—Compound 67A combination studies. Cells treated were KYSE-70 cells. Bar chart is Bliss Independence data plotted, and heatmap is according to Loewe additivity model.

FIG. 5D shows veliparib—Compound 67A combination studies. Cells treated were HCC1143 cells. Bar chart is Bliss Independence data plotted, and heatmap is according to Loewe additivity model.

DETAILED DESCRIPTION

Figure 1A:
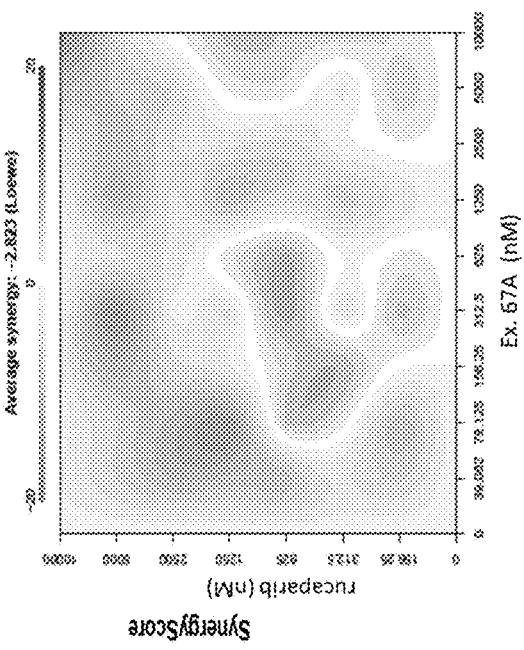
FIG. 1A shows rucaparib—Compound 67A combination studies. Cells treated were ARPE19/HPV16 cells. Bar chart is Bliss Independence data plotted, and heatmap is according to Loewe additivity model.
Figure 1A:
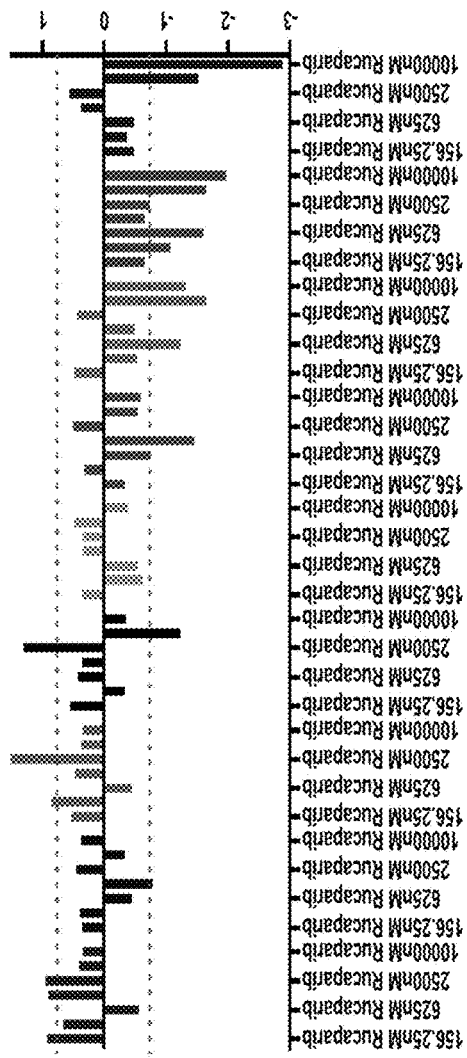
Figure 1B:
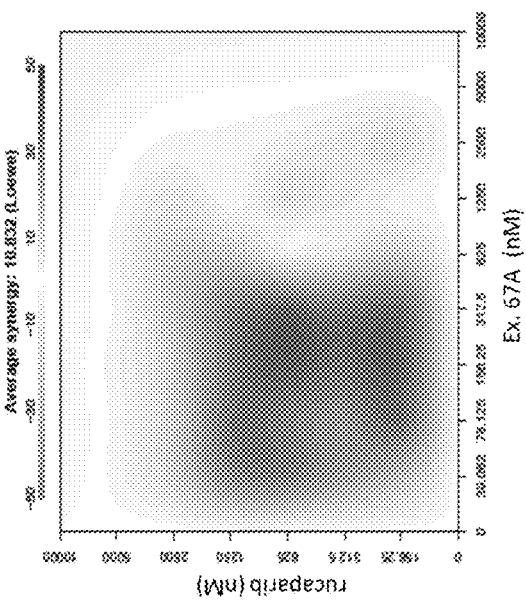
FIG. 1B shows rucaparib—Compound 67A combination studies. Cells treated were Daudi cells. Bar chart is Bliss Independence data plotted, and heatmap is according to Loewe additivity model.
Figure 1B:
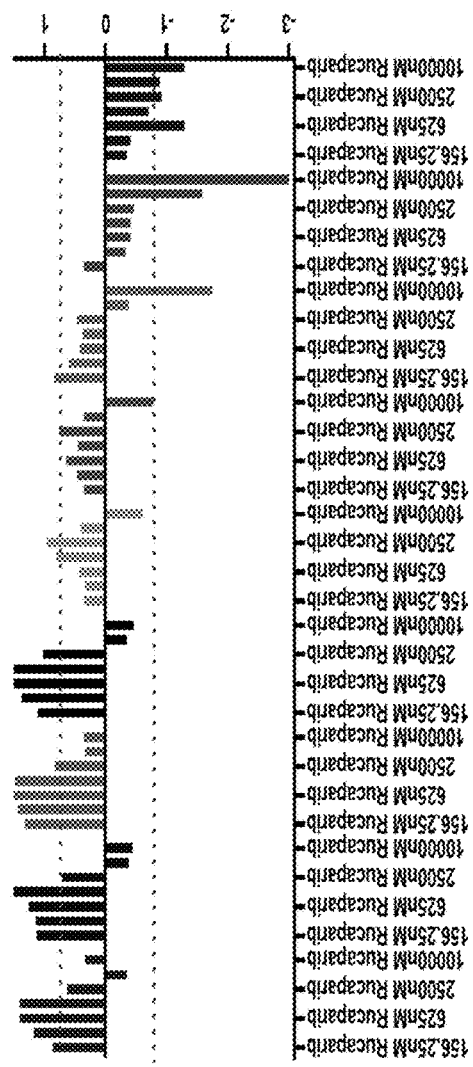
Figures 1C, 2A:
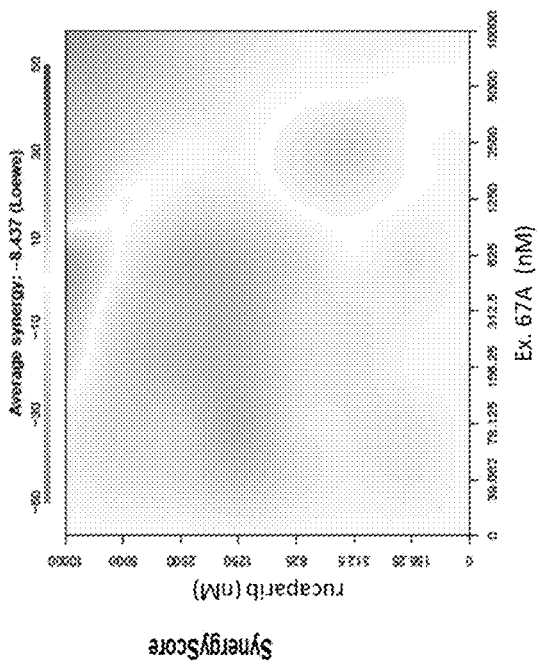
FIG. 1C shows rucaparib—Compound 67A combination studies. Cells treated were ARPE19/HPV16 cells. Bar chart is Bliss Independence data plotted, and heatmap is according to Loewe additivity model.
FIG. 2A shows talazoparib—Compound 67A combination studies. Cells treated were ARPE19/HPV16 cells. Bar chart is Bliss Independence data plotted, and heatmap is according to Loewe additivity model.
Figure 2B:
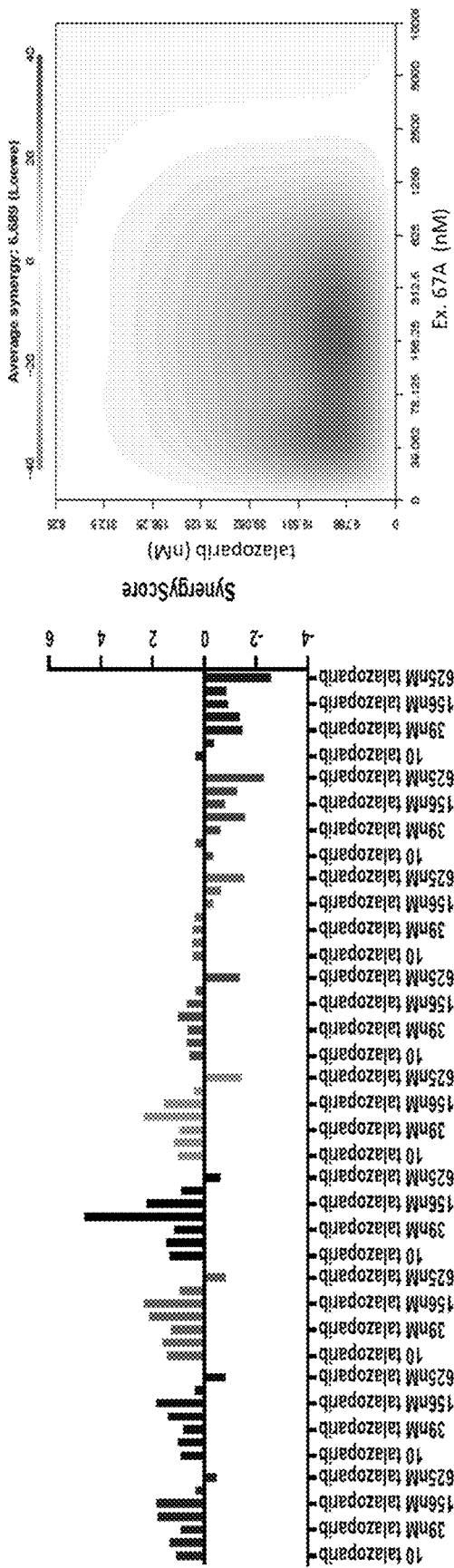
FIG. 2B shows talazoparib—Compound 67A combination studies. Cells treated were Daudi cells. Bar chart is Bliss Independence data plotted, and heatmap is according to Loewe additivity model.
Figure 2C:
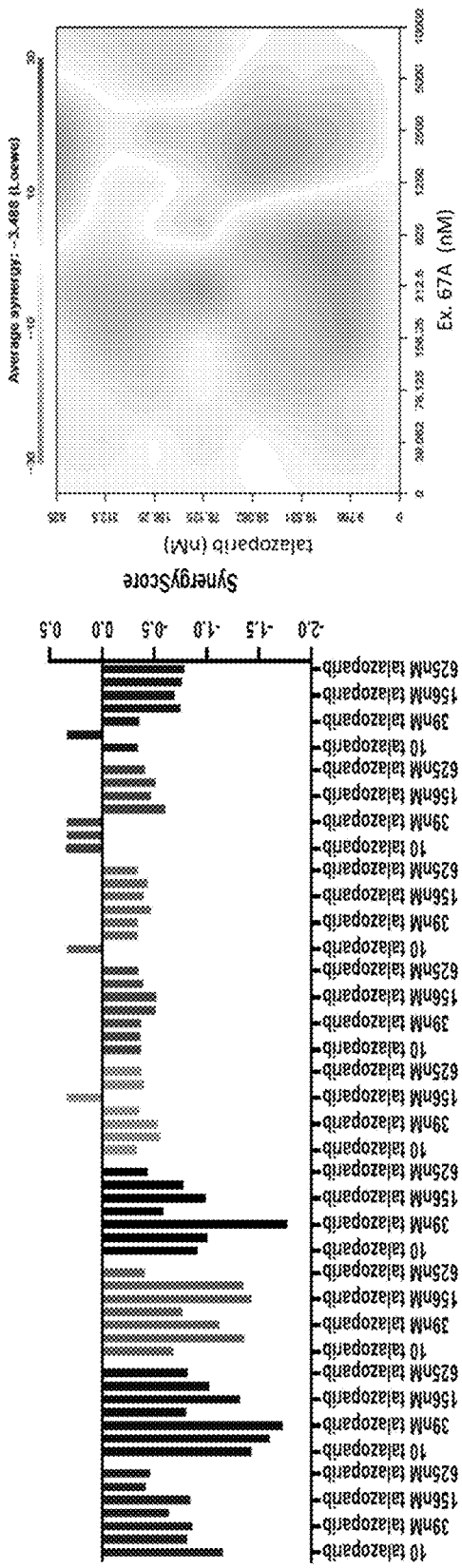
FIG. 2C shows talazoparib—Compound 67A combination studies. Cells treated were ARPE19/HPV16 cells. Bar chart is Bliss Independence data plotted, and heatmap is according to Loewe additivity model.
Figure 3A:
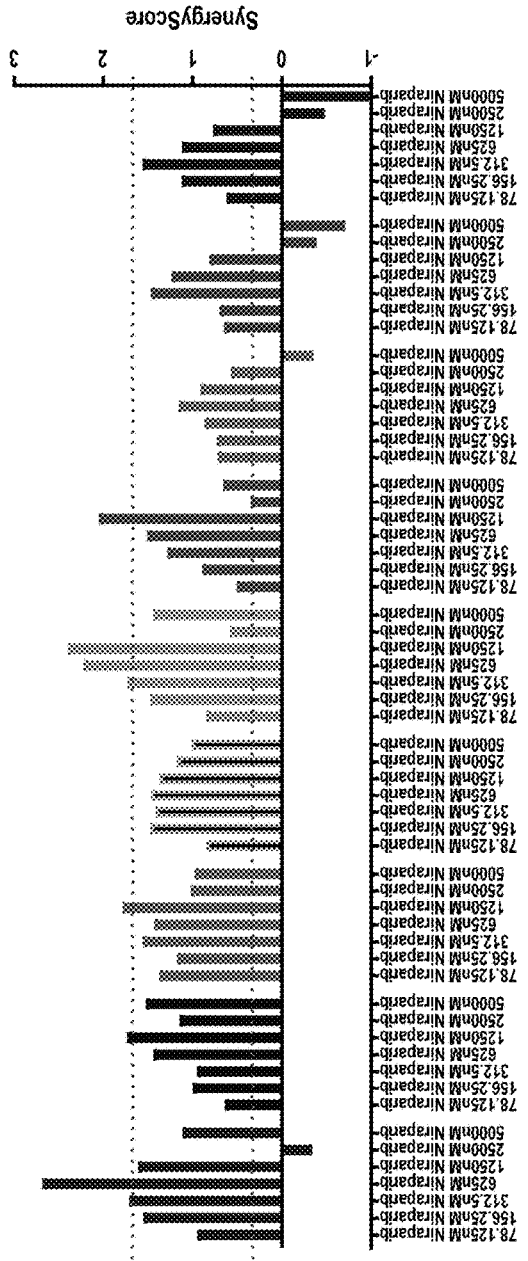
FIG. 3A shows nirapairb—Compound 67A combination studies. Cells treated were ARPE19/HPV16 cells. Bar chart is Bliss Independence data plotted, and heatmap is according to Loewe additivity model.
Figure 3B:
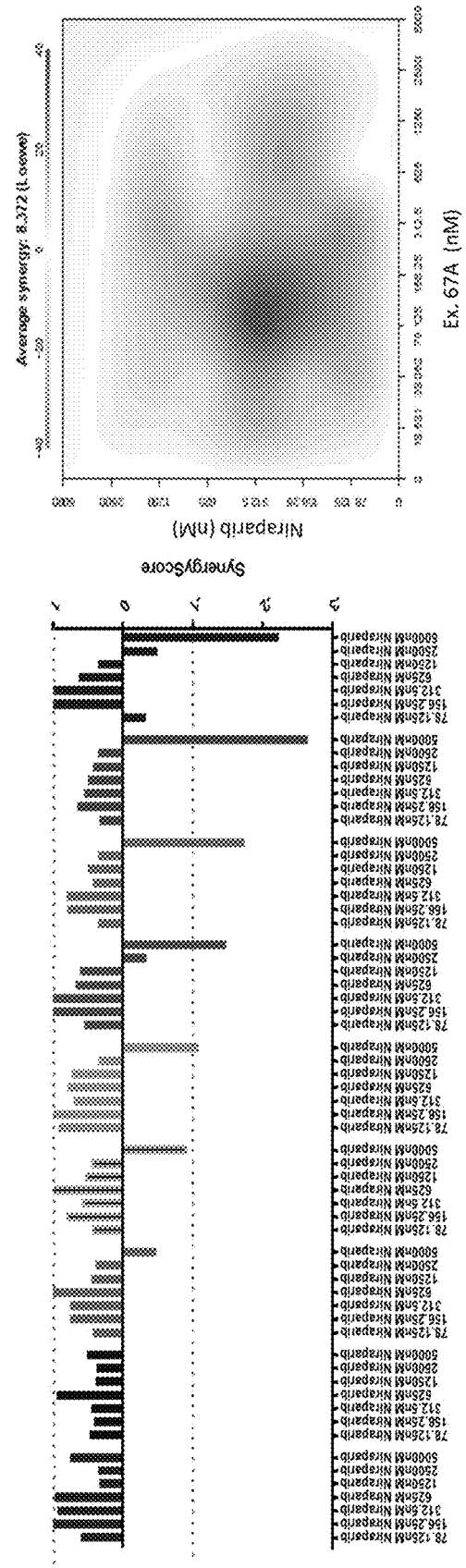
FIG. 3B shows nirapairb—Compound 67A combination studies. Cells treated were Daudi cells. Bar chart is Bliss Independence data plotted, and heatmap is according to Loewe additivity model.
Figure 3C:
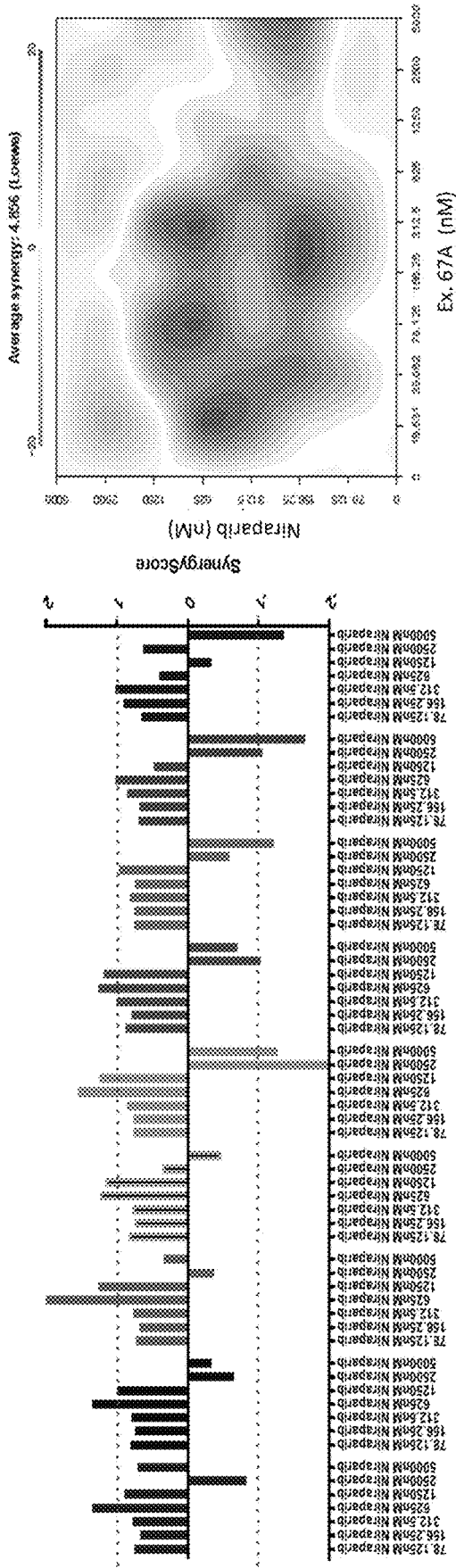
FIG. 3C shows nirapairb—Compound 67A combination studies. Cells treated were ARPE19/HPV16 cells. Bar chart is Bliss Independence data plotted, and heatmap is according to Loewe additivity model.
Figure 4A:
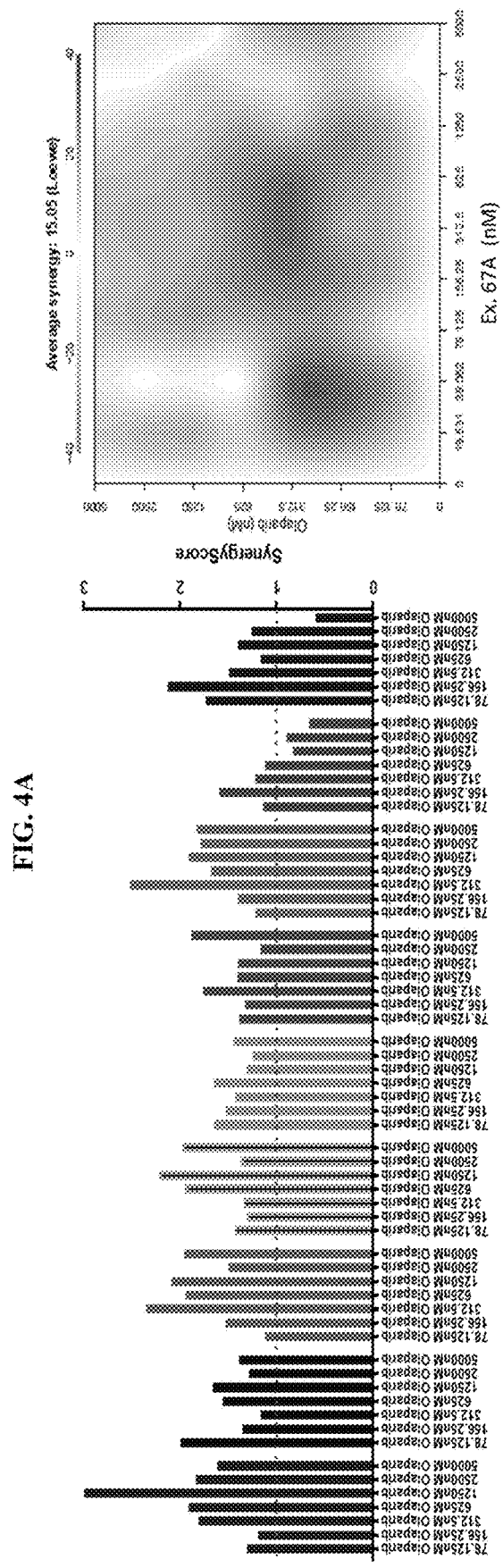
FIG. 4A shows olaparib—Compound 67A combination studies. Cells treated were ARPE19/HPV16 cells. Bar chart is Bliss Independence data plotted, and heatmap is according to Loewe additivity model.
Figure 4B:
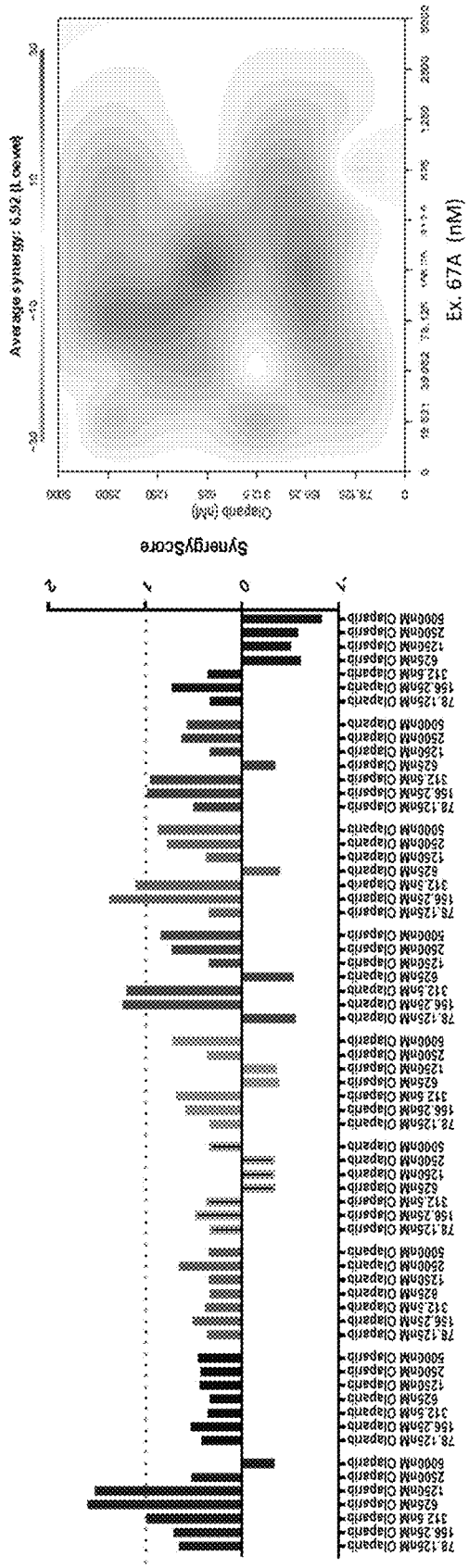
FIG. 4B shows olaparib—Compound 67A combination studies. Cells treated were Daudi cells. Bar chart is Bliss Independence data plotted, and heatmap is according to Loewe additivity model.
Figure 4C:
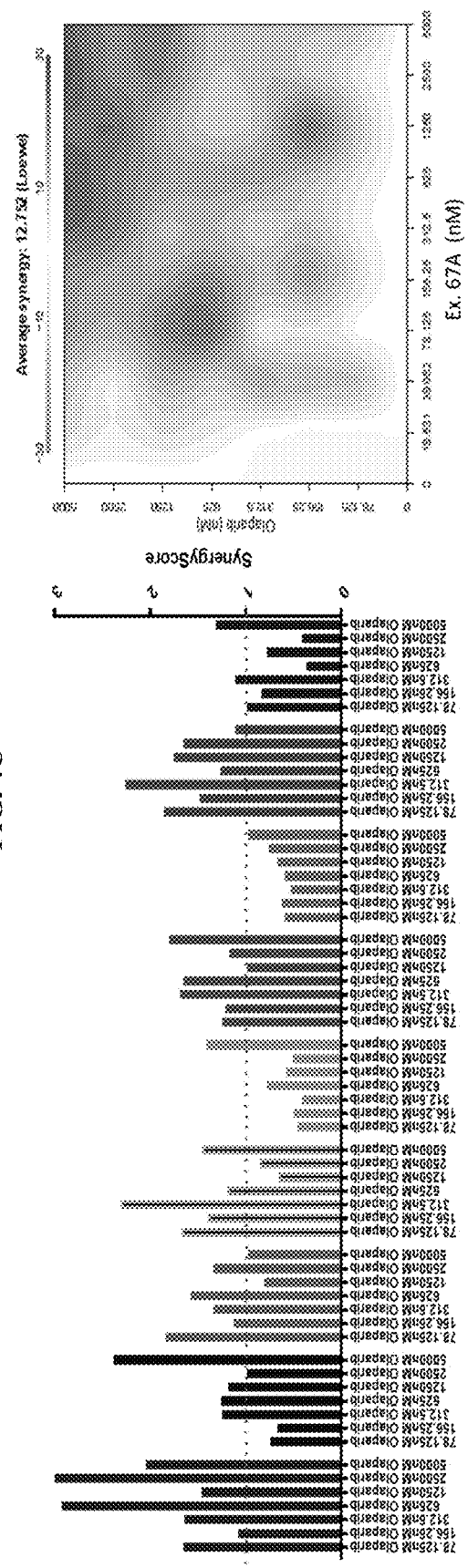
FIG. 4C shows olaparib—Compound 67A combination studies. Cells treated were KYSE-70 cells. Bar chart is Bliss Independence data plotted, and heatmap is according to Loewe additivity model.
Figure 4D:
FIG. 4D shows olaparib—Compound 67A combination studies. Cells treated were BT-20 cells. Bar chart is Bliss Independence data plotted, and heatmap is according to Loewe additivity model.
Figure 4E:
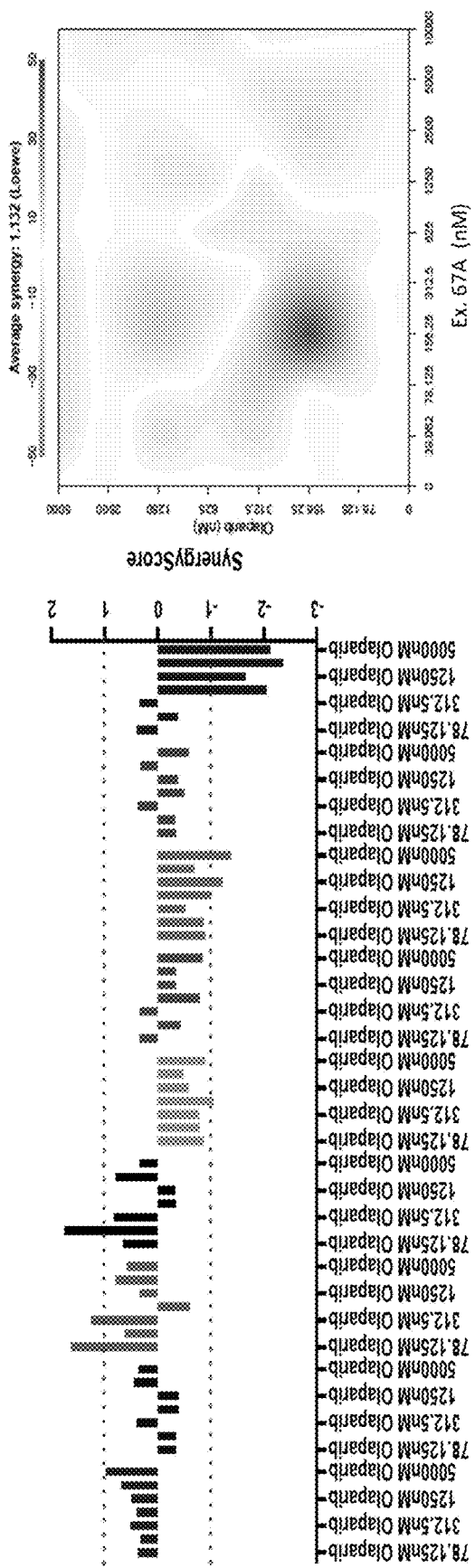
FIG. 4E shows olaparib—Compound 67A combination studies. Cells treated were HCC1937 cells. Bar chart is Bliss Independence data plotted, and heatmap is according to Loewe additivity model.
Figure 5A:
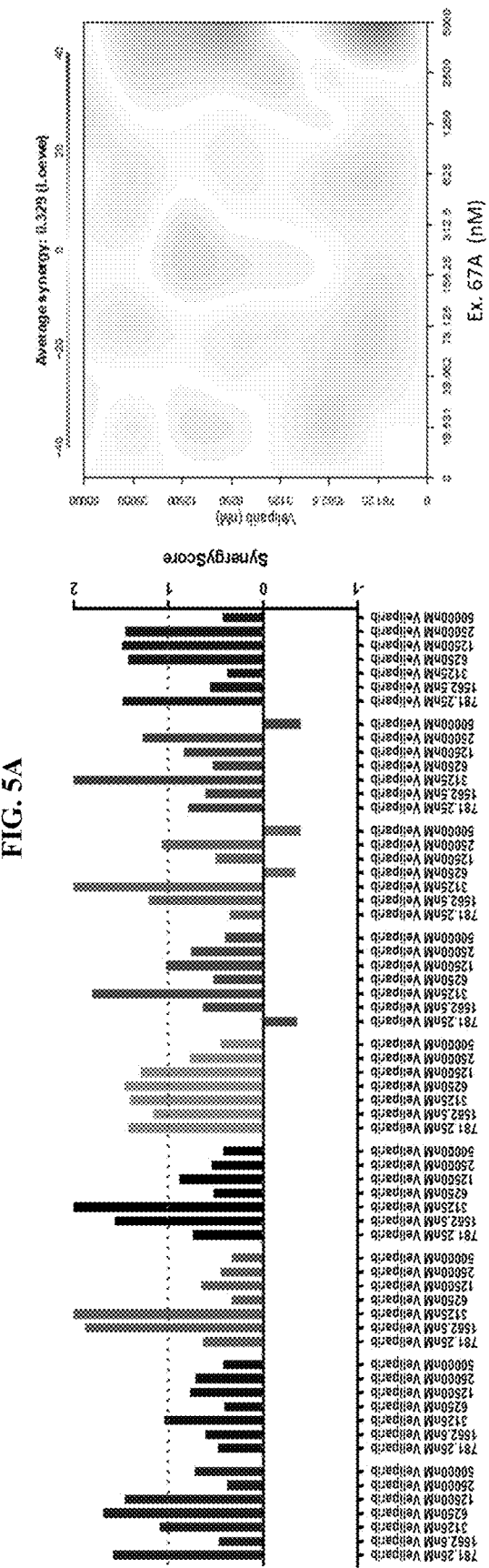
FIG. 5A shows veliparib—Compound 67A combination studies. Cells treated were ARPE19/HPV16 cells. Bar chart is Bliss Independence data plotted, and heatmap is according to Loewe additivity model.
Figure 5B:
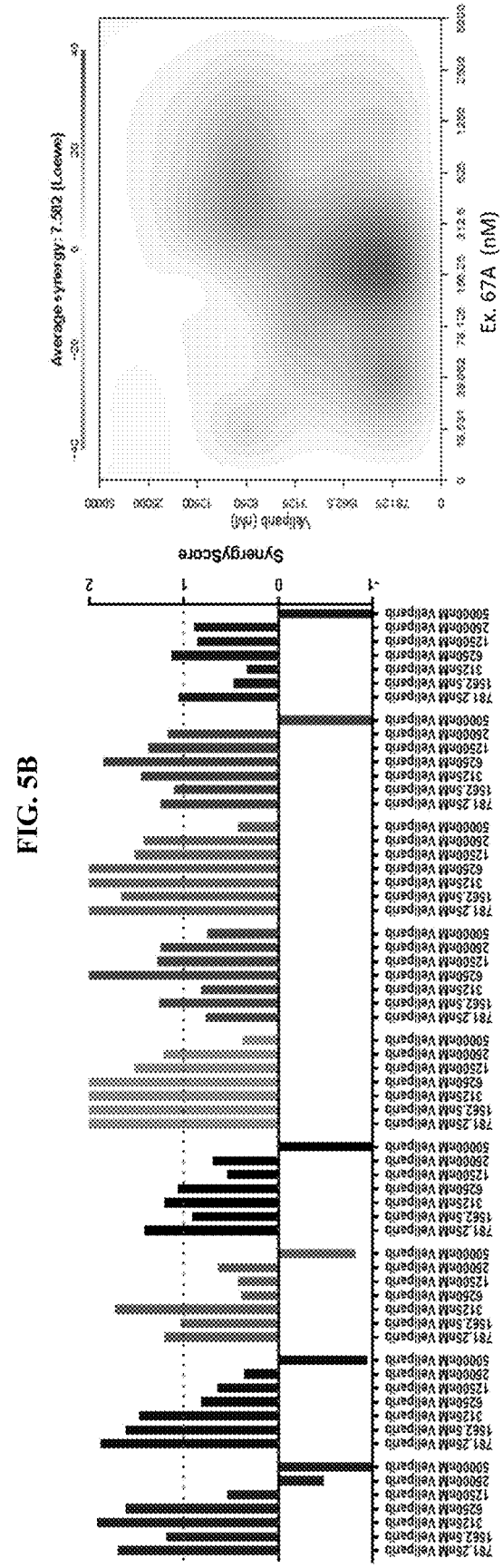
FIG. 5B shows veliparib—Compound 67A combination studies. Cells treated were Daudi cells. Bar chart is Bliss Independence data plotted, and heatmap is according to Loewe additivity model.
Figure 5E:
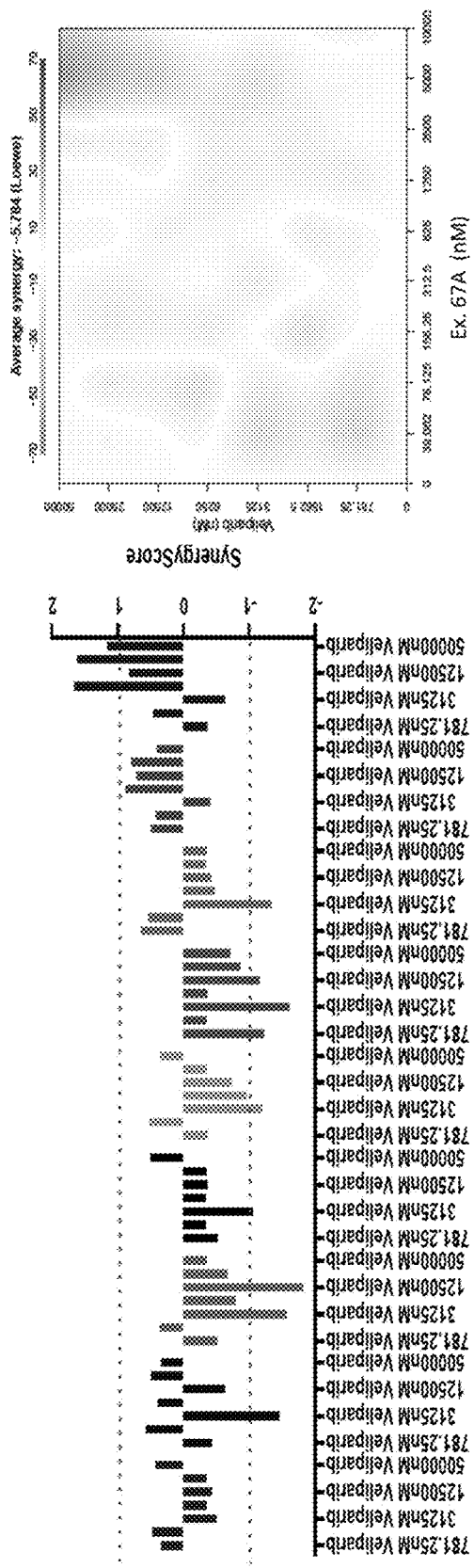
FIG. 5E shows olaparib—Compound 67A combination studies. Cells treated were HCC1937 cells. Bar chart is Bliss Independence data plotted, and heatmap is according to Loewe additivity model.
Figure 6:
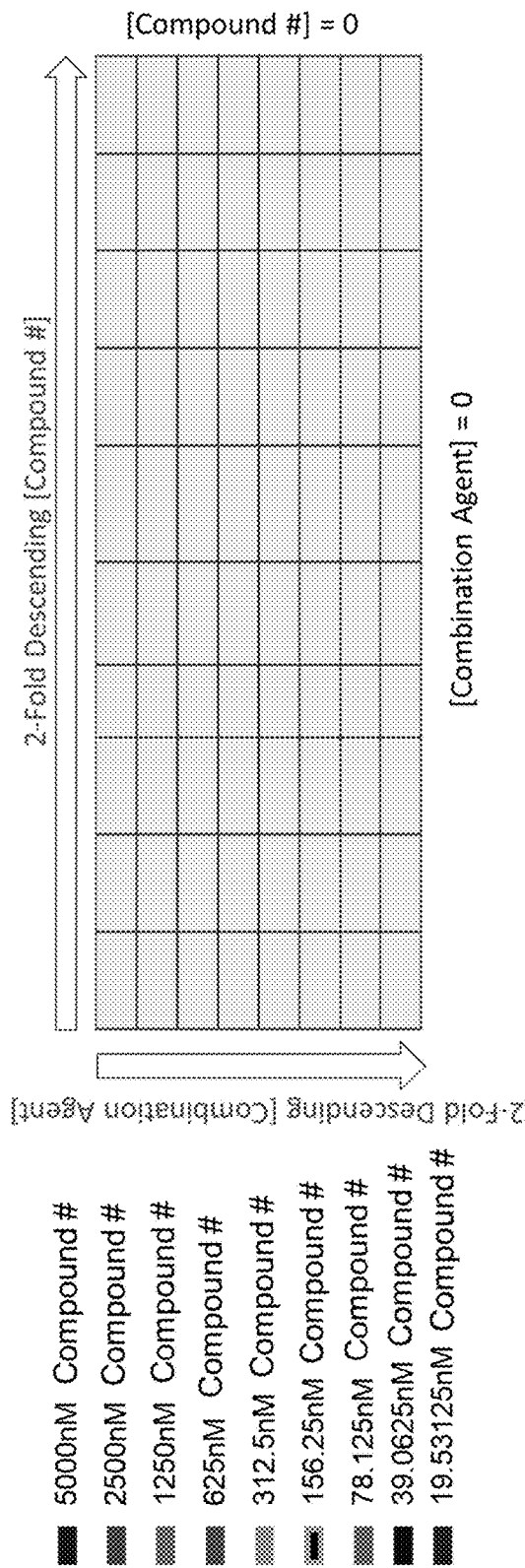
FIG. 6 shows a barchart key denoting concentration of Compound 67A and the experimental setup.
Figure 7B:
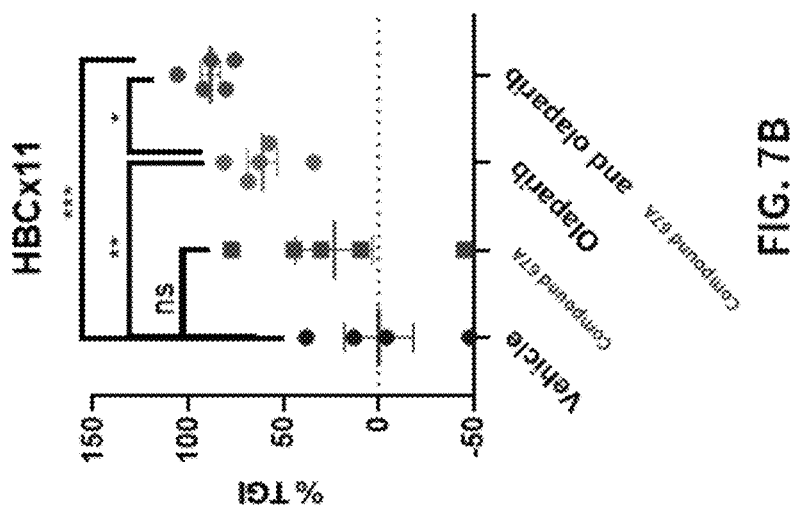
FIG. 7B depicts TGI % with olaparib, Compound 67A, and a combination thereof in a HBCx11 model.
Figure 7A:
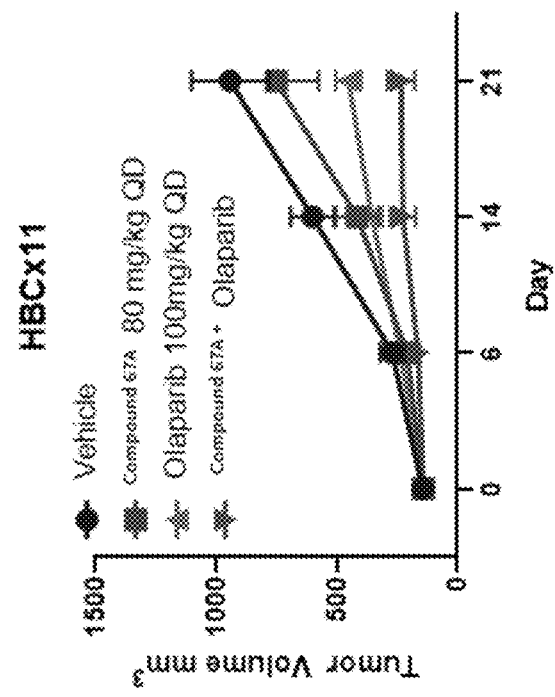
FIG. 7A depicts tumor volume change over day with olaparib, Compound 67A, and a combination thereof in a HBCx11 model.
Figure 8B:
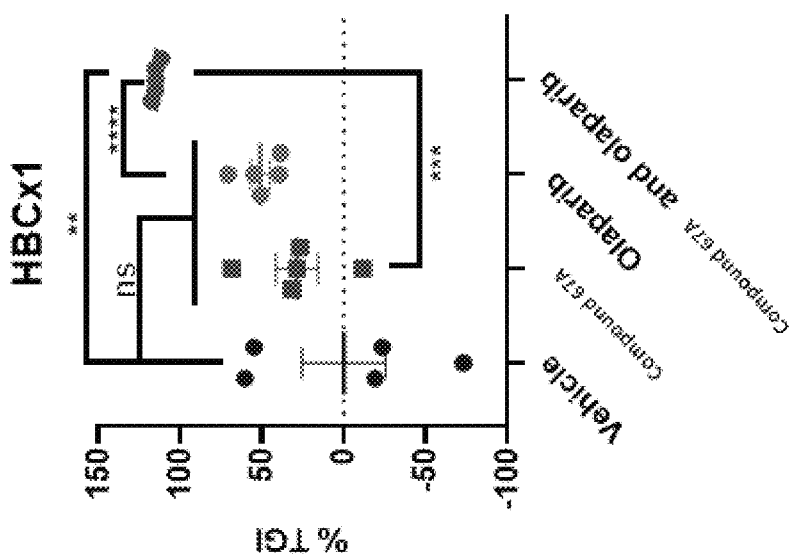
FIG. 8B depicts TGI % with olaparib, Compound 67A, and a combination thereof in a HBCx1 model.
Figure 8A:
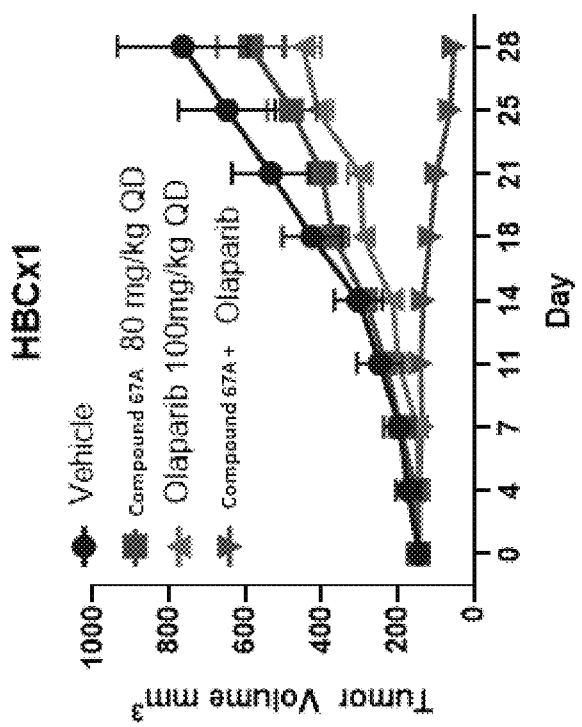
FIG. 8A depicts tumor volume change over day with olaparib, Compound 67A, and a combination thereof in a HBCx1 model.
Figure 9B:
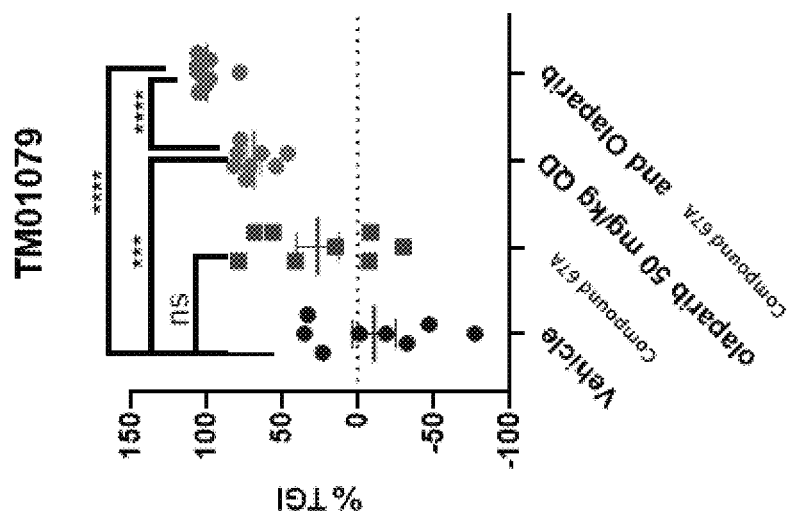
FIG. 9B depicts TGI % with olaparib, Compound 67A, and a combination thereof in a TM01079 model.
Figure 9A:
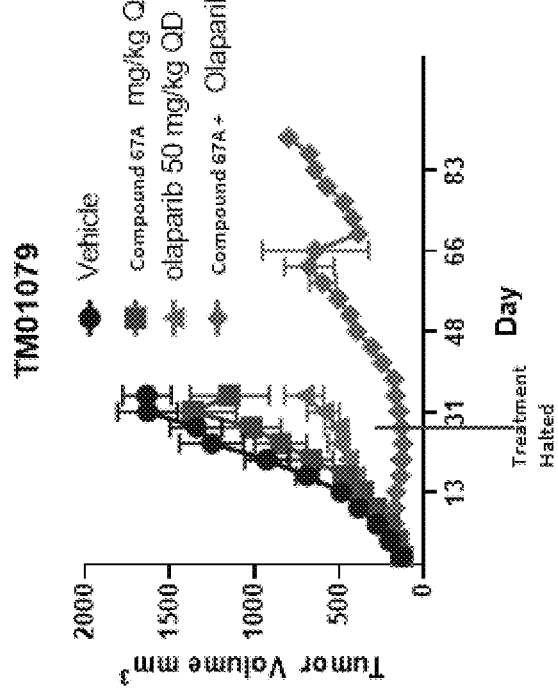
FIG. 9A depicts tumor volume change over day with olaparib, Compound 67A, and a combination thereof in a TM01079 model.
Figure 10B:
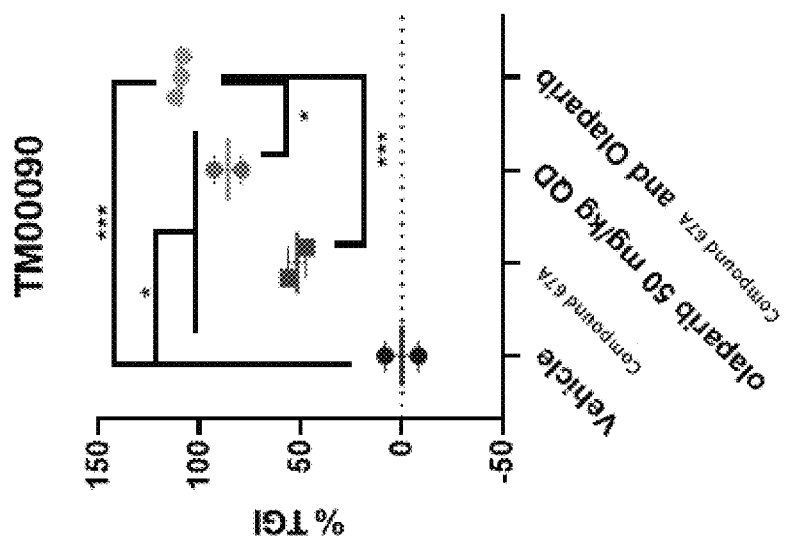
FIG. 10B depicts TGI % with olaparib, Compound 67A, and a combination thereof in a TM00090 model.
Figure 10A:
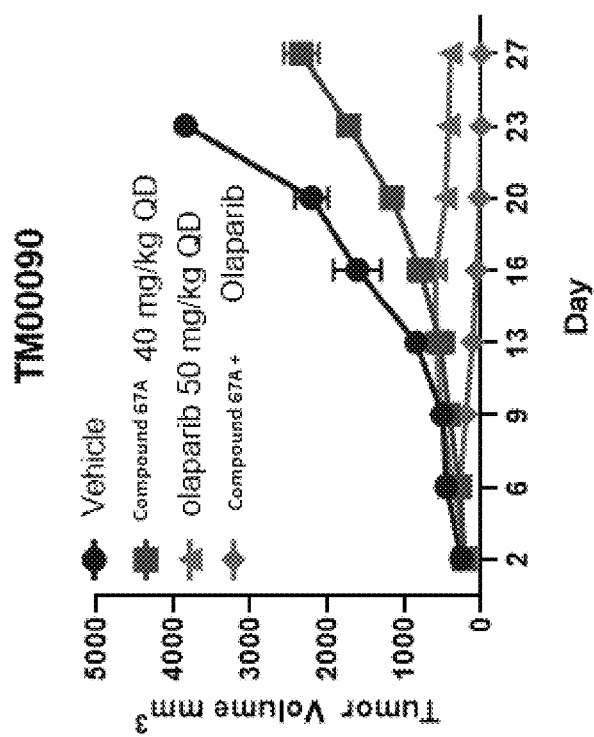
FIG. 10A depicts tumor volume change over day with olaparib, Compound 67A, and a combination thereof in a TM00090 cells.
Figure 11B:
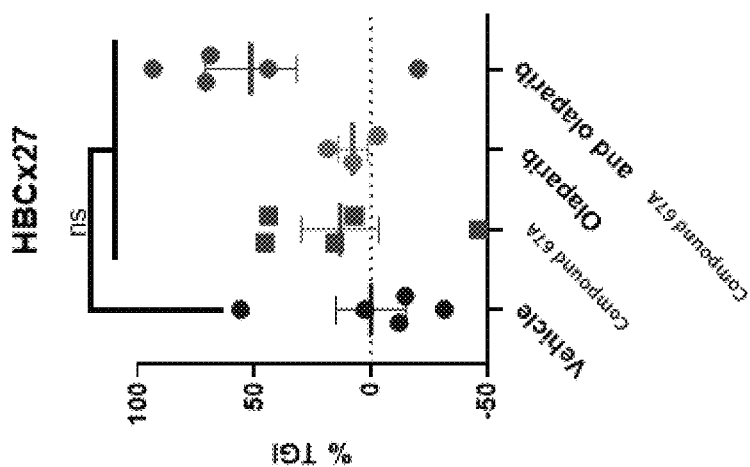
FIG. 11B depicts TGI % with olaparib, Compound 67A, and a combination thereof in a HBCx27 model.
Figure 11A:
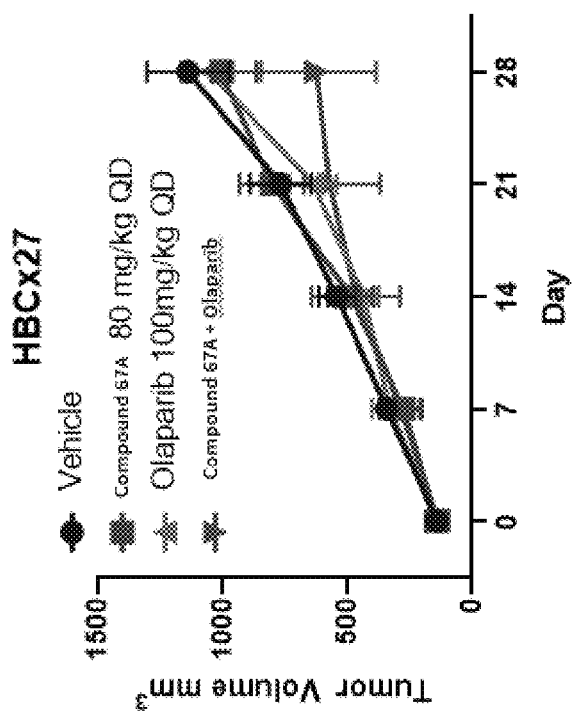
FIG. 11A depicts tumor volume change over day with olaparib, Compound 67A, and a combination thereof in a HBCx27 model.
Figure 12B:
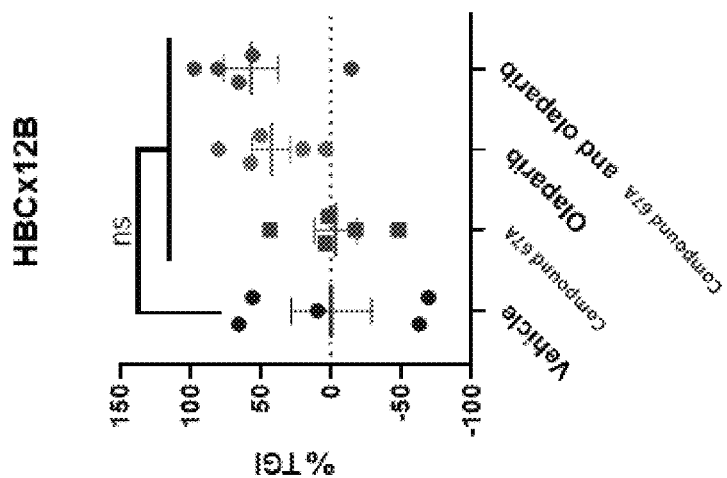
FIG. 12B depicts TGI % with olaparib, Compound 67A, and a combination thereof in a HBCx12B model.
Figure 12A:
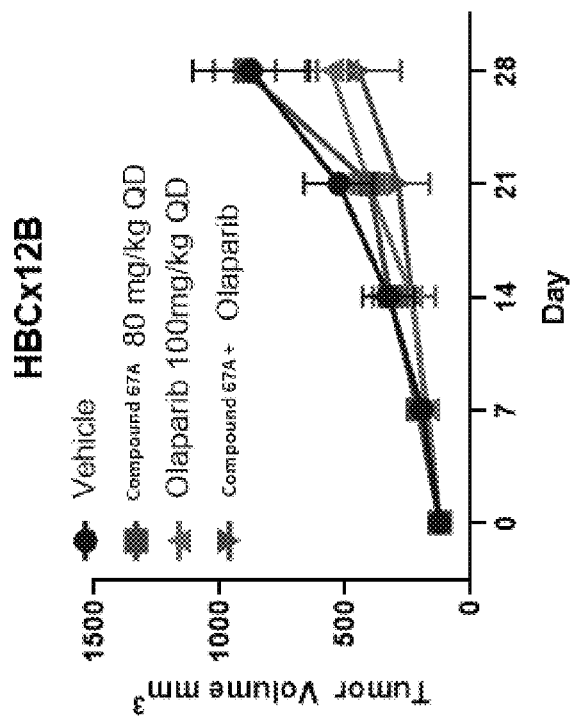
FIG. 12A depicts tumor volume change over day with olaparib, Compound 67A, and a combination thereof in a HBCx12B model.
Figure 13B:
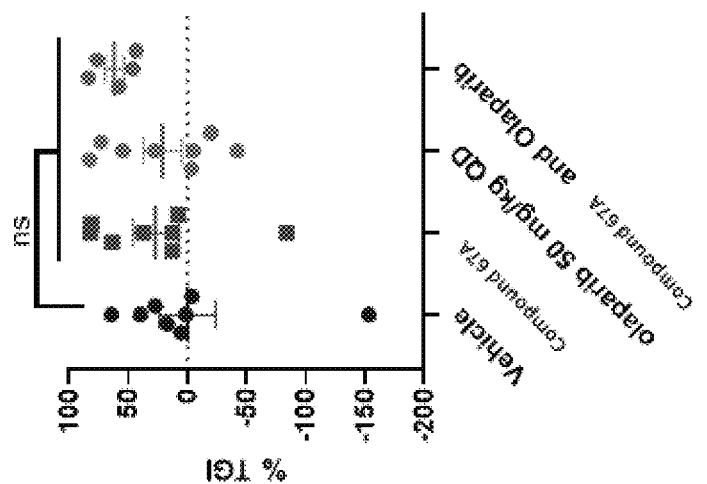
FIG. 13B depicts TGI % with olaparib, Compound 67A, and a combination thereof in a TM00091 model.
Figure 13A:
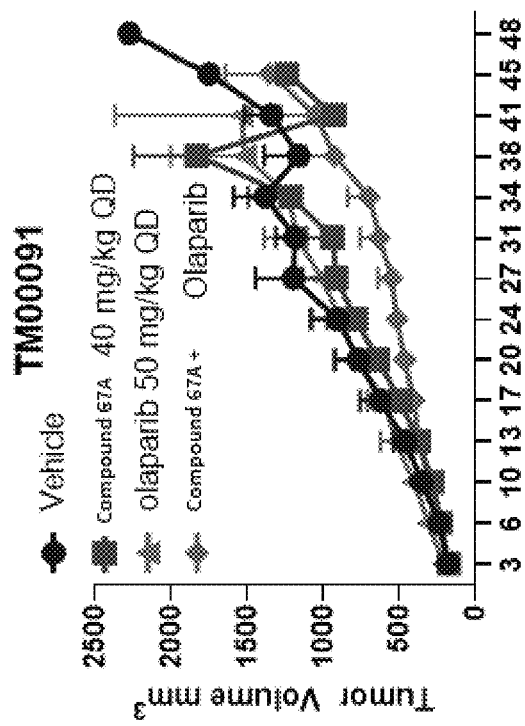
FIG. 13A depicts tumor volume change over day with olaparib, Compound 67A, and a combination thereof in a TM00091 model.

In a first embodiment, the application provides a compound represented by Structural Formula I in combination with a PARP inhibitor:

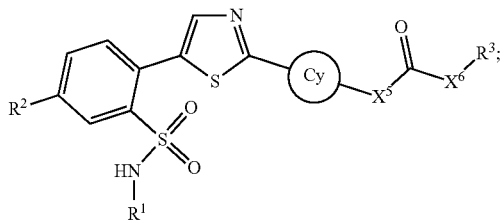

I or a pharmaceutically acceptable salt thereof, wherein:

the thiazole ring is optionally substituted with —F or —Cl;

Cy is —$(C_3-C_7)$cycloalkyl, bridged $(C_6-C_{12})$ cycloalkyl, or a 4-12 membered heterocyclic ring, each of which is optionally substituted with one or more groups selected from the group consisting of halogen, —OH, $(C_1-C_4)$alkyl, and $(C_1-C_4)$alkoxy;

when $X^5$ is connected with a nitrogen ring atom of Cy, $X^5$ is absent;

when $X^5$ is connected with a carbon ring atom of Cy, $X^5$ is $NR^a$ or O;

$X^6$ is $NR^a$ or O;

$R^1$ is $(C_1-C_5)$alkyl;

$R^3$ is $(C_1-C_5)$alkyl, —$CH_2$-phenyl, —$(C_3-C_7)$cycloalkyl, —$CH_2$—$(C_3-C_7)$cycloalkyl, —$CH_2$-monocyclic 3-7 membered heterocyclic ring, or monocyclic 3-7 membered heterocyclic ring, wherein the $(C_1-C_5)$alkyl, —$(C_3-C_7)$cycloalkyl, phenyl or monocyclic 3-7 membered heterocyclic ring represented by $R^3$ or in the group represented by $R^3$ is optionally substituted with one or more groups selected from the group consisting of halogen, —OH, $(C_1-C_4)$alkyl, halomethyl, halomethoxy, —CN, and $(C_1-C_4)$alkoxy;

$R^2$ is —$NR^aC(O)O(C_1-C_4)$alkyl; —$NR^aC(O)NR^a(C_1-C_4)$alkyl; —$NR^aC(O)O(C_2-C_4)$alkenyl; —$NR^aC(O)NR^a(C_2-C_4)$alkenyl; —$NR^aC(O)$—O—$(C_3-C_6)$cycloalkyl; —$NR^aC(O)NR^a$—$(C_3-C_7)$cycloalkyl; —$NR^aC(O)$O-phenyl; —$NR^aC(O)NR^a$-phenyl; —$NR^aC(O)$O-monocyclic 3-7 membered heterocyclic ring; —$NR^aC(O)NR^a$-monocyclic 3-7 membered heterocyclic ring; —$NR^aC(O)$O-monocyclic 5-6 membered heteroaromatic ring; —$NR^aC(O)NR^a$-monocyclic 5-6 membered heteroaromatic ring;

wherein the $(C_1-C_4)$alkyl and the $(C_2-C_4)$alkenyl in the group represented by $R^2$ are each optionally and independently substituted with one or more groups selected from the group consisting of halogen, $N_3$, —$OR^a$, —$NR^aR^a$, —$(C_3-C_6)$cycloalkyl, phenyl, a monocyclic 3-7 membered heterocyclic ring, and a monocyclic 5-6 membered heteroaromatic ring;

wherein the $(C_3-C_7)$cycloalkyl in the group represented by $R^2$ is optionally substituted with one or more groups selected from the group consisting of halogen, —$CH_3$, =O, —$OR^a$ and —$NR^aR^a$;

wherein the phenyl in the group represented by $R^2$ is optionally substituted with one or more groups selected from the group consisting of halogen, —$CH_3$, halomethyl, halomethoxy, —CN, —$OR^a$, and —$N_3$;

wherein the heterocyclic ring in the group represented by $R^2$ is optionally substituted with one or more groups selected from the group consisting of =O, halogen, —$OR^a$, —$CH_3$, halomethyl, and halomethoxy;

wherein the heteroaromatic ring in the group represented by $R^2$ is optionally substituted with one or more groups selected from the group consisting of halogen, —CN, —$CH_3$, halomethyl, halomethoxy, —$OR^a$ and —$NR^aR^a$; and each $R^a$ is independently —H or —$CH_3$.

In a second embodiment, the application provides a compound represented by Structural Formula II in combination with a PARP inhibitor:

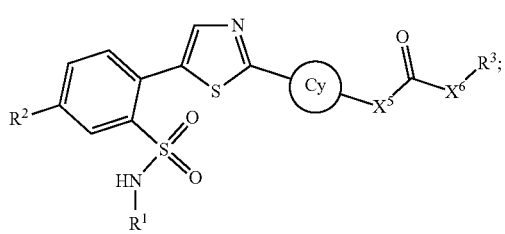

II or a pharmaceutically acceptable salt thereof, wherein the thiazole ring is optionally substituted with —F or —Cl;

Cy is cyclohexyl or a 6-membered monocyclic heterocyclic ring;

$X^5$ and $X^6$ are each independently $NR^a$ or O;

$R^1$ is $(C_1-C_5)$alkyl;

$R^3$ is $(C_1-C_5)$alkyl or monocyclic 3-7-membered heterocyclic ring;

$R^2$ is —$NR^aC(O)O(C_1-C_4)$alkyl; —$NR^aC(O)NR^a(C_1-C_4)$ alkyl; —$NR^aC(O)O(C_2-C_4)$alkenyl; —$NR^aC(O)NR^a(C_2-C_4)$alkenyl; —$NR^aC(O)$—O$(C_3-C_6)$cycloalkyl; —$NR^aC(O)$ $NR^a$—$(C_3-C_6)$cycloalkyl; —$NR^aC(O)$O-phenyl; —$NR^aC(O)NR^a$-phenyl; —$NR^aC(O)$O-monocyclic 3-7 membered heterocyclic ring; —$NR^aC(O)NR^a$-monocyclic 3-7 membered heterocyclic ring; —$NR^aC(O)$O-monocyclic 5-6 membered heteroaromatic ring; —$NR^aC(O)NR^a$-monocyclic 5-6 membered heteroaromatic ring;

wherein the $(C_1-C_4)$alkyl and the $(C_2-C_4)$alkenyl in the group represented by $R^2$ are each optionally and independently substituted with one or more halogen, $N_3$, —$OR^a$, —$NR^aR^a$, —$(C_3-C_6)$cycloalkyl, phenyl, monocyclic 3-7-membered heterocyclic ring, or monocyclic 5-6-membered heteroaromatic ring;

wherein the —$(C_3-C_6)$cycloalkyl in the group represented by $R^2$ is optionally substituted with one or more halogen, —$CH_3$, —$OR^a$ or —$NR^aR^a$;

wherein the phenyl in the group represented by $R^2$ is optionally substituted with one or more halogen, —$CH_3$, halomethyl, halomethoxy, —$OR^a$, or —$N_3$;

wherein the heterocyclic ring in the group represented by $R^2$ is optionally substituted with one or more =O, halogen, —$CH_3$, halomethyl, or halomethoxy;

wherein the heteroaromatic ring in the group represented by $R^2$ is optionally substituted with one or more halogen, —$CH_3$, halomethyl, halomethoxy, —$OR^a$ or —$NR^aR^a$; and each $R^a$ is independently —H or —$CH_3$.

In a third embodiment, the application provides a compound according to Structural Formula I, or a pharmaceutically acceptable salt thereof, in combination with a PARP inhibitor, wherein Cy is cyclopropyl, cyclobutyl, cyclopentyl, cyclohexyl, cycloheptyl; azetidinyl, azepanyl, diazaspiro[4.4]nonyl, diazaspiro[3.5]nonyl, diazepanyl, dihydroimidazole, dihydrofuranyl, dihydropyranyl, dihydropyridinyl, dihydropyrimidinyl, dihydrothienyl, dihydrothiophenyl, dihydrothiopyranyl, hexahydropyridazinyl, hexahydropyrimidinyl, hydantoinyl, indolinyl, isoindolinyl, morpholinyl, oxiranyl, oxetanyl, piperidinyl, piperazinyl, pyrrolidinonyl, pyrrolidinyl, tetrahydrofuranyl, tetrahydroimidazole, tetrahydroindolyl, tetrahydropyranyl, tetrahydrothienyl, tetrahydropyridinyl, tetrahydropyrimidinyl, tetrahydrothiophenyl, tetrahydrothiopyranyl, thiomorpholinyl, tropanyl, valerolactamyl; bicyclo[2.1.1]hexyl, bicyclo[2.2.1]heptyl, bicyclo[2.2.2]octyl, bicyclo[3.2.1]octyl, bicyclo[4.3.1]decyl, bicyclo[3.3.1]nonyl, bornyl, bornenyl, norbornyl, norbornenyl, 6,6-dimethylbicyclo [3.1.1]heptyl, tricyclobutyl, adamantly; azanorbornyl, quinuclidinyl, isoquinuclidinyl, tropanyl, azabicyclo[2.2.1]heptanyl, 2-azabicyclo[3.2.1]octanyl, azabicyclo[3.2.1]octanyl, azabicyclo[3.2.2]nonanyl, azabicyclo[3.3.0]nonanyl, azabicyclo [3.3.1]nonanyl, diazabicyclo[2.2.1]heptanyl, diazabicyclo[3.2.1]octanyl, octahydropyrrolo[3,4-b]pyrrolyl, octahydropyrrolo[3,4-c]pyrrolyl; and the remaining variables are as defined in the first embodiment.

In a fourth embodiment, the application provides a compound according to Structural Formula I or II, or a pharmaceutically acceptable salt thereof, in combination with a PARP inhibitor, wherein Cy is cyclohexyl, morpholinyl, thiomorpholinyl, piperidinyl, piperazinyl, hexahydropyridazinyl, hexahydropyrimidinyl, valerolactamyl, dihydropyranyl, dihydropyridinyl, dihydropyrimidinyl, dihydrothiopyranyl, tetrahydropyranyl, tetrahydropyridinyl, tetrahydropyrimidinyl, or tetrahydrothiopyranyl; and the remaining variables are as defined in the first, second, and/or third embodiments.

In a fifth embodiment, the application provides a compound represented by Structural Formula III in combination with a PARP inhibitor:

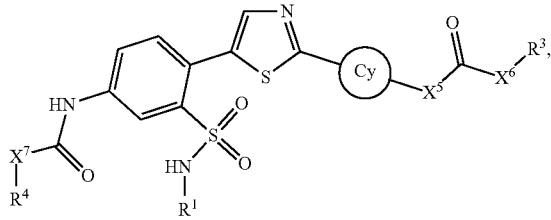

III or a pharmaceutically acceptable salt thereof, wherein:

$X^7$ is NH or O;

$R^4$ is ($C_1$-$C_4$)alkyl, ($C_3$-$C_6$)cycloalkyl, or a monocyclic 3-7 membered heterocyclic ring;

wherein the ($C_1$-$C_4$)alkyl represented by $R^4$ is optionally substituted with one or more groups selected from the group consisting of halogen, $N_3$, —$OR^a$, —$NR^aR^a$, —($C_3$-$C_6$)cycloalkyl, phenyl, a monocyclic 3-7 membered heterocyclic ring, and a monocyclic 5-6 membered heteroaromatic ring, wherein the ($C_3$-$C_6$)cycloalkyl or the monocyclic 3-7 membered heterocyclic ring represented by $R^4$, the ($C_3$-$C_6$)cycloalkyl or the monocyclic 3-7 membered heterocyclic ring in the group represented by $R^4$ is optionally substituted with one or more groups selected from the group consisting of halogen, —$OR^a$, =O, and —$CH_3$, wherein the phenyl in the group represented by $R^4$ is optionally substituted with one or more groups selected from the group consisting of halogen, —$CH_3$, halomethyl, halomethoxy, —$OR^a$, and —$N_3$;

wherein the heteroaromatic ring in the group represented by $R^4$ is optionally substituted with one or more groups selected from the group consisting of halogen and —$CH_3$; and the remaining variables are as defined in the first, second, third, and/or fourth embodiments.

In a sixth embodiment, the application provides a compound according to Structural Formula III, or a pharmaceutically acceptable salt thereof, in combination with a PARP inhibitor, wherein $X^7$ is NH or O; $R^3$ is ($C_1$-$C_5$)alkyl; and $R^4$ is ($C_1$-$C_4$)alkyl wherein the ($C_1$-$C_4$)alkyl represented by $R^4$ is optionally substituted with one or more halogen, —$OR^a$, —$NR^aR^a$, —($C_3$-$C_6$)cycloalkyl, phenyl (optionally substituted by one or more halogen, —$CH_3$, halomethyl, halomethoxy, $OR^a$ or $N_3$), monocyclic 3-7-membered heterocyclic ring (optionally substituted by =O, halogen or —$CH_3$), or monocyclic 5-6-membered heteroaromatic ring (optionally substituted by halogen or —$CH_3$); and the remaining variables are as defined in the first, second, third, fourth and/or fifth embodiments.

In a seventh embodiment, the application provides a compound represented by Structural Formula IV in combination with a PARP inhibitor:

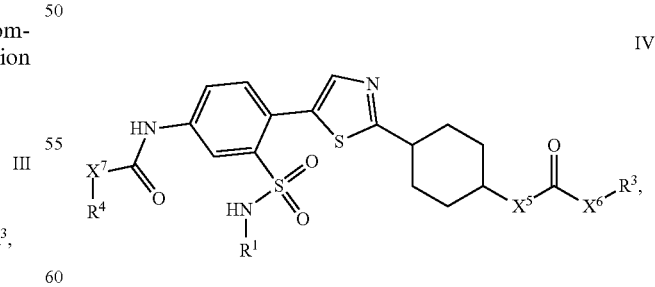

IV or a pharmaceutically acceptable salt thereof; and the variables are as defined in the first, second, third, fourth, fifth and/or sixth embodiments.

In an eighth embodiment, the application provides a compound represented by Structural Formula V in combination with a PARP inhibitor:

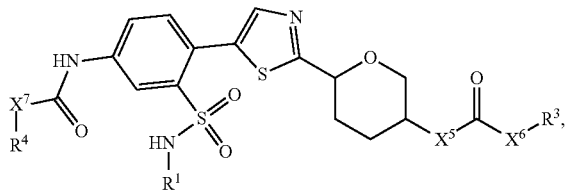

or a pharmaceutically acceptable salt thereof; and the variables are as defined in the first, second, third, fourth, fifth and/or sixth embodiments.

In a ninth embodiment, the application provides a compound represented by Structural Formula VI in combination with a PARP inhibitor:

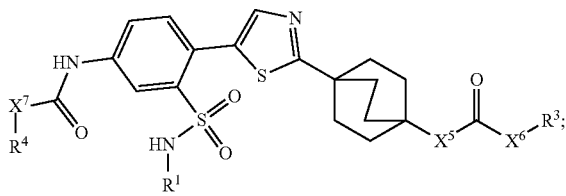

or a pharmaceutically acceptable salt thereof; and the variables are as defined in the first, second, third, fourth, fifth and/or sixth embodiments.

In a tenth embodiment, the application provides a compound represented by Structural Formula VII in combination with a PARP inhibitor:

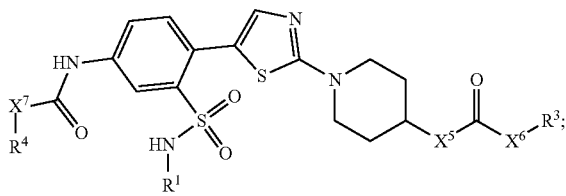

or a pharmaceutically acceptable salt thereof; and the variables are as defined in the first, second, third, fourth, fifth and/or sixth embodiments.

In an eleventh embodiment, the application provides a compound represented by Structural Formula VIII in combination with a PARP inhibitor:

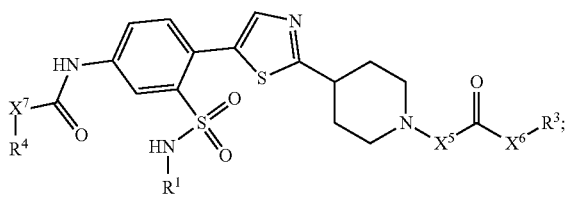

or a pharmaceutically acceptable salt thereof; and the variables are as defined in the first, second, third, fourth, fifth and/or sixth embodiments.

In a twelfth embodiment, the application provides a compound represented by Structural Formula IX in combination with a PARP inhibitor:

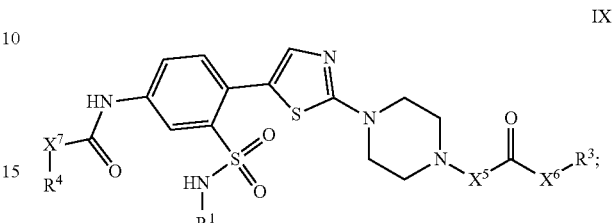

or a pharmaceutically acceptable salt thereof; and the variables are as defined in the first, second, third, fourth, fifth and/or sixth embodiments.

In a thirteenth embodiment, the application provides a compound according to Structural Formula I, II, or III, or a pharmaceutically acceptable salt thereof, in combination with a PARP inhibitor, wherein Cy is azetidinyl or pyrrolidinyl, and the nitrogen ring atom is connected with the thiazole ring; and the remaining variables are as defined in the first, second, third, fourth, fifth and/or sixth embodiments.

In a fourteenth embodiment, the application provides a compound according to Structural Formula I, II, or III, or a pharmaceutically acceptable salt thereof, in combination with a PARP inhibitor, wherein Cy is 1,7-diazaspiro[4.4]nonyl, 2,7-diazaspiro[4.4]nonyl, 2,7-diazaspiro[3.5]nonyl, 1,4-diazepanyl, 2,5-diazabicyclo[2.2.1]heptanyl, 3,8-diazabicyclo[3.2.1]octanyl, octahydropyrrolo[3,4-b]pyrrolyl, or octahydropyrrolo[3,4-c]pyrrolyl, and the two nitrogen ring atoms are connected with the thiazole ring and the —$X^5C(O)X^6R^3$ moiety, respectively; and the remaining variables are as defined in the first, second, third, fourth, fifth and/or sixth embodiments.

In a fifteenth embodiment, the application provides a compound according to Structural Formula III, IV, V, VI, VII, VIII, or IX, or a pharmaceutically acceptable salt thereof, in combination with a PARP inhibitor, wherein $R^4$ is —$(C_1$-$C_3)$alkyl, $(C_3$-$C_6)$cycloalkyl, or a monocyclic 3-7 membered heterocyclic ring, wherein the —$(C_1$-$C_3)$alkyl is optionally substituted with (i) phenyl optionally substituted by one or more halogen or —$CH_3$; (ii) a monocyclic 5-6 membered heteroaromatic ring optionally substituted by one or more halogen or —$CH_3$; or (iii) a monocyclic 3-7 membered heterocyclic ring optionally substituted by one or more groups selected from the group consisting of halogen and —$CH_3$; and the remaining variables are as defined in the first, second, third, fourth, fifth, seventh, eighth, ninth, tenth, eleventh, twelfth, thirteenth, and/or fourteenth embodiments.

In a sixteenth embodiment, the application provides a compound according to Structural Formula III, IV, V, VI, VII, VIII, or IX, or a pharmaceutically acceptable salt thereof, in combination with a PARP inhibitor, wherein $R^4$ is —$(C_1$-$C_3)$alkyl, —$CHR^a$-phenyl, —$CHR^a$-5-6 membered heteraromatic ring, or —$CHR^a$-3-7 membered monocyclic heterocyclic ring, wherein the phenyl, 5-6 membered heteraromatic ring or 3-7 membered monocyclic heterocyclic ring in the group represented by $R^4$ is optionally substituted one or more groups selected from the group consisting of halogen and —CH$_3$; and the remaining variables are as defined in the first, second, third, fourth, fifth, seventh, eighth, ninth, tenth, eleventh, twelfth, thirteenth, and/or fourteenth embodiments.

In a seventeenth embodiment, the application provides a compound according to Structural Formula III, IV, V, VI, VII, VIII, or IX, or a pharmaceutically acceptable salt thereof, in combination with a PARP inhibitor, wherein $R^4$ is —(C$_1$-C$_3$)alkyl, optionally substituted with (i) phenyl optionally substituted by one or more halogen, —CH$_3$, halomethyl, halomethoxy, OR$^a$, or N$_3$; (ii) a monocyclic 5-6-membered heteroaromatic ring optionally substituted by one or more halogen or —CH$_3$; or (iii) a monocyclic 3-7-membered heterocyclic ring optionally substituted by one or more =O or —CH$_3$; and the remaining variables are as defined in the first, second, third, fourth, fifth, sixth, seventh, eighth, ninth, tenth, eleventh, twelfth, thirteenth, and/or fourteenth embodiments.

In an eighteenth embodiment, the application provides a compound according to Structural Formula III, IV, V, VI, VII, VIII, or IX, or a pharmaceutically acceptable salt thereof, in combination with a PARP inhibitor, wherein $R^4$ is —(C$_1$-C$_3$)alkyl, optionally substituted with (i) phenyl optionally substituted by one or more halogen, —CH$_3$, halomethyl, halomethoxy, OR$^a$, or N$_3$; (ii) a monocyclic 5-6-membered heteroaromatic ring optionally substituted by one or more halogen or —CH$_3$; or (iii) a monocyclic 3-7-membered heterocyclic ring optionally substituted by one or more =O or —CH$_3$; and the remaining variables are as defined in the first, second, third, fourth, fifth, sixth, seventh, eighth, ninth, tenth, eleventh, twelfth, thirteenth, fourteenth, and/or seventeenth embodiments.

In a nineteenth embodiment, the application provides a compound according to Structural Formula I, III, IV, V, VI, VII, VIII, or IX, or a pharmaceutically acceptable salt thereof, in combination with a PARP inhibitor, wherein $R^3$ is (C$_1$-C$_4$)alkyl, —(C$_4$-C$_6$)cycloalkyl, —CH$_2$-phenyl, —CH$_2$-monocyclic 4-6 membered heterocyclic ring, or monocyclic 4-6 membered heterocyclic ring, wherein the phenyl or monocyclic 4-6 membered heterocyclic ring represented by $R^3$ or in the group represented by $R^3$ is optionally substituted with one or more groups selected from the group consisting of halogen, —OR$^a$, and —CH$_3$; and the remaining variables are as defined in the first, third, fourth, fifth, seventh, eighth, ninth, tenth, eleventh, twelfth, thirteenth, fourteenth, fifteenth, sixteenth, seventeenth, and/or eighteenth embodiments.

In a twentieth embodiment, the application provides a compound represented by Structural Formula X in combination with a PARP inhibitor:

X

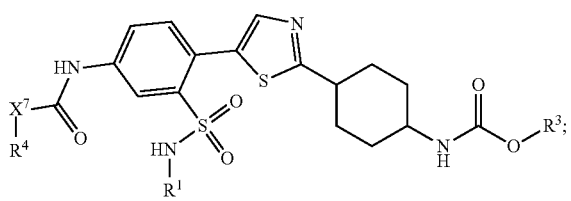

or a pharmaceutically acceptable salt thereof; and the variables are as defined in the first, second, third, fourth, fifth, sixth, seventh, fifteenth, sixteenth, seventeenth, eighteenth, and/or nineteenth embodiments.

In a twenty first embodiment, the application provides a compound represented by Structural Formula XI in combination with a PARP inhibitor:

XI

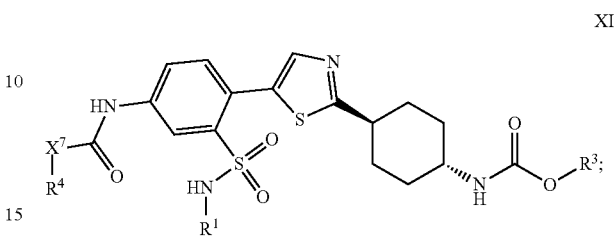

or a pharmaceutically acceptable salt thereof; and the variables are as defined in the first, second, third, fourth, fifth, sixth, seventh, fifteenth, sixteenth, seventeenth, eighteenth, and/or nineteenth embodiments.

In a twenty second embodiment, the application provides a compound represented by Structural Formula XII in combination with a PARP inhibitor:

XII

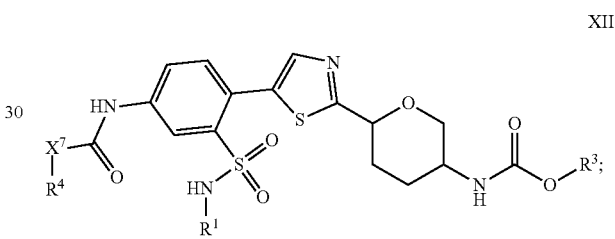

or a pharmaceutically acceptable salt thereof; and the variables are as defined in the first, second, third, fourth, fifth, sixth, eighth, fifteenth, sixteenth, seventeenth, eighteenth, and/or nineteenth embodiments.

In a twenty third embodiment, the application provides a compound represented by Structural Formula XIII(a) or XIII(b) in combination with a PARP inhibitor:

XIII(a)

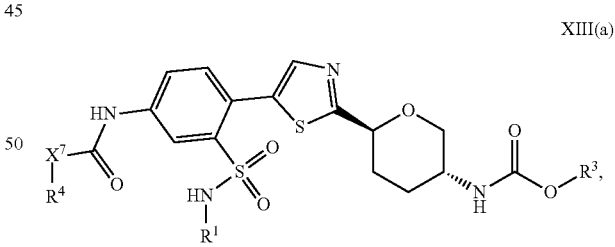

or

XIII(b)

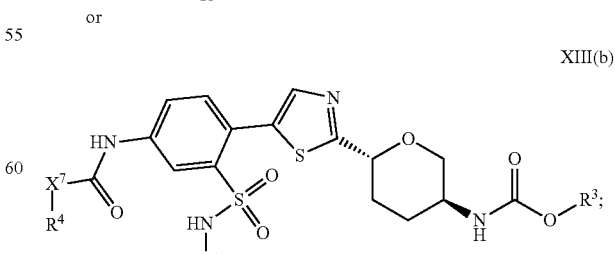

or a pharmaceutically acceptable salt thereof; and the variables are as defined in the first, second, third, fourth, fifth, sixth, eighth, fifteenth, sixteenth, seventeenth, eighteenth, and/or nineteenth embodiments.

In a twenty fourth embodiment, the application provides a compound represented by Structural Formula XIV in combination with a PARP inhibitor:

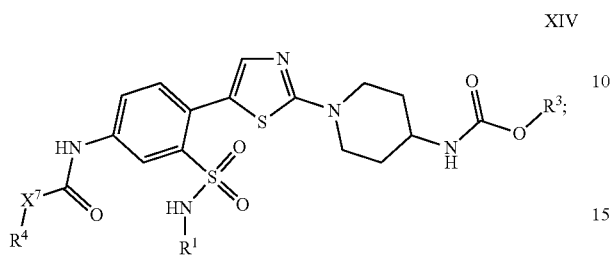

XIV or a pharmaceutically acceptable salt thereof; and the variables are as defined in the first, second, third, fourth, fifth, sixth, tenth, fifteenth, sixteenth, seventeenth, eighteenth, and/or nineteenth embodiments.

In a twenty fifth embodiment, the application provides a compound according to Structural Formula I, II, III, IV, V, VI, VII, VIII, IX, X, XI, XII, XIII(a), XIII(b), XIV, or a pharmaceutically acceptable salt thereof, in combination with a PARP inhibitor, wherein $R^3$ is isopropyl, tert-butyl, cyclobutyl, cyclopentyl, benzyl, oxetanyl, tetrahydro-2H-pyranyl, or

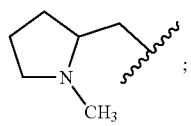

and the variables are as defined in the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty first, twenty second, twenty third and/or twenty fourth embodiments. In an alternative embodiment, $R^3$ is isopropyl or oxetanyl. In another alternative embodiment, $R^3$ is isopropyl.

In a twenty sixth embodiment, the application provides a compound according to Structural Formula I, II, III, IV, V, VI, VII, VIII, IX, X, XI, XII, XIII(a), XIII(b), XIV, or a pharmaceutically acceptable salt thereof, in combination with a PARP inhibitor, wherein $R^1$ is tert-butyl; and the variables are as defined in the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty first, twenty second, twenty third, twenty fourth, and/or twenty fifth embodiments.

In a twenty seventh embodiment, the application provides a compound according to Structural Formula III, IV, V, VI, VII, VIII, IX, X, XI, XII, XIII(a), XIII(b), XIV, or a pharmaceutically acceptable salt thereof, in combination with a PARP inhibitor, wherein $R^4$ is

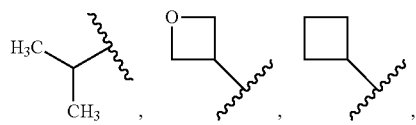

-continued

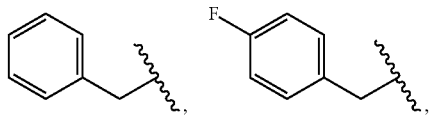

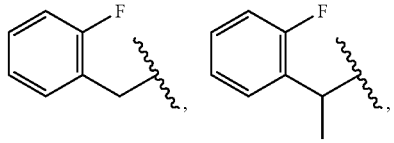

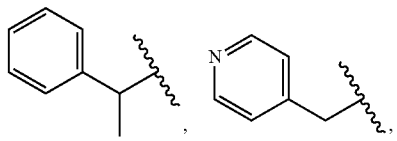

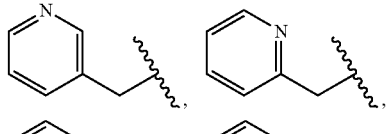

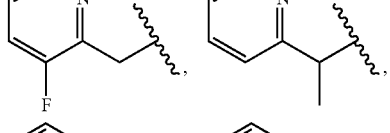

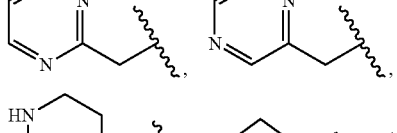

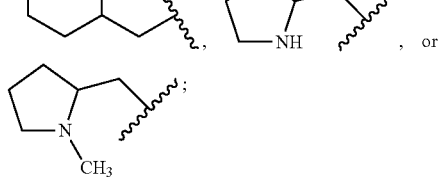

and the variables are as defined in the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty first, twenty second, twenty third, twenty fourth, twenty fifth, and/or twenty sixth embodiments. In an alternative embodiment, $R^4$ is

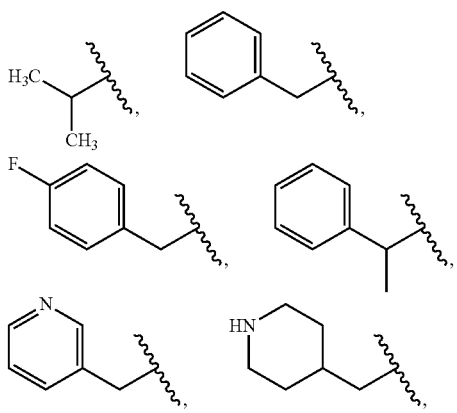

-continued

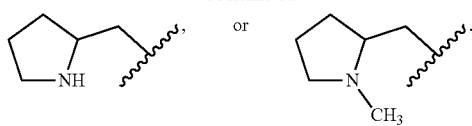

In another alternative embodiment, R⁴ is

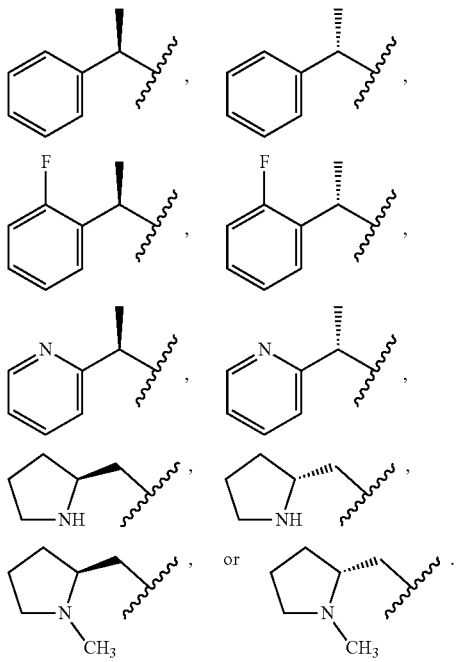

In another alternative embodiment, R⁴ is

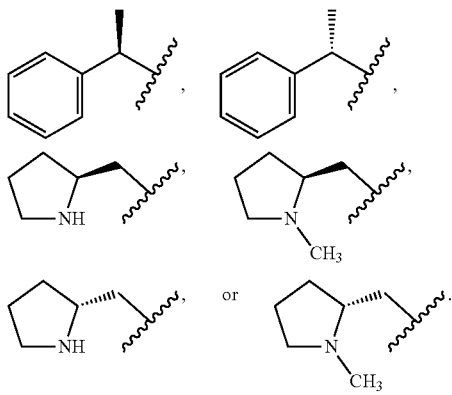

Still in another alternative embodiment, R⁴ is

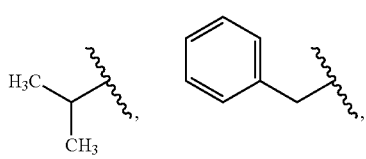

-continued

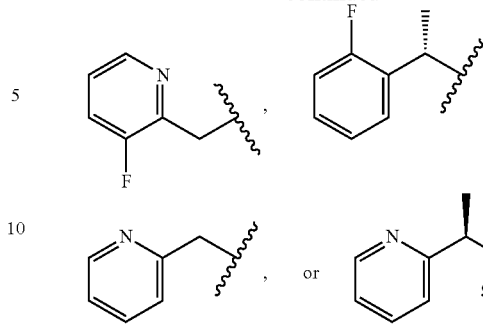

Still in another alternative embodiment, R⁴ is

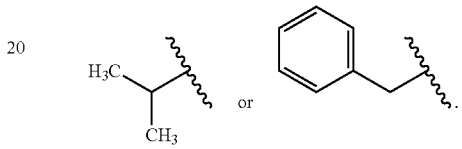

The present application provides a compound represented by Structural Formula I' in combination with a PARP inhibitor.

In a first embodiment, the application provides a compound represented by Structural Formula I' in combination with a PARP inhibitor:

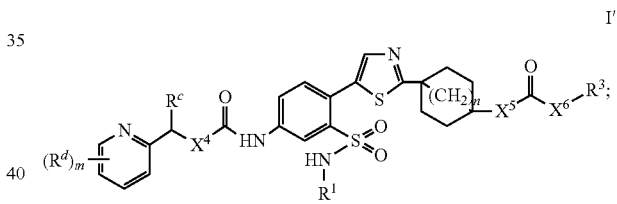

I' or a pharmaceutically acceptable salt thereof, wherein:
the thiazole ring is optionally substituted with —F or —Cl;
X⁴ is NR$^a$ or O;
X⁵ and X⁶ are each independently NR$^b$ or O;
R¹ is (C₁-C₅)alkyl;
R³ is (C₁-C₅)alkyl, —(C₃-C₇)cycloalkyl, or —(CH₂)$_q$heterocyclyl (wherein the heterocyclyl is a monocyclic 3-7-membered heterocyclic ring optionally substituted with one or more occurrences of methyl), or benzyl (wherein the benzyl ring is optionally substituted with one or more occurrences of halogen, methoxy, halomethoxy, methyl, halomethyl, or cyano);
each of R$^a$, R$^b$, and R$^c$ is independently hydrogen or methyl;
R$^d$ is independently halogen, methoxy, halomethoxy, methyl, halomethyl, or cyano;
m is 0, 1, 2, or 3;
n is 0, 1, or 2; and
q is 0 or 1.

In a second embodiment, the application provides a compound represented by Structural Formula I'-1 in combination with a PARP inhibitor:

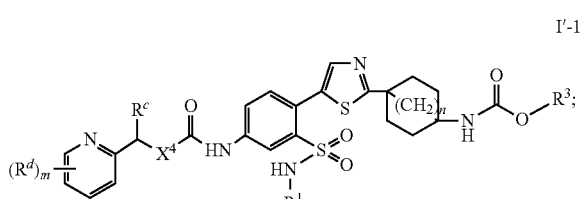

I'-1 or a pharmaceutically acceptable salt thereof, and the variables are as defined in the first embodiment.

In a third embodiment, the application provides a compound represented by Structural Formula I'-2 in combination with a PARP inhibitor:

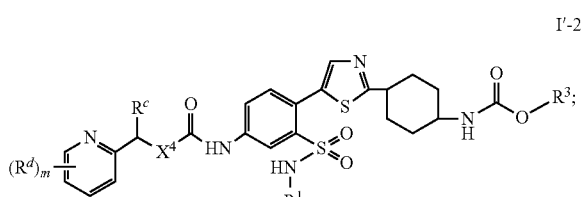

I'-2 or a pharmaceutically acceptable salt thereof, and the variables are as defined in the first embodiment.

In a forth embodiment, the application provides a compound represented by Structural Formula I'-3 in combination with a PARP inhibitor:

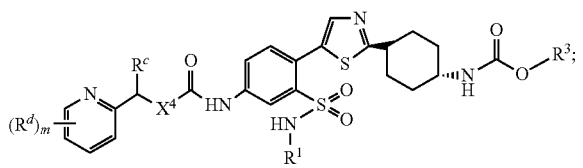

I'-3 or a pharmaceutically acceptable salt thereof, and the variables are as defined in the first embodiment.

In a fifth embodiment, the application provides a compound represented by Structural Formula I'-4 in combination with a PARP inhibitor:

I'-4 or a pharmaceutically acceptable salt thereof, and the variables are as defined in the first embodiment.

In a sixth embodiment, the application provides a compound according to Structural Formula I', I'-1, I'-2, I'-3, or I'-4, or a pharmaceutically acceptable salt thereof, in combination with a PARP inhibitor, wherein $X^4$ is NH, and the remaining variables are as defined in the first embodiment.

In a seventh embodiment, the application provides a compound according to Structural Formula I', I'-1, I'-2, I'-3, or I'-4, or a pharmaceutically acceptable salt thereof, in combination with a PARP inhibitor, wherein $R^3$ is $(C_1-C_4)$ alkyl, $—(C_4-C_6)$cycloalkyl, $—(CH_2)_q$heterocyclyl (wherein the heterocycyl is a monocyclic 4-6-membered heterocyclic ring optionally substituted with one methyl), or benzyl, and the remaining variables are as defined in the first and/or sixth embodiments. In one specific embodiment, $R^3$ is isopropyl, tert-butyl, cyclobutyl, cyclopentyl, oxetanyl, benzyl, tetrahydro-2H-pyranyl, or

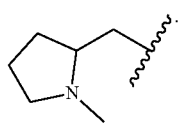

In another specific embodiment, $R^3$ is isopropyl or oxetanyl.

In an eighth embodiment, the application provides a compound according to Structural Formula I', I'-1, I'-2, I'-3, or I'-4, or a pharmaceutically acceptable salt thereof, in combination with a PARP inhibitor, wherein $R^d$ is halogen, and m is 0 or 1, and the remaining variables are as defined in the first, sixth, and/or seventh embodiments. In one specific embodiment,

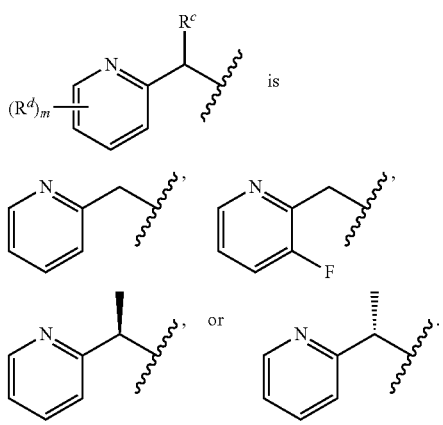

In a ninth embodiment, the application provides a compound according to Structural Formula I', I'-1, I'-2, I'-3, or I'-4, or a pharmaceutically acceptable salt thereof, in combination with a PARP inhibitor, wherein $R^1$ is tert-butyl, and the remaining variables are as defined in the first, sixth, seventh, and/or eighth embodiments.

In a tenth embodiment, the application provides a compound, or a pharmaceutically acceptable salt thereof, in combination with a PARP inhibitor, wherein the compound is selected from the group consisting of:

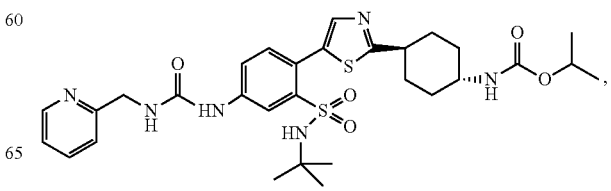

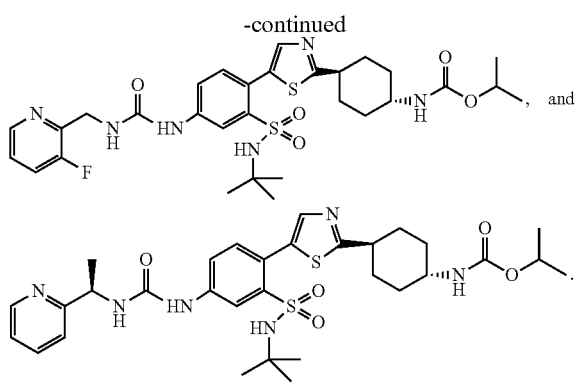

In an eleventh embodiment, the application provides a compound represented by Structural Formula II' in combination with a PARP inhibitor:

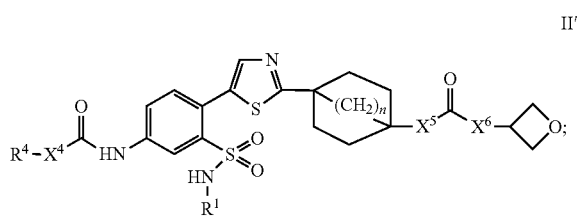

or a pharmaceutically acceptable salt thereof, wherein: the thiazole ring is optionally substituted with —F or —Cl;

$X^4$ is $NR^a$ or O;

$X^5$ and $X^6$ are each independently $NR^b$ or O;

$R^1$ is $(C_1$-$C_5)$alkyl;

$R^4$ is $(C_1$-$C_4)$alkyl, —$(C_3$-$C_7)$cycloalkyl, —$(CH(R^c))_q$-heterocycyl (wherein the heterocycyl is a monocyclic 3-7-membered heterocyclic ring optionally substituted with one or more occurrences of methyl), —$(CH(R^c))_q$-phenyl (wherein the phenyl ring is optionally substituted with one or more occurrences of halogen, methoxy, halomethoxy, methyl, halomethyl, or cyano), or —$(CH(R^c))_q$-2-pyridinyl (wherein the 2-pyridinyl ring is optionally substituted with one or more occurrences of halogen, methoxy, halomethoxy, methyl, halomethyl, or cyano);

each of $R^a$, $R^b$, and $R^c$ is independently hydrogen or methyl;

n is 0, 1, or 2; and q is 0 or 1.

In a twelfth embodiment, the application provides a compound represented by Structural Formula II'-1 in combination with a PARP inhibitor:

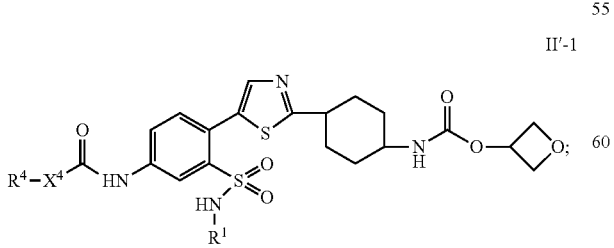

or a pharmaceutically acceptable salt thereof, and the variables are as defined in the eleventh embodiment.

In a thirteenth embodiment, the application provides a compound represented by Structural Formula II'-2 in combination with a PARP inhibitor:

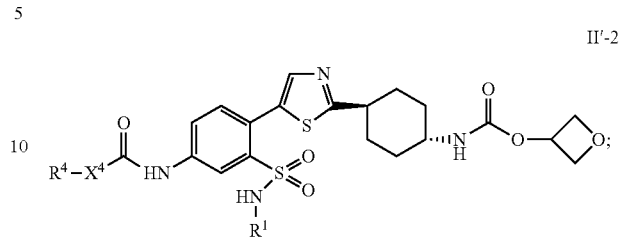

or a pharmaceutically acceptable salt thereof, and the variables are as defined in the eleventh embodiment.

In a fourteenth embodiment, the application provides a compound according to Structural Formula II', II'-1 or II'-2, or a pharmaceutically acceptable salt thereof, in combination with a PARP inhibitor, wherein $R^4$ is isopropyl, oxetanyl, cyclobutyl, —$CH_2$-2-pyrrolidinyl, —$CH_2$—N-methyl-2-pyrrolidinyl, —$CH_2$-3-piperidinyl, —$CH_2$-2-pyrazinyl, —$CH_2$-2-pyrimidinyl, —$CH(R^c)$-phenyl, or —$CH(R^c)$-2-pyridinyl, and that the phenyl and 2-pyridinyl rings are each independently and optionally substituted with one or more occurrences of halogen, and the remaining variables are as defined in the eleventh embodiment. In one specific embodiment, $R^4$ is

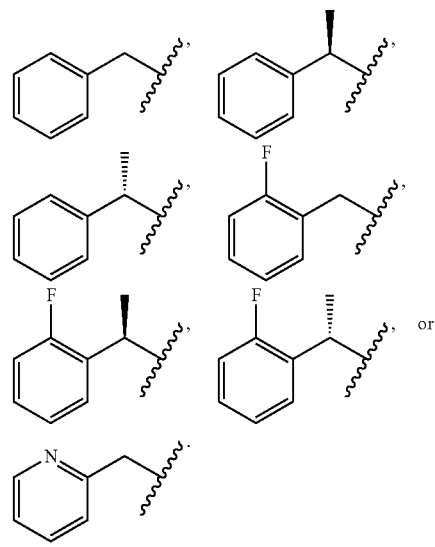

In another specific embodiment, $R^4$ is

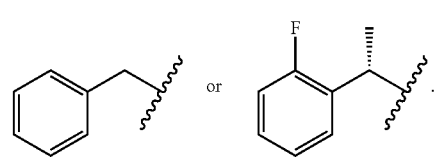

In a fifteenth embodiment, the application provides a compound according to Structural Formula II', II'-1 or II'-2, or a pharmaceutically acceptable salt thereof, in combination with a PARP inhibitor, wherein $X^4$ is NH, and the remaining variables are as defined in the eleventh and/or fourteenth embodiments.

In a sixteenth embodiment, the application provides a compound according to Structural Formula II', II'-1 or II'-2, or a pharmaceutically acceptable salt thereof, in combination with a PARP inhibitor, wherein $R^1$ is tert-butyl, and the remaining variables are as defined in the eleventh, fourteenth, and fifteenth embodiments.

In a seventeenth embodiment, the application provides a compound, or a pharmaceutically acceptable salt thereof, in combination with a PARP inhibitor, wherein the compound is selected from the group consisting of:

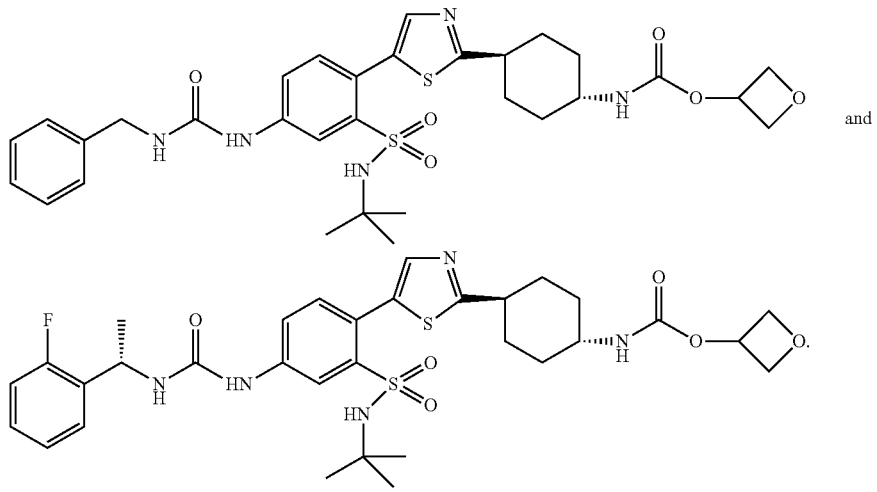

and

In a eighteenth embodiment, the application provides a compound, or a pharmaceutically acceptable salt thereof, in combination with a PARP inhibitor, wherein the compound is:

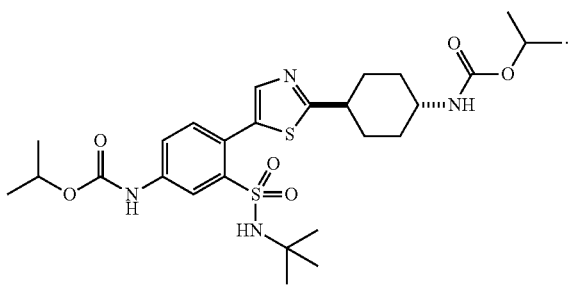

Also included are the compounds disclosed in the Exemplification, both in the pharmaceutically acceptable salt form and in the neutral form, in combination with a PARP inhibitor.

The term "pharmaceutically acceptable salt" refers to a pharmaceutical salt that is, within the scope of sound medical judgment, suitable for use in contact with the tissues of humans and lower animals without undue toxicity, irritation, and allergic response, and is commensurate with a reasonable benefit/risk ratio. Pharmaceutically-acceptable salts are well known in the art. For example, S. M. Berge et al. describes pharmacologically acceptable salts in *J. Pharm. Sci.*, 1977, 66, 1-19.

Included in the present application are pharmaceutically acceptable salts of the compounds disclosed herein. Compounds having basic groups can form pharmaceutically acceptable salts with pharmaceutically acceptable acid(s). Suitable pharmaceutically acceptable acid addition salts of the compounds described herein include salts of inorganic acids (such as hydrochloric acid, hydrobromic, phosphoric, metaphosphoric, nitric, and sulfuric acids) and of organic acids (such as acetic acid, benzenesulfonic, benzoic, ethanesulfonic, methanesulfonic, succinic, and trifluoroacetic acid acids). Compounds of the present application with acidic groups such as carboxylic acids can form pharmaceutically acceptable salts with pharmaceutically acceptable base(s).

Suitable pharmaceutically acceptable basic salts include ammonium salts, alkali metal salts (such as sodium and potassium salts) and alkaline earth metal salts (such as magnesium and calcium salts).

In one aspect, this application provides a combination of a RAD51 inhibitor and a PARP inhibitor. As used herein, a poly ADP ribose polymerase (PARP) is a member of a family of proteins that is involved in a number of cellular processes, such as DNA repair and programmed cell death. A PARP inhibitor (PARPi) reduces the functioning of a poly ADP ribose polymerase. In particular embodiments, the PARP inhibitor is selected from the group consisting of veliparib, BMN-673, 4-iodo-3-nitrobenzamide, olaparib, rucaparib, CEP 9722, niraparib, talazoparib (BMN-673), pamiparib (BGB-290), iniparib (BSI-201, SAR240550), INO-1001, ABT-767, E7016/GPI-21016, AZD2461, AZD2281, AIM-100, and 2X-121.

In some embodiments, the PARP inhibitor is selected from the group consisting of olaparib, veliparib, rucaparib, talazoparib, and niraparib. In some embodiments, the PARP inhibitor is olaparib. In some embodiments, the PARP inhibitor is veliparib. In some embodiments, the PARP inhibitor is rucaparib. In yet some embodiments, the PARP inhibitor is talazoparib. In some embodiments the PARP inhibitor is niraparib.

Definitions

The term "synergistic" as used herein refers to a therapeutic combination which is more effective than the additive effects of the two or more single agents. A determination of a synergistic interaction between the compounds disclosed herein, and one or more PARP inhibitor may be based on the results obtained from the assays described herein.

The combination therapy may provide "synergy" and prove "synergistic", i.e., the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation as separate formulations; or (3) by some other regimen. When delivered in alternation therapy, a synergistic effect may be attained when the compounds are administered or delivered sequentially. In some embodiments, the compound of the present application is administered first. In other embodiments, the PARP inhibitor is administered first. In alternate embodiments, the combination therapy is administered concomitantly as separate compositions. In alternate embodiments, the combination therapy is administered as a single composition.

Combination therapy in which two or more drugs are used together in some dosing regimen or administration form, typically has one or more goals of: (i) reducing the frequency at which acquired resistance arises by combining drugs with minimal cross-resistance, (ii) lowering the doses of drugs with non-overlapping toxicity and similar therapeutic profile so as to achieve efficacy with fewer side effects, i.e., increase therapeutic index, (iii) sensitizing cells to the action of one drug through use of another drug, such as altering cell-cycle stage or growth properties, and (iv) achieving enhanced potency by exploiting additivity, or greater than additivity, effects in the biological activity of two drugs.

As used herein, the term "combination", as applied to two or more compounds and/or agents, is intended to define material in which the two or more agents are associated. The terms "combined" and "combining" in this context are to be interpreted accordingly.

The association of the two or more compounds/agents in a combination may be physical or non-physical. Examples of physically associated combined compounds/agents include: compositions (e.g., unitary formulations) comprising the two or more compounds/agents in admixture (for example within the same unit dose); compositions comprising material in which the two or more compounds/agents are chemically/physicochemically linked (for example by cross-linking, molecular agglomeration or binding to a common vehicle moiety); compositions comprising material in which the two or more compounds/agents are chemically/physicochemically co-packaged (for example, disposed on or within lipid vesicles, particles (e.g. micro- or nanoparticles) or emulsion droplets); pharmaceutical kits, pharmaceutical packs or patient packs in which the two or more compounds/agents are co-packaged or co-presented (e.g. as part of an array of unit doses). Examples of non-physically associated combined compounds/agents include: material (e.g., a non-unitary formulation) comprising at least one of the two or more compounds/agents together with instructions for the extemporaneous association of the at least one compound to form a physical association of the two or more compounds/agents; material (e.g., a non-unitary formulation) comprising at least one of the two or more compounds/agents together with instructions for combination therapy with the two or more compounds/agents; material comprising at least one of the two or more compounds/agents together with instructions for administration to a patient population in which the other(s) of the two or more compounds/agents have been (or are being) administered; material comprising at least one of the two or more compounds/agents in an amount or in a form which is specifically adapted for use in combination with the other(s) of the two or more compounds/agents.

As used herein, the term "combination therapy" is intended to define therapies which comprise the use of a combination of two or more compounds/agents (as defined above). Thus, references to "combination therapy", "combinations" and the use of compounds/agents "in combination" in this application may refer to compounds/agents that are administered as part of the same overall treatment regimen. As such, the dosage regimen of each of the two or more compounds/agents may differ: each may be administered at the same time or at different times. It will therefore be appreciated that the compounds/agents of the combination may be administered sequentially (e.g. before or after) or simultaneously, either in the same pharmaceutical formulation (i.e. together), or in different pharmaceutical formulations (i.e. separately). Simultaneously in the same formulation is as a unitary formulation whereas simultaneously in different pharmaceutical formulations is non-unitary. The dosage of each of the two or more compounds/agents in a combination therapy may also differ with respect to the route of administration.

As used herein, the term "pharmaceutical kit" defines an array of one or more unit doses of a pharmaceutical composition together with dosing means (e.g. measuring device) and/or delivery means (e.g. inhaler or syringe), optionally all contained within common outer packaging. In pharmaceutical kits comprising a combination of two or more compounds/agents, the individual compounds/agents may be unitary or non-unitary formulations. The unit dose(s) may be contained within a blister pack. The pharmaceutical kit may optionally further comprise instructions for use.

As used herein, the term "pharmaceutical pack" defines an array of one or more unit doses of a pharmaceutical composition, optionally contained within common outer packaging. In pharmaceutical packs comprising a combination of two or more compounds/agents, the individual compounds/agents may be unitary or non-unitary formulations. The unit dose(s) may be contained within a blister pack. The pharmaceutical pack may optionally further comprise instructions for use.

In some embodiments, "temporal proximity" means that administration of one therapeutic agent occurs within a time period before or after the administration of another therapeutic agent, such that the therapeutic effect of the one therapeutic agent overlaps with the therapeutic effect of the another therapeutic agent. In some embodiments, the therapeutic effect of the one therapeutic agent completely overlaps with the therapeutic effect of the other therapeutic agent. In some embodiments, "temporal proximity" means that administration of one therapeutic agent occurs within a time period before or after the administration of another therapeutic agent, such that there is a synergistic effect between the one therapeutic agent and the another therapeutic agent. "Temporal proximity" may vary according to various factors, including but not limited to, the age, gender, weight, genetic background, medical condition, disease history, and treatment history of the subject to which the therapeutic agents are to be administered; the disease or condition to be treated or ameliorated; the therapeutic outcome to be achieved; the dosage, dosing frequency, and dosing duration of the therapeutic agents; the pharmacokinetics and pharmacodynamics of the therapeutic agents; and the route(s) through which the therapeutic agents are administered. In some embodiments, "temporal proximity" means within 15 minutes, within 30 minutes, within an hour, within two hours, within four hours, within six hours, within eight hours, within 12 hours, within 18 hours, within 24 hours, within 36 hours, within 2 days, within 3 days, within 4 days, within 5 days, within 6 days, within a week, within 2 weeks, within 3 weeks, within 4 weeks, with 6 weeks, or within 8 weeks. In some embodiments, multiple administration of one therapeutic agent can occur in temporal proximity to a single administration of another therapeutic agent. In some embodiments, temporal proximity may change during a treatment cycle or within a dosing regimen.

The term "halo" as used herein means halogen and includes fluoro, chloro, bromo and iodo.

The term "alkyl" used alone or as part of a larger moiety, such as "alkoxy" or "haloalkyl" and the like, means saturated aliphatic straight-chain or branched monovalent hydrocarbon radical. Unless otherwise specified, an alkyl group typically has 1-5 carbon atoms, i.e. $(C_1$-$C_5)$alkyl. As used herein, a "$(C_1$-$C_5)$alkyl" group means a radical having from 1 to 5 carbon atoms in a linear or branched arrangement. Examples include methyl, ethyl, n-propyl, iso-propyl, and the like.

The term "alkoxy" means an alkyl radical attached through an oxygen linking atom, represented by —O-alkyl. For example, "$(C_1$-$C_4)$alkoxy" includes methoxy, ethoxy, propoxy, and butoxy.

The terms "haloalkyl" and "haloalkoxy" means alkyl or alkoxy, as the case may be, substituted with one or more halogen atoms.

An "alkylene group" is a saturated aliphatic branched or straight-chain divalent hydrocarbon radical. Unless otherwise specified, an alkylene group typically has 2-6 carbon atoms, e.g. $(C_2$-$C_6)$alkylene.

The term "alkenyl" means branched or straight-chain monovalent hydrocarbon radical containing at least one double bond. Alkenyl may be mono or polyunsaturated, and may exist in the E or Z configuration. Unless otherwise specified, an alkenyl group typically has 2-6 carbon atoms, i.e., $(C_2$-$C_6)$alkenyl. For example, "$(C_2$-$C_4)$alkenyl" means a radical having from 2-4 carbon atoms in a linear or branched arrangement.

The term "cycloalkyl" means a monocyclic saturated hydrocarbon ring system. For example, a $C_3$-$C_6$ cycloalkyl includes cyclopropyl, cyclobutyl, cyclopentyl and cyclohexyl. Unless otherwise described, a "cycloalkyl" has from three to seven ring carbon atoms.

A bridged cycloalkyl means a bicyclic non-aromatic hydrocarbon ring system in which the two rings share at least three adjacent ring carbon atoms. A bridged cycloalkyl typically has 6-12 ring carbon atoms. Examples include, but are not limited to, bicyclo[2.1.1]hexyl, bicyclo[2.2.1]heptyl, bicyclo[2.2.2]octyl, bicyclo[3.2.1]octyl, bicyclo[4.3.1] decyl, bicyclo[3.3.1]nonyl, bornyl, bornenyl, norbornyl, norbornenyl, 6,6-dimethylbicyclo [3.1.1]heptyl, tricyclobutyl, and adamantyl.

The terms "heterocyclyl", "heterocyclic ring", and "heterocyclic group", are used interchangeably herein, and means a saturated or unsaturated non-aromatic 4-10 membered ring radical containing from 1 to 4 ring heteroatoms, which may be the same or different, selected from N, O, or S. It can be monocyclic, bicyclic or tricyclic (e.g., a fused or bridged bicyclic or tricyclic ring). Examples of include, but are not limited to, azetidinyl, morpholinyl, thiomorpholinyl, pyrrolidinonyl, pyrrolidinyl, piperidinyl, piperazinyl, hydantoinyl, valerolactamyl, oxiranyl, oxetanyl, dihydroimidazole, dihydrofuranyl, dihydropyranyl, dihydropyridinyl, dihydropyrimidinyl, dihydrothiophenyl, dihydrothiopyranyl, tetrahydroimidazole, tetrahydrofuranyl, tetrahydropyranyl, tetrahydrothienyl, tetrahydropyridinyl, tetrahydropyrimidinyl, tetrahydrothiophenyl, and tetrahydrothiopyranyl. A heterocyclic ring optionally contains one or more double bonds and/or is optionally fused with one or more aromatic rings (for example, tetrahydronaphthyridine, indolinone, dihydropyrrolotriazole, imidazopyrimidine, quinolinone, dioxaspirodecane).

Examples of 3-7 membered monocyclic heterocyclic ring include, but are not limited to, azetidinyl, morpholinyl, thiomorpholinyl, pyrrolidinonyl, pyrrolidinyl, piperidinyl, piperazinyl, hydantoinyl, valerolactamyl, oxiranyl, oxetanyl, dihydroimidazole, dihydrofuranyl, dihydropyranyl, dihydropyridinyl, dihydropyrimidinyl, dihydrothienyl, dihydrothiophenyl, dihydrothiopyranyl, tetrahydroimidazole, tetrahydrofuranyl, tetrahydropyranyl, tetrahydrothienyl, tetrahydropyridinyl, tetrahydropyrimidinyl, tetrahydrothiophenyl, and tetrahydrothiopyranyl.

A bridged heterocyclyl means a bicyclic non-aromatic ring system containing from 1 to 4 ring heteroatoms in which the two rings share at least three adjacent ring atoms. A bridged heterocyclyl typically has 6-12 ring atoms. Examples include, but are not limited to, azanorbornyl, quinuclidinyl, isoquinuclidinyl, tropanyl, azabicyclo[3.2.1] octanyl, azabicyclo[2.2.1]heptany1, 2-azabicyclo[3.2.1]octanyl, azabicyclo[3.2.1]octanyl, azabicyclo[3.2.2]nonanyl, azabicyclo[3.3.0]nonanyl, and azabicyclo [3.3.1]nonanyl.

The terms "heteroaryl", "heteroaromatic", "heteroaryl ring", "heteroaryl group", "heteroaromatic ring", and "heteroaromatic group", are used interchangeably herein. "Heteroaryl" when used alone or as part of a larger moiety as in "heteroaralkyl" or "heteroarylalkoxy", refers to aromatic ring groups having five to ten ring atoms selected from carbon and at least one (typically 1 to 4, more typically 1 or 2) heteroatoms (e.g., oxygen, nitrogen or sulfur). "Heteroaryl" includes monocyclic rings and polycyclic rings in which a monocyclic heteroaromatic ring is fused to one or more other aromatic or heteroaromatic rings. "Heteroaryl" includes monocyclic and bicyclic ring systems.

"Monocyclic 5-6 membered heteroaromatic ring (or heteroaryl)" means a monocyclic heteroaromatic ring having five or six ring atoms selected from carbon and at least one (typically 1 to 3, more typically 1 or 2) heteroatoms (e.g., oxygen, nitrogen or sulfur). Examples of monocyclic 5-6 membered heteroaromatic ring groups include furanyl (e.g., 2-furanyl, 3-furanyl), imidazolyl (e.g., N-imidazolyl, 2-imidazolyl, 4-imidazolyl, 5-imidazolyl), isoxazolyl (e.g., 3-isoxazolyl, 4-isoxazolyl, 5-isoxazolyl), oxadiazolyl (e.g., 2-oxadiazolyl, 5-oxadiazolyl), oxazolyl (e.g., 2-oxazolyl, 4-oxazolyl, 5-oxazolyl), pyrazolyl (e.g., 3-pyrazolyl, 4-pyrazolyl), pyrrolyl (e.g., 1-pyrrolyl, 2-pyrrolyl, 3-pyrrolyl), pyridyl (e.g., 2-pyridyl, 3-pyridyl, 4-pyridyl), pyrimidinyl (e.g., 2-pyrimidinyl, 4-pyrimidinyl, 5-pyrimidinyl), pyridazinyl (e.g., 3-pyridazinyl), thiazolyl (e.g., 2-thiazolyl, 4-thiazolyl, 5-thiazolyl), isothiazolyl, triazolyl (e.g., 2-triazolyl, 5-triazolyl), tetrazolyl (e.g., tetrazolyl), and thienyl (e.g., 2-thienyl, 3-thienyl).

If a group is described as being "substituted," a non-hydrogen substituent replaces a hydrogen on a carbon or nitrogen of the substituent. Thus, for example, a substituted alkyl is an alkyl wherein at least one non-hydrogen substituent is in the place of a hydrogen substituent on the alkyl substituent. To illustrate, monofluoroalkyl is alkyl substituted with a fluoro substituent, and difluoroalkyl is alkyl substituted with two fluoro substituents. It should be recognized that if there is more than one substitution on a substituent, each non-hydrogen substituent can be identical or different (unless otherwise stated). As used herein, many moieties (e.g., alkyl, cycloalkyl, or a heterocyclic ring) are referred to as being either "substituted" or "optionally substituted". When a moiety is modified by one of these terms, unless otherwise noted, it denotes that any portion of the moiety that is known to one skilled in the art as being available for substitution can be substituted, which includes one or more substituents. If more than one substituent is present, then each substituent is independently selected. Such means for substitution are well-known in the art and/or taught by the instant application. The optional substituents can be any substituents that are suitable to attach to the moiety. A person of ordinary skill in the art will recognize that the compounds and definitions provided do not include impermissible substituent patterns (e.g., methyl substituted with 5 different groups, and the like). Such impermissible substitution patterns are clearly recognized by a person of ordinary skill in the art. When a group is described as being optionally substituted by "one or more" substituents, it denotes that the group is optionally substituted by one, two, three, four, five or six substituents. In one embodiment, a group is optionally substituted by 1-3 substituents. In one embodiment, a group is optionally substituted by 1-2 substituents. In one embodiment, a group is optionally substituted by one substituent.

Suitable substituents are those which do not have a significant adverse effect on the ability of the compound to inhibit RAD51. Where suitable substituents are not specifically enumerated, exemplary substituents include, but are not limited to, halo, —CN, alkyl, alkoxy, halomethyl, halomethoxy, $(C_1-C_5)$alkyl, halo$(C_1-C_5)$alkyl, $(C_1-C_5)$alkoxy, —NO$_2$, —OR$^{c'}$, —NR$^{a'}$R$^{b'}$, —S(O)$_i$R$^{a'}$, —NR$^{a'}$S(O)$_i$ R$^{b'}$, —S(O)$_i$NR$^{a'}$R$^{b'}$, —C(=O)OR$^{a'}$, —OC(=O)OR$^{a'}$, —C(=S)OR$^{a'}$, —O(C=S)R$^{a'}$, —C(=O)NR$^{a'}$R$^{b'}$, —NR$^{a'}$C(=O)R$^{b'}$, —C(=S)NR$^{a'}$R$^{b'}$, —NR$^{a'}$C(=S)R$^{b'}$, —NR$^{a'}$(C=O)OR$^{b'}$, —O(C=O)NR$^{a'}$R$^{b'}$, —NR$^{a'}$(C=S)OR$^{b'}$, —O(C=S)NR$^{a'}$R$^{b'}$, —NR$^{a'}$(C=O)NR$^{a'}$R$^{b'}$, —NR$^{a'}$(C=S)NR$^{a'}$R$^{b'}$, —C(=S)R$^{a'}$, —C(=O)R$^{a'}$, $(C_3-C_6)$cycloalkyl, monocyclic heteroaryl and phenyl, wherein the $(C_3-C_6)$cycloalkyl, monocyclic heteroaryl and phenyl substituents are optionally and independently substituted with —CH$_3$, halomethyl, halo, methoxy or halomethoxy. Each R$^{a'}$ and each R$^{b'}$ are independently selected from —H and $(C_1-C_5)$alkyl, wherein the $(C_1-C_5)$alkyl group represented by R$^{a'}$ or R$^{b'}$ is optionally substituted with hydroxyl or $(C_1-C_3)$alkoxy; R$^{c'}$ is —H, halo$(C_1-C_5)$alkyl or $(C_1-C_5)$alkyl, wherein the $(C_1-C_5)$alkyl group represented by R$^c$ is optionally substituted with hydroxyl or $(C_1-C_3)$alkoxy; and i is 0, 1, or 2. =O is also a suitable substituent for alkyl, cycloalkyl, and a heterocyclic ring.

Compounds having one or more chiral centers can exist in various stereoisomeric forms. Stereoisomers are compounds that differ only in their spatial arrangement. Stereoisomers include all diastereomeric, enantiomeric, and epimeric forms as well as racemates and mixtures thereof.

The term "geometric isomer" refers to cyclic compounds having at least two substituents, wherein the two substituents are both on the same side of the ring (cis) or wherein the substituents are each on opposite sides of the ring (trans). When a disclosed compound is named or depicted by structure without indicating stereochemistry, it is understood that the name or the structure encompasses one or more of the possible stereoisomers, or geometric isomers, or a mixture of the encompassed stereoisomers or geometric isomers.

When a geometric isomer is depicted by name or structure, it is to be understood that the named or depicted isomer exists to a greater degree than another isomer, that is that the geometric isomeric purity of the named or depicted geometric isomer is greater than 50%, such as at least 60%, 70%, 80%, 90%, 99%, or 99.9% pure by weight. Geometric isomeric purity is determined by dividing the weight of the named or depicted geometric isomer in the mixture by the total weight of all of the geometric isomers in the mixture.

Racemic mixture means 50% of one enantiomer and 50% of is corresponding enantiomer. When a compound with one chiral center is named or depicted without indicating the stereochemistry of the chiral center, it is understood that the name or structure encompasses both possible enantiomeric forms (e.g., both enantiomerically-pure, enantiomerically-enriched or racemic) of the compound. When a compound with two or more chiral centers is named or depicted without indicating the stereochemistry of the chiral centers, it is understood that the name or structure encompasses all possible diastereomeric forms (e.g., diastereomerically pure, diastereomerically enriched and equimolar mixtures of one or more diastereomers (e.g., racemic mixtures) of the compound.

Enantiomeric and diastereomeric mixtures can be resolved into their component enantiomers or stereoisomers by well-known methods, such as chiral-phase gas chromatography, chiral-phase high performance liquid chromatography, crystallizing the compound as a chiral salt complex, or crystallizing the compound in a chiral solvent. Enantiomers and diastereomers also can be obtained from diastereomerically- or enantiomerically-pure intermediates, reagents, and catalysts by well-known asymmetric synthetic methods.

When a compound is designated by a name or structure that indicates a single enantiomer, unless indicated otherwise, the compound is at least 60%, 70%, 80%, 90%, 99% or 99.9% optically pure (also referred to as "enantiomerically pure"). Optical purity is the weight in the mixture of the named or depicted enantiomer divided by the total weight in the mixture of both enantiomers.

When the stereochemistry of a disclosed compound is named or depicted by structure, and the named or depicted structure encompasses more than one stereoisomer (e.g., as in a diastereomeric pair), it is to be understood that one of the encompassed stereoisomers or any mixture of the encompassed stereoisomers is included. It is to be further understood that the stereoisomeric purity of the named or depicted stereoisomers at least 60%, 70%, 80%, 90%, 99% or 99.9% by weight. The stereoisomeric purity in this case is determined by dividing the total weight in the mixture of the stereoisomers encompassed by the name or structure by the total weight in the mixture of all of the stereoisomers.

Pharmaceutical Compositions

The compounds disclosed therein are RAD51 inhibitors. The pharmaceutical composition of the present application comprises one or more RAD51 inhibitors, or a pharmaceutically acceptable salt thereof, and one or more PARP inhibitors, or a pharmaceutically acceptable salt thereof, and a pharmaceutically acceptable carrier or diluent.

"Pharmaceutically acceptable carrier" and "pharmaceutically acceptable diluent" refer to a substance that aids the formulation and/or administration of an active agent to and/or absorption by a subject and can be included in the compositions of the present application without causing a significant adverse toxicological effect on the subject. Non-limiting examples of pharmaceutically acceptable carriers and/or diluents include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with or interfere with the activity of the compounds provided herein and PARP inhibitors. One of ordinary skill in the art will recognize that other pharmaceutical excipients are suitable for use with disclosed compounds and PARP inhibitors.

The pharmaceutical compositions of the present application optionally include one or more pharmaceutically acceptable carriers and/or diluents therefor, such as lactose, starch, cellulose and dextrose. Other excipients, such as flavoring agents; sweeteners; and preservatives, such as methyl, ethyl, propyl and butyl parabens, can also be included. More complete listings of suitable excipients can be found in the Handbook of Pharmaceutical Excipients (5$^{th}$ Ed., Pharmaceutical Press (2005)). A person skilled in the art would know how to prepare formulations suitable for various types of administration routes. Conventional procedures and ingredients for the selection and preparation of suitable formulations are described, for example, in Remington's Pharmaceutical Sciences (2003-20th edition) and in The United States Pharmacopeia: The National Formulary (USP 24 NF19) published in 1999. The carriers, diluents and/or excipients are "acceptable" in the sense of being compatible with the other ingredients of the pharmaceutical composition and not deleterious to the recipient thereof.

A "pharmaceutical composition" contains the compound of the present application and a PARP inhibitor in a form suitable for administration to a subject. In one embodiment, the pharmaceutical composition is in bulk or in unit dosage form. The unit dosage form is any of a variety of forms, including, for example, a capsule, an IV bag, a tablet, a single pump on an aerosol inhaler or a vial. The quantity of active ingredient (e.g., a formulation of the disclosed compound or a pharmaceutically acceptable salt thereof and a formulation of a PARP inhibitor or a pharmaceutically acceptable salt thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this application and a PARP inhibitor include powders, sprays, ointments, pastes, creams, lotions, gels, solutions, patches and inhalants. In one embodiment, the active compound and the PARP inhibitor is mixed under sterile conditions with a pharmaceutically acceptable carrier, and with any preservatives, buffers or propellants that are required.

As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable carrier" and "pharmaceutically acceptable diluent" refer to a substance that aids the formulation and/or administration of an active agent to and/or absorption by a subject and can be included in the compositions of the present application without causing a significant adverse toxicological effect on the subject. Non-limiting examples of pharmaceutically acceptable carriers and/or diluents include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with or interfere with the activity of the compounds and PARP inhibitors provided herein. One of ordinary skill in the art will recognize that other pharmaceutical excipients are suitable for use with disclosed compounds and PARP inhibitors.

The term "carrier", as used in this application, encompasses carriers, excipients, and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body of a subject.

The pharmaceutical compositions of the present application optionally include one or more pharmaceutically acceptable carriers and/or diluents therefor, such as lactose, starch, cellulose and dextrose. Other excipients, such as flavoring agents; sweeteners; and preservatives, such as methyl, ethyl, propyl and butyl parabens, can also be included. More complete listings of suitable excipients can be found in the Handbook of Pharmaceutical Excipients (5$^{th}$ Ed., Pharmaceutical Press (2005)). A person skilled in the art would know how to prepare formulations suitable for various types of administration routes. Conventional procedures and ingredients for the selection and preparation of suitable formulations are described, for example, in Remington's Pharmaceutical Sciences (2003-20th edition) and in The United States Pharmacopeia: The National Formulary (USP 24 NF19) published in 1999. The carriers, diluents and/or excipients are "acceptable" in the sense of being compatible with the other ingredients of the pharmaceutical composition and not deleterious to the recipient thereof.

Pharmaceutical compositions of the application are formulated to be compatible with its intended route of administration. Examples of routes of administration include parenteral, e.g., intravenous, intradermal, subcutaneous, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

A compound or pharmaceutical composition can be administered to a subject in many of the well-known methods currently used for chemotherapeutic treatment. For example, for treatment of cancers, a compound may be injected directly into tumors, injected into the blood stream or body cavities or taken orally or applied through the skin with patches. The dose chosen should be sufficient to constitute effective treatment but not as high as to cause unacceptable side effects. The state of the disease condition (e.g., cancer, precancer, and the like) and the health of the patient should preferably be closely monitored during and for a reasonable period after treatment.

The term "therapeutically effective amount", as used herein, refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician.

For any compound, the therapeutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

The pharmaceutical compositions containing active compound of the present application or PARP inhibitors may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of the active compound or PARP inhibitors into preparations that can be used pharmaceutically. Of course, the appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compound is delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compound is formulated into ointments, salves, gels, or creams as generally known in the art.

The active compound can be prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the application are dictated by and directly dependent on the unique characteristics of the active compound and the particular therapeutic effect to be achieved.

In therapeutic applications, the dosages of the pharmaceutical compositions used in accordance with the application vary depending on the agent, the age, weight, and clinical condition of the recipient patient, and the experience and judgment of the clinician or practitioner administering the therapy, among other factors affecting the selected dosage. Generally, the dose should be sufficient to result in slowing, and preferably regressing, the growth of the tumors and also preferably causing complete regression of the cancer. Dosages can range from about 0.01 mg/kg per day to about 5000 mg/kg per day. An effective amount of a pharmaceutical agent is that which provides an objectively identifiable improvement as noted by the clinician or other qualified observer. For example, regression of a tumor in a subject may be measured with reference to the diameter of a tumor. Decrease in the diameter of a tumor indicates regression. Regression is also indicated by failure of tumors to reoccur after treatment has stopped. As used herein, the term "dosage effective manner" refers to amount of an active compound to produce the desired biological effect in a subject or cell.

The pharmaceutical compositions can be included in a container, pack, or dispenser together with instructions for administration.

The dosage regimen utilizing the compound is selected in accordance with a variety of factors including type, species, age, weight, sex and medical condition of the patient; the severity of the condition to be treated; the route of administration; the renal and hepatic function of the patient; and the particular compound or pharmaceutically acceptable salt or solvate thereof employed. An ordinarily skilled physician or veterinarian can readily determine and prescribe the effective amount of the drug required to prevent, counter or arrest the progress of the condition.

Techniques for formulation and administration of the disclosed compound of the application and PARP inhibitors and combinations thereof can be found in *Remington: the Science and Practice of Pharmacy*, 19$^{th}$ edition, Mack Publishing Co., Easton, Pa. (1995). In an embodiment, the compound described herein, and the pharmaceutically acceptable salts or solvates thereof, and a PARP inhibitor, or a pharmaceutically acceptable salt thereof, or a pharmaceutical composition thereof, are used in pharmaceutical preparations in combination with a pharmaceutically acceptable carrier or diluent. Suitable pharmaceutically acceptable carriers include inert solid fillers or diluents and sterile aqueous or organic solutions. The compound or pharmaceutically acceptable salts thereof and the PARP inhibitor or a pharmaceutically acceptable salt thereof will be present in such pharmaceutical compositions in amounts sufficient to provide the desired dosage amount in the range described herein.

All percentages and ratios used herein, unless otherwise indicated, are by weight. Other features and advantages of the present application are apparent from the different examples. The provided examples illustrate different components and methodology useful in practicing the present application. The examples do not limit the claimed application. Based on the present application the skilled artisan can identify and employ other components and methodology useful for practicing the present application.

Methods of Using the Combinations

In some embodiments, the present application provides a method of treating a disease or disorder, wherein the method comprises administering to a subject in need thereof a therapeutically effective amount of a compound described herein.

In some embodiments, the present application provides a method of treating a disease or disorder, wherein the method comprises administering to a subject in need thereof a composition comprising a RAD51 inhibitor, or a pharmaceutically acceptable salt thereof, and a PARP inhibitor, or a pharmaceutically acceptable salt thereof.

In some embodiments, the present application provides a method of treating a disease or disorder, wherein the method comprises administering to a subject in need thereof a combination of a compound of the present disclosure, or a pharmaceutically acceptable salt thereof, and a PARP inhibitor, or a pharmaceutically acceptable salt thereof.

The present application provides a method of treating a cancer, an autoimmune disease, an immune deficiency, or a neurodegenerative disease. In some embodiments, the method comprises administering to a subject in need thereof a therapeutically effective amount of a RAD51 inhibitor or a pharmaceutically acceptable salt thereof or a pharmaceutical composition disclosed herein. In some embodiments, the method comprises administering to a subject in need thereof a therapeutically effective amount of a compound disclosed herein or a pharmaceutically acceptable salt thereof or a pharmaceutical composition disclosed herein.

In one aspect, the present application provides a method of treating a subject with a disease which can be ameliorated by inhibition of RAD51 and/or PARP, by administering to the subject a therapeutically effective amount of one or more disclosed compounds, or a pharmaceutically acceptable salt thereof, or the corresponding pharmaceutical composition, in combination with a PARP inhibitor, or a pharmaceutically acceptable salt thereof, or a pharmaceutical composition thereof. Diseases which can be ameliorated by inhibition of RAD51 and/or PARP include treating cancer, autoimmune disease, immune deficiency, or neurodegenerative disease.

In one aspect, described herein is a method of treating cancer, autoimmune disease, immune deficiency, or neurodegenerative disease, the method comprising administering a therapeutically effective dose of a compound of disclosed herein or a pharmaceutically acceptable salt thereof or a pharmaceutical composition disclosed herein in combination with a PARP inhibitor or a pharmaceutically acceptable salt thereof or a pharmaceutical composition comprising a PARP inhibitor, to a subject in need of treatment for cancer, autoimmune disease, immune deficiency, or neurodegenerative disease.

In some embodiments, the present application provides a method of treating a cancer, an autoimmune disease, an immune deficiency, or a neurodegenerative disease, wherein the method comprises administering to a subject in need thereof a therapeutically effective amount of a compound disclosed herein or a pharmaceutically acceptable salt thereof or a pharmaceutical composition disclosed herein in combination with a PARP inhibitor or a pharmaceutically acceptable salt thereof or a pharmaceutical composition comprising a PARP inhibitor.

In some embodiments, the present application provides a method of treating a cancer, an autoimmune disease, an immune deficiency, or a neurodegenerative disease, wherein the method comprises administering to a subject in need thereof a composition comprising a compound disclosed herein, or a pharmaceutically acceptable salt thereof, and a PARP inhibitor, or a pharmaceutically acceptable salt thereof.

In some embodiments, the present application provides a method of treating a cancer, an autoimmune disease, an immune deficiency, or a neurodegenerative disease, wherein the method comprises administering to a subject in need thereof a combination of a compound disclosed herein, or a pharmaceutically acceptable salt thereof, and a PARP inhibitor, or a pharmaceutically acceptable salt thereof.

In some embodiments, the present application provides a method of treating a cancer, an autoimmune disease, an immune deficiency, or a neurodegenerative disease, wherein the method comprises administering to a subject in need thereof a therapeutically effective amount of a RAD51 inhibitor or a pharmaceutically acceptable salt thereof or a pharmaceutical composition disclosed herein in combination with a PARP inhibitor or a pharmaceutically acceptable salt thereof or a pharmaceutical composition comprising a PARP inhibitor.

In some embodiments, the present application provides a method of treating a cancer, an autoimmune disease, an immune deficiency, or a neurodegenerative disease, wherein the method comprises administering to a subject in need thereof a composition comprising a RAD51 inhibitor, or a pharmaceutically acceptable salt thereof, and a PARP inhibitor, or a pharmaceutically acceptable salt thereof.

In some embodiments, the present application provides a method of treating a cancer, an autoimmune disease, an immune deficiency, or a neurodegenerative disease, wherein the method comprises administering to a subject in need thereof a combination of a RAD51 inhibitor, or a pharmaceutically acceptable salt thereof, and a PARP inhibitor, or a pharmaceutically acceptable salt thereof.

In some embodiments, the present application provides a method of treating a cancer, an autoimmune disease, an immune deficiency, or a neurodegenerative disease, wherein the method comprises administering to a subject in need thereof a therapeutically effective amount of Compound 67A or a pharmaceutically acceptable salt thereof or a pharmaceutical composition disclosed herein in combination with a PARP inhibitor or a pharmaceutically acceptable salt thereof or a pharmaceutical composition comprising a PARP inhibitor.

In some embodiments, the present application provides a method of treating a cancer, an autoimmune disease, an immune deficiency, or a neurodegenerative disease, wherein the method comprises administering to a subject in need thereof a composition comprising Compound 67A, or a pharmaceutically acceptable salt thereof, and a PARP inhibitor, or a pharmaceutically acceptable salt thereof.

In some embodiments, the present application provides a method of treating a cancer, an autoimmune disease, an immune deficiency, or a neurodegenerative disease, wherein the method comprises administering to a subject in need thereof a combination of Compound 67A, or a pharmaceutically acceptable salt thereof, and a PARP inhibitor, or a pharmaceutically acceptable salt thereof.

In some embodiments, the present application provides a method of treating a cancer, an autoimmune disease, an immune deficiency, or a neurodegenerative disease, wherein the method comprises administering to a subject in need thereof a therapeutically effective amount of a compound of the present disclosure or a pharmaceutically acceptable salt thereof or a pharmaceutical composition disclosed herein in combination with olaparib or a pharmaceutically acceptable salt thereof or a pharmaceutical composition comprising olaparib.

In some embodiments, the present application provides a method of treating a cancer, an autoimmune disease, an immune deficiency, or a neurodegenerative disease, wherein the method comprises administering to a subject in need thereof a composition comprising a RAD51 inhibitor, or a pharmaceutically acceptable salt thereof, and olaparib, or a pharmaceutically acceptable salt thereof.

In some embodiments, the present application provides a method of treating a cancer, an autoimmune disease, an immune deficiency, or a neurodegenerative disease, wherein the method comprises administering to a subject in need thereof a combination of a RAD51 inhibitor, or a pharmaceutically acceptable salt thereof, and olaparib, or a pharmaceutically acceptable salt thereof.

In some embodiments, the present application provides a method of treating a cancer, an autoimmune disease, an immune deficiency, or a neurodegenerative disease, wherein the method comprises administering to a subject in need thereof a therapeutically effective amount of Compound 67A or a pharmaceutically acceptable salt thereof or a pharmaceutical composition disclosed herein in combination with olaparib or a pharmaceutically acceptable salt thereof or a pharmaceutical composition comprising olaparib.

In some embodiments, the present application provides a method of treating a cancer, an autoimmune disease, an immune deficiency, or a neurodegenerative disease, wherein the method comprises administering to a subject in need thereof a composition comprising Compound 67A, or a pharmaceutically acceptable salt thereof, and olaparib, or a pharmaceutically acceptable salt thereof.

In some embodiments, the present application provides a method of treating a cancer, an autoimmune disease, an immune deficiency, or a neurodegenerative disease, wherein the method comprises administering to a subject in need thereof a combination of Compound 67A, or a pharmaceutically acceptable salt thereof, and olaparib, or a pharmaceutically acceptable salt thereof.

In some embodiments, the present application provides the use of a compound disclosed herein, or a pharmaceutically acceptable salt thereof, or a pharmaceutical composition disclosed herein in the manufacture of a medicament for the treatment of a disease or disorder.

In some embodiments, the present application provides the use of a composition disclosed herein in the manufacture of a medicament for the treatment of a disease or disorder.

In some embodiments, the present application provides the use of a combination disclosed herein in the manufacture of a medicament for the treatment of a disease or disorder.

In some embodiments, the present application provides the use of a compound disclosed herein, or a pharmaceutically acceptable salt thereof, or a pharmaceutical composition disclosed herein in the manufacture of a medicament for the treatment of a cancer, an autoimmune disease, an immune deficiency, or a neurodegenerative disease.

In some embodiments, the present application provides use of a compound disclosed herein, or a pharmaceutically acceptable salt thereof, or a pharmaceutical composition disclosed herein in combination with a PARP inhibitor, or a pharmaceutically acceptable salt thereof, or a pharmaceutical composition thereof in the manufacture of a medicament for the treatment of a cancer, an autoimmune disease, an immune deficiency, or a neurodegenerative disease.

In some embodiments, the present application provides use of a combination of a compound disclosed herein, or a pharmaceutically acceptable salt thereof, and a PARP inhibitor, or a pharmaceutically acceptable salt thereof in the manufacture of a medicament for the treatment of a cancer, an autoimmune disease, an immune deficiency, or a neurodegenerative disease.

In some embodiments, the present application provides use of a composition comprising a compound disclosed herein, or a pharmaceutically acceptable salt thereof, and a PARP inhibitor, or a pharmaceutically acceptable salt thereof in the manufacture of a medicament for the treatment of a cancer, an autoimmune disease, an immune deficiency, or a neurodegenerative disease.

In some embodiments, the present application provides use of a RAD51 inhibitor, or a pharmaceutically acceptable salt thereof, or a pharmaceutical composition disclosed herein in combination with a PARP inhibitor, or a pharmaceutically acceptable salt thereof, or a pharmaceutical composition thereof in the manufacture of a medicament for the treatment of a cancer, an autoimmune disease, an immune deficiency, or a neurodegenerative disease.

In some embodiments, the present application provides use of a combination of a RAD51 inhibitor, or a pharmaceutically acceptable salt thereof, and a PARP inhibitor, or a pharmaceutically acceptable salt thereof in the manufacture of a medicament for the treatment of a cancer, an autoimmune disease, an immune deficiency, or a neurodegenerative disease.

In some embodiments, the present application provides use of a composition comprising a RAD51 inhibitor, or a pharmaceutically acceptable salt thereof, and a PARP inhibitor, or a pharmaceutically acceptable salt thereof in the manufacture of a medicament for the treatment of a cancer, an autoimmune disease, an immune deficiency, or a neurodegenerative disease.

In some embodiments, the present application provides use of Compound 67A, or a pharmaceutically acceptable salt thereof, or a pharmaceutical composition disclosed herein in combination with a PARP inhibitor, or a pharmaceutically acceptable salt thereof, or a pharmaceutical composition thereof in the manufacture of a medicament for the treatment of a cancer, an autoimmune disease, an immune deficiency, or a neurodegenerative disease.

In some embodiments, the present application provides use of a combination of Compound 67A, or a pharmaceutically acceptable salt thereof, and a PARP inhibitor, or a pharmaceutically acceptable salt thereof in the manufacture of a medicament for the treatment of a cancer, an autoimmune disease, an immune deficiency, or a neurodegenerative disease.

In some embodiments, the present application provides use of a composition comprising Compound 67A, or a pharmaceutically acceptable salt thereof, and a PARP inhibitor, or a pharmaceutically acceptable salt thereof in the manufacture of a medicament for the treatment of a cancer, an autoimmune disease, an immune deficiency, or a neurodegenerative disease.

In some embodiments, the present application provides use of a compound disclosed herein, or a pharmaceutically acceptable salt thereof, or a pharmaceutical composition disclosed herein in combination with olaparib, or a pharmaceutically acceptable salt thereof, or a pharmaceutical composition thereof in the manufacture of a medicament for the treatment of a cancer, an autoimmune disease, an immune deficiency, or a neurodegenerative disease.

In some embodiments, the present application provides use of a combination of a compound disclosed herein, or a pharmaceutically acceptable salt thereof, and olaparib, or a pharmaceutically acceptable salt thereof in the manufacture of a medicament for the treatment of a cancer, an autoimmune disease, an immune deficiency, or a neurodegenerative disease.

In some embodiments, the present application provides use of a composition comprising a compound disclosed herein, or a pharmaceutically acceptable salt thereof, and olaparib, or a pharmaceutically acceptable salt thereof in the manufacture of a medicament for the treatment of a cancer, an autoimmune disease, an immune deficiency, or a neurodegenerative disease.

In some embodiments, the present application provides use of a RAD51 inhibitor, or a pharmaceutically acceptable salt thereof, or a pharmaceutical composition disclosed herein in combination with olaparib, or a pharmaceutically acceptable salt thereof, or a pharmaceutical composition thereof in the manufacture of a medicament for the treatment of a cancer, an autoimmune disease, an immune deficiency, or a neurodegenerative disease.

In some embodiments, the present application provides use of a combination of a RAD51 inhibitor, or a pharmaceutically acceptable salt thereof, and olaparib, or a pharmaceutically acceptable salt thereof in the manufacture of a medicament for the treatment of a cancer, an autoimmune disease, an immune deficiency, or a neurodegenerative disease.

In some embodiments, the present application provides use of a composition comprising a RAD51 inhibitor, or a pharmaceutically acceptable salt thereof, and olaparib, or a pharmaceutically acceptable salt thereof in the manufacture of a medicament for the treatment of a cancer, an autoimmune disease, an immune deficiency, or a neurodegenerative disease.

In some embodiments, the present application provides use of Compound 67A, or a pharmaceutically acceptable salt thereof, or a pharmaceutical composition disclosed herein in combination with olaparib, or a pharmaceutically acceptable salt thereof, or a pharmaceutical composition thereof in the manufacture of a medicament for the treatment of a cancer, an autoimmune disease, an immune deficiency, or a neurodegenerative disease.

In some embodiments, the present application provides use of a combination of Compound 67A, or a pharmaceutically acceptable salt thereof, and olaparib, or a pharmaceutically acceptable salt thereof in the manufacture of a medicament for the treatment of a cancer, an autoimmune disease, an immune deficiency, or a neurodegenerative disease.

In some embodiments, the present application provides use of a composition comprising Compound 67A, or a pharmaceutically acceptable salt thereof, and olaparib, or a pharmaceutically acceptable salt thereof in the manufacture of a medicament for the treatment of a cancer, an autoimmune disease, an immune deficiency, or a neurodegenerative disease.

In some embodiments, the present application provides the use of a compound disclosed herein, or a pharmaceutically acceptable salt thereof, or a pharmaceutical composition disclosed herein for the treatment of a disease or disorder.

In some embodiments, the present application provides the use of a composition disclosed herein for the treatment of a disease or disorder.

In some embodiments, the present application provides the use of a combination disclosed herein for the treatment of a disease or disorder.

In some embodiments, the present application provides the use of a compound disclosed herein, or a pharmaceutically acceptable salt thereof, or a pharmaceutical composition disclosed herein for the treatment of a cancer, an autoimmune disease, an immune deficiency, or a neurodegenerative disease.

In some embodiments, the present application provides use of a compound disclosed herein, or a pharmaceutically acceptable salt thereof, or a pharmaceutical composition disclosed herein in combination with a PARP inhibitor, or a pharmaceutically acceptable salt thereof, or a pharmaceutical composition thereof for the treatment of a cancer, an autoimmune disease, an immune deficiency, or a neurodegenerative disease.

In some embodiments, the present application provides use of a combination of a compound disclosed herein, or a pharmaceutically acceptable salt thereof, and a PARP inhibitor, or a pharmaceutically acceptable salt thereof for the treatment of a cancer, an autoimmune disease, an immune deficiency, or a neurodegenerative disease.

In some embodiments, the present application provides use of a composition comprising a compound disclosed herein, or a pharmaceutically acceptable salt thereof, and a PARP inhibitor, or a pharmaceutically acceptable salt thereof for the treatment of a cancer, an autoimmune disease, an immune deficiency, or a neurodegenerative disease.

In some embodiments, the present application provides use of a RAD51 inhibitor, or a pharmaceutically acceptable salt thereof, or a pharmaceutical composition disclosed herein in combination with a PARP inhibitor, or a pharmaceutically acceptable salt thereof, or a pharmaceutical composition thereof for the treatment of a cancer, an autoimmune disease, an immune deficiency, or a neurodegenerative disease.

In some embodiments, the present application provides use of a combination of a RAD51 inhibitor, or a pharmaceutically acceptable salt thereof, and a PARP inhibitor, or a pharmaceutically acceptable salt thereof for the treatment of a cancer, an autoimmune disease, an immune deficiency, or a neurodegenerative disease.

In some embodiments, the present application provides use of a composition comprising a RAD51 inhibitor, or a pharmaceutically acceptable salt thereof, and a PARP inhibitor, or a pharmaceutically acceptable salt thereof for the treatment of a cancer, an autoimmune disease, an immune deficiency, or a neurodegenerative disease.

In some embodiments, the present application provides use of Compound 67A, or a pharmaceutically acceptable salt thereof, or a pharmaceutical composition disclosed herein in combination with a PARP inhibitor, or a pharmaceutically acceptable salt thereof, or a pharmaceutical composition thereof for the treatment of a cancer, an autoimmune disease, an immune deficiency, or a neurodegenerative disease.

In some embodiments, the present application provides use of a combination of Compound 67A, or a pharmaceutically acceptable salt thereof, and a PARP inhibitor, or a pharmaceutically acceptable salt thereof for the treatment of a cancer, an autoimmune disease, an immune deficiency, or a neurodegenerative disease.

In some embodiments, the present application provides use of a composition comprising Compound 67A, or a pharmaceutically acceptable salt thereof, and a PARP inhibitor, or a pharmaceutically acceptable salt thereof for the treatment of a cancer, an autoimmune disease, an immune deficiency, or a neurodegenerative disease.

In some embodiments, the present application provides use of a compound disclosed herein, or a pharmaceutically acceptable salt thereof, or a pharmaceutical composition disclosed herein in combination with olaparib, or a pharmaceutically acceptable salt thereof, or a pharmaceutical composition thereof for the treatment of a cancer, an autoimmune disease, an immune deficiency, or a neurodegenerative disease.

In some embodiments, the present application provides use of a combination of a compound disclosed herein, or a pharmaceutically acceptable salt thereof, and olaparib, or a pharmaceutically acceptable salt thereof for the treatment of a cancer, an autoimmune disease, an immune deficiency, or a neurodegenerative disease.

In some embodiments, the present application provides use of a composition comprising a compound disclosed herein, or a pharmaceutically acceptable salt thereof, and olaparib, or a pharmaceutically acceptable salt thereof for the treatment of a cancer, an autoimmune disease, an immune deficiency, or a neurodegenerative disease.

In some embodiments, the present application provides use of a RAD51 inhibitor, or a pharmaceutically acceptable salt thereof, or a pharmaceutical composition disclosed herein in combination with olaparib, or a pharmaceutically acceptable salt thereof, or a pharmaceutical composition thereof for the treatment of a cancer, an autoimmune disease, an immune deficiency, or a neurodegenerative disease.

In some embodiments, the present application provides use of a combination of a RAD51 inhibitor, or a pharmaceutically acceptable salt thereof, and olaparib, or a pharmaceutically acceptable salt thereof for the treatment of a cancer, an autoimmune disease, an immune deficiency, or a neurodegenerative disease.

In some embodiments, the present application provides use of a composition comprising a RAD51 inhibitor, or a pharmaceutically acceptable salt thereof, and olaparib, or a pharmaceutically acceptable salt thereof for the treatment of a cancer, an autoimmune disease, an immune deficiency, or a neurodegenerative disease.

In some embodiments, the present application provides use of Compound 67A, or a pharmaceutically acceptable salt thereof, or a pharmaceutical composition disclosed herein in combination with olaparib, or a pharmaceutically acceptable salt thereof, or a pharmaceutical composition thereof for the treatment of a cancer, an autoimmune disease, an immune deficiency, or a neurodegenerative disease.

In some embodiments, the present application provides use of a combination of Compound 67A, or a pharmaceutically acceptable salt thereof, and olaparib, or a pharmaceutically acceptable salt thereof for the treatment of a cancer, an autoimmune disease, an immune deficiency, or a neurodegenerative disease.

In some embodiments, the present application provides use of a composition comprising Compound 67A, or a pharmaceutically acceptable salt thereof, and olaparib, or a pharmaceutically acceptable salt thereof for the treatment of a cancer, an autoimmune disease, an immune deficiency, or a neurodegenerative disease.

In some embodiments, the present application provides a compound disclosed herein, or a pharmaceutically acceptable salt thereof, or a pharmaceutical composition disclosed herein for use in treating a disease or disorder.

In some embodiments, the present application provides a composition disclosed herein for use in treating a disease or disorder.

In some embodiments, the present application provides a combination disclosed herein for use in treating a disease or disorder.

In some embodiments, the present application provides a compound disclosed herein, or a pharmaceutically acceptable salt thereof, or a pharmaceutical composition disclosed herein for use in treating a cancer, an autoimmune disease, an immune deficiency, or a neurodegenerative disease.

In some embodiments, the present application provides a compound disclosed herein, or a pharmaceutically acceptable salt thereof, or a pharmaceutical composition disclosed herein in combination with a PARP inhibitor, or a pharmaceutically acceptable salt thereof, or a pharmaceutical composition thereof for use in treating a cancer, an autoimmune disease, an immune deficiency, or a neurodegenerative disease.

In some embodiments, the present application provides a combination of a compound disclosed herein, or a pharmaceutically acceptable salt thereof and a PARP inhibitor, or a pharmaceutically acceptable salt thereof for use in treating a cancer, an autoimmune disease, an immune deficiency, or a neurodegenerative disease.

In some embodiments, the present application provides a composition comprising a compound disclosed herein, or a pharmaceutically acceptable salt thereof, and a PARP inhibitor, or a pharmaceutically acceptable salt thereof for use in treating a cancer, an autoimmune disease, an immune deficiency, or a neurodegenerative disease.

In some embodiments, the present application provides a RAD51 inhibitor, or a pharmaceutically acceptable salt thereof, or a pharmaceutical composition disclosed herein in combination with a PARP inhibitor, or a pharmaceutically acceptable salt thereof, or a pharmaceutical composition thereof for use in treating a cancer, an autoimmune disease, an immune deficiency, or a neurodegenerative disease.

In some embodiments, the present application provides a combination of a RAD51 inhibitor, or a pharmaceutically acceptable salt thereof and a PARP inhibitor, or a pharmaceutically acceptable salt thereof for use in treating a cancer, an autoimmune disease, an immune deficiency, or a neurodegenerative disease.

In some embodiments, the present application provides a composition comprising a RAD51 inhibitor, or a pharmaceutically acceptable salt thereof, and a PARP inhibitor, or a pharmaceutically acceptable salt thereof for use in treating a cancer, an autoimmune disease, an immune deficiency, or a neurodegenerative disease.

In some embodiments, the present application provides Compound 67A, or a pharmaceutically acceptable salt thereof, or a pharmaceutical composition disclosed herein in combination with a PARP inhibitor, or a pharmaceutically acceptable salt thereof, or a pharmaceutical composition thereof for use in treating a cancer, an autoimmune disease, an immune deficiency, or a neurodegenerative disease.

In some embodiments, the present application provides a combination of Compound 67A, or a pharmaceutically acceptable salt thereof and a PARP inhibitor, or a pharmaceutically acceptable salt thereof for use in treating a cancer, an autoimmune disease, an immune deficiency, or a neurodegenerative disease.

In some embodiments, the present application provides a composition comprising Compound 67A, or a pharmaceutically acceptable salt thereof, and a PARP inhibitor, or a pharmaceutically acceptable salt thereof for use in treating a cancer, an autoimmune disease, an immune deficiency, or a neurodegenerative disease.

In some embodiments, the present application provides a compound disclosed herein, or a pharmaceutically acceptable salt thereof, or a pharmaceutical composition disclosed herein in combination with olaparib, or a pharmaceutically acceptable salt thereof, or a pharmaceutical composition thereof for use in treating a cancer, an autoimmune disease, an immune deficiency, or a neurodegenerative disease.

In some embodiments, the present application provides a combination of a compound disclosed herein, or a pharmaceutically acceptable salt thereof and olaparib, or a pharmaceutically acceptable salt thereof for use in treating a cancer, an autoimmune disease, an immune deficiency, or a neurodegenerative disease.

In some embodiments, the present application provides a composition comprising a compound disclosed herein, or a pharmaceutically acceptable salt thereof, and olaparib, or a pharmaceutically acceptable salt thereof for use in treating a cancer, an autoimmune disease, an immune deficiency, or a neurodegenerative disease.

In some embodiments, the present application provides a RAD51 inhibitor, or a pharmaceutically acceptable salt thereof, or a pharmaceutical composition disclosed herein in combination with olaparib, or a pharmaceutically acceptable salt thereof, or a pharmaceutical composition thereof for use in treating a cancer, an autoimmune disease, an immune deficiency, or a neurodegenerative disease.

In some embodiments, the present application provides a combination of a RAD51 inhibitor, or a pharmaceutically acceptable salt thereof and olaparib, or a pharmaceutically acceptable salt thereof for use in treating a cancer, an autoimmune disease, an immune deficiency, or a neurodegenerative disease.

In some embodiments, the present application provides a composition comprising a RAD51 inhibitor, or a pharmaceutically acceptable salt thereof, and olaparib, or a pharmaceutically acceptable salt thereof for use in treating a cancer, an autoimmune disease, an immune deficiency, or a neurodegenerative disease.

In some embodiments, the present application provides Compound 67A, or a pharmaceutically acceptable salt thereof, or a pharmaceutical composition disclosed herein in combination with olaparib, or a pharmaceutically acceptable salt thereof, or a pharmaceutical composition thereof for use in treating a cancer, an autoimmune disease, an immune deficiency, or a neurodegenerative disease.

In some embodiments, the present application provides a combination of Compound 67A, or a pharmaceutically acceptable salt thereof and olaparib, or a pharmaceutically acceptable salt thereof for use in treating a cancer, an autoimmune disease, an immune deficiency, or a neurodegenerative disease.

In some embodiments, the present application provides a composition comprising Compound 67A, or a pharmaceutically acceptable salt thereof, and olaparib, or a pharmaceutically acceptable salt thereof for use in treating a cancer, an autoimmune disease, an immune deficiency, or a neurodegenerative disease.

In some embodiments, the disease or disorder is a cancer.

In some embodiments, the disease or disorder is an autoimmune disease.

In some embodiments, the disease or disorder is an immune deficiency.

In some embodiments, the disease or disorder is a neurodegenerative disease.

In some embodiments, a compound disclosed herein is a RAD51 inhibitor.

In some embodiments, the RAD51 inhibitor is compound 67A.

In some embodiments, the PARP inhibitor is olaparib.

In some embodiments, the disease or disorder is a disease or disorder in which RAD51 plays a role in the initiation or development of the disease or disorder. In some embodiments, the disease or disorder is a disease or disorder in which PARP plays a role in the initiation or development of the disease or disorder. In some embodiments, the disease or disorder is a disease or disorder in which RAD51 or PARP plays a role in the initiation or development of the disease or disorder. In some embodiments, the disease or disorder is a disease or disorder in which RAD51 and PARP play a role in the initiation or development of the disease or disorder.

In some embodiments, the disease or disorder is cancer in which RAD51 plays a role in the initiation or development of the cancer. In some embodiments, the disease or disorder is cancer in which PARP plays a role in the initiation or development of the cancer. In some embodiments, the disease or disorder is cancer in which RAD51 or PARP plays a role in the initiation or development of the cancer. In some embodiments, the disease or disorder is cancer in which RAD51 and PARP play a role in the initiation or development of the disease or disorder.

In some embodiments, the disease or disorder is associated with (e.g., possesses) one or more mutations in or dysregulation of, or is deficient in, one or more genes selected from BRCA1, BRCA2, ATR, ATM, CHK1, CHK2, RAD51, RPA, XRCC3, FANCA, FANCC, FANCD2, FANCF, FANCG, and FANCM. In some embodiments, the disease or disorder is cancer associated with (e.g., possesses) one or more mutations in or dysregulation of, or is deficient in, one or more genes selected from BRCA1, BRCA2, ATR, ATM, CHK1, CHK2, RAD51, RPA, XRCC3, FANCA, FANCC, FANCD2, FANCF, FANCG, and FANCM.

In some embodiments, the cancer described herein is selected from hematological cancer, breast cancer, ovarian cancer, pancreatic cancer, prostate cancer, fallopian tube cancer, peritoneal cancer, and lung cancer, each as described herein. In some embodiments, the cancer described herein is a recurrent cancer (e.g., recurrent breast cancer, or recurrent ovarian cancer). In some embodiments, the cancer described herein is a metastatic cancer. In some embodiments, the cancer described herein is associated with (e.g., possesses) one or more mutations in or dysregulation of, or is deficient in, one or more genes selected from BRCA1, BRCA2, ATR, ATM, CHK1, CHK2, RAD51, RPA, XRCC3, FANCA, FANCC, FANCD2, FANCF, FANCG, and FANCM. In some embodiments, the cancer described herein is associated with (e.g., possesses) one or more mutations in or dysregulation of, or is deficient in BRCA1 and/or BRCA2.

In some embodiments, the subject can be a subject determined to have an increased level of DNA damage occurring in one or more cell types relative to a reference level. As used herein, "DNA damage" refers to breaks, nicks, and mutations of the DNA present in a cell. In some embodiments, the DNA damage can comprise one or more of single-strand breaks (e.g., "nicks"), double strand breaks (DSBs), and mutations. In some embodiments, the DNA damage can be one or more DSBs. As used herein, "mutation" refers to a change or difference in the genetic material of a cell as compared to a reference wildtype cell, e.g. a deletion, an insertion, a SNP, a gene rearrangement, and/or the introduction of an exogenous gene or sequence.

In some embodiments, the subject can be determined to have an increased level of DNA damage if the subject is determined to have an increased level and/or activity of a DNA damage process or DNA editing enzyme. As used herein, "DNA damage process" refers to any activity or process in a cell which causes one or more types of DNA damage to occur.

In some embodiments, an increased level of DNA damage can be an increased level of mutations, e.g., by determining the overall mutation status in all or a portion of the genome of a cell. An overall mutation status at least 2% greater, e.g. 2% greater or more, 3% greater or more, 5% greater or more, 10% greater or more, or 20% greater or more than the overall mutation status in a reference cell can be indicative of an increased, elevated, and/or significant level of a DNA editing enzyme activity. In some embodiments, the level of hyper mutations can be determined. In some embodiments, the overall mutation status in the whole genome or a portion thereof can be determined using FISH, whole genome sequencing, high throughput sequencing, exome sequencing, hybridization, and/or PCR. In some embodiments the activity of a DNA editing enzyme can be measured by determining the level of hypermutations in the specific target genes including, but not limited to IGH, BCL6, MYC, BCL1 1A, CD93, PIM1 and/or PAX5. In some embodiments the DNA editing enzyme is AID. In some embodiments, a level of mutation in specific target genes including IGH, BCL6, MYC, BCL1 1A, CD93, PIM1 and/or PAX5 which is at least 2% greater, e.g. 2% greater or more, 3% greater or more, 5% greater or more, 10% greater or more, or 20% greater or more than the level of mutation in IGH, BCL6, MYC, BCL1 1A, CD93, PIM1 and/or PAX5 in a reference cell can be indicative of an increased, elevated, and/or significant level of AID activity.

In some embodiments, an increased level of DNA damage can be an increased level of double strand breaks (DSBs). The level of DSBs can be determined, by way of non-limiting example, by karyotyping, by γ-H2AX foci formation, and/or by using FISH analysis to detect DNA double strand breaks, e.g. DNA breakage detection fish (DBD-FISH) (Volpi and Bridger, BioTechniques, Vol. 45, No. 4, October 2008, pp. 385-409).

In some embodiments, an increased level of DNA damage can be an increased level of single strand breaks. The level of single-strand breaks in DNA can be determined, by way of non-limiting example, by COMET assays, FISH, or the use of single-strand break-specific probes. Detection of DNA breaks, both single and double-stranded is known in the art and described further, at, e.g., Kumari et al. EXCLI Journal 2009 7:44-62 and Motalleb et al. Research Journal of Applied Sciences, Engineering and Technology. 2012 4: 1888-1894; each of which is incorporated by reference herein in its entirety.

In some embodiments, an increased level of activity of a DNA damage process can comprise an increased level and/or activity of a DNA editing enzyme. In some embodiments, the technology described herein is directed to treating cells having an active DNA editing enzyme with a compound of the present application in combination with a PARP inhibitor. In some embodiments, the technology described herein is directed to treating cells having an increased level and/or activity of a DNA editing enzyme with a compound of the present application in combination with a PARP inhibitor. As used herein, "DNA editing enzyme" refers to an enzyme which normally catalyzes the mutation, exchange or excision of DNA segments, particularly enzymes which can generate or promote the generation of point mutations, DNA single strand breaks, DNA double-strand breaks or protein-DNA adducts. A DNA editing enzyme, as referred to herein, is not necessarily site-specific in its action. Similarly, it is not necessarily cell specific. In some embodiments, the cell is a B cell expressing a detectable amount of such an enzyme.

Non-limiting examples of DNA editing enzymes include, but are not limited to Recombination Activating Gene 1 (RAG1; NCBI Gene ID: 5896), Recombination Activating Gene 1 (RAG2; NCBI Gene ID: 5897), Sporulation-specific protein 11 (SPO11; NCBI Gene ID: 23626), APOBEC family members a Type 1 Topoisomerase; a Type 2 Topoisomerase; and/or AID. In some embodiments, the DNA editing enzyme can be AID.

In some embodiments, the DNA editing enzyme can be a member of the APOBEC (apolipoprotein B mRNA editing enzyme, catalytic polypeptide-like) family. As used herein "APOBEC family" refers to a family of cytidine deaminase enzymes having an N-terminal zinc-dependent cytidine deaminase catalytic domain comprising and a C-terminal pseudocatalytic domain. Non-limiting examples of APOBEC family members include AID, APOBEC 1 (e.g., NCBI Gene ID: 339), APOBEC2 (e.g., NCBI Gene ID: 10930), APOBEC3A (e.g., NCBI Gene ID: 200315), APOBEC3C (e.g., NCBI Gene ID: 27350), APOBEC3E (e.g., NCBI Gene ID: 140564), APOBEC3F (e.g., NCBI Gene ID: 200316), APOBEC3G (e.g., NCBI Gene ID: 60489), APOBEC3H (e.g., NCBI Gene ID: 164668), and APOBEC4 (e.g., NCBI Gene ID: 403314).

In some embodiments, the DNA editing enzyme can be a Type 1 topoisomerase. In some embodiments, the DNA editing enzyme can be a Type 2 topoisomerase. Topoisomerases generate breaks in DNA to help uncoil or relax the strand. Type II topoisomerases hydrolyze ATP to generate DSB cuts, while Type I topoisomerases generate single-stranded breaks. Non-limiting examples of Type II topoisomerases can include topoisomerase II (e.g., NCBI Gene ID: 7153 and 7155). Non-limiting examples of Type I topoisomerases can include topoisomerase I (e.g., NCBI Gene ID: 7150).

Embodiments of the technology described herein are based on the discovery that the compounds described herein can inhibit DNA repair mechanisms, e.g., homologous repair, and act synergistically with a PARP inhibitor. Activation-induced cytidine deaminase (AID, or AICDA, also known as ARP2, CDA2 or HIGM2), a DNA-editing enzyme that is a member of the apolipoprotein B mRNA editing enzymes, catalytic polypeptide-like (APOBEC), will cause widespread genomic breaks and cell death in cells with diminished homologous recombination ability (e.g. cells with diminished DNA double strand break repair abilities). Accordingly, provided herein is a method of causing cell death comprising detecting increased expression of a DNA-editing enzyme (e.g. AID) in a cell and thereafter contacting the cell with a compound of the present application in combination with a PARP inhibitor; thereby resulting in cell death. Accordingly, provided herein is a method of causing cell death comprising increasing expression of a DNA-editing enzyme (e.g. AID) in a cell and thereafter contacting the cell with a compound of the present application in combination with a PARP inhibitor; thereby resulting in cell death. Accordingly, provided herein is a method of causing cell death comprising administering to a cell a therapeutically effective amount of a DNA editing enzyme (e.g. AID) and thereafter contacting the cell with a compound of the present application in combination with a PARP inhibitor; thereby resulting in cell death.

AID, encoded by the AICDA gene (NCBI Gene ID: 57379), is required for proper B-cell function and is most prominently expressed in centroblast B-cells. The protein is involved in somatic hypermutation, gene conversion, and class-switch recombination of immunoglobulin genes. AID is normally expressed almost exclusively in antigen-activated germinal center B-cells, where it initiates immunoglobulin isotype class switching (Manis et al. 2002, Trends Immunol, 23, 31-39; Chaudhuri and Alt, Nat Rev Immunol, 2004, 4, 541-552; Longerich et al., Curr Opin Immunol, 2006, 18, 164-174; Chaudhuri et al., Adv Immunol 2007, 94, 157-214). AID is required for somatic hypermutation and immunoglobulin class switching in activated B cells. AID expression is regulated by CD40 ligand, B-cell receptor, IL4R, or Toll-like receptor stimulation (Crouch et al., J Exp Med 2007 204: 1145-1156; Muramatsu et al., J Biol Chem 1999 274: 18470-6). After activation, AID is transiently upregulated, induces point mutations or DNA double strand breaks in a sequence nonspecific manner within immunoglobulin genes, and is then downregulated (Longerich et al., Curr Opin Immunol, 2006, 18, 164-176; Chaudhuri et al., Adv Immunol 2007, 94, 157-214). Overall, AID is active in only a tiny population of normal cells (antigen-activated B-cells) at any given time. The genomic rearrangements and mutations controlled by AID lead to the development of antigen-recognition diversity, receptor editing and lymphoid effector function required for functional adaptive immunity (Mills, et al. Immunol Rev 2003 194:77-95). Recently it has been reported that AID has off-target point mutation activities (Liu, M. et al., Nature 2008, 451, 841-845; Liu and Schatz, Trends Immunol. 2009, 30, 173-181; Perez-Duran et al., Carcinogenesis. 2007, 28(12):2427-33). Robbiani et al. has reported off-target activities of AID in B-cells, especially c-myc/IgH translocations (Robbiani et al., Mol Cell 2009, 36(4):631-41). AID expression accelerates the rate of tumor development in Bcl6 transgenic mice (Pasqualucci et al., 2008, Nat. Genet. 40, 108-112). However, deregulated AID does not necessarily cause malignancy or translocation-associated cancer on its own in B cells (Muto et al., 2006, Proc. Natl. Acad. Sci. USA 103, 2752-2757; Okazaki et al., 2003, J. Exp. Med. 197, 1173-1181; Shen et al., 2008, Mol. Immunol. 45, 1883-1892). In addition, despite its obligate role in c-myc/IgH translocation, AID is not required for the development of plasmacytosis or plasmacytoma in IL-6 transgenic or pristane-treated mice, respectively (Kovalchuk et al., 2007, J. Exp. Med. 204, 2989-3001; Ramiro et al., 2004, J. Exp. Med. 200, 1103-1110). However, most human B cell lymphoma-associated translocations do not involve c-myc, and many do not involve Ig genes (Kuppers, 2005, Oncogene 20, 5580-5594).

Overexpression of AID has been reported in chronic lymphocytic leukemia (CLL) (Hancer et al. Leuk Lymphoma. 2011 January; 52(1):79-84; Heintel et al., Leukemia. 2004 April; 18(4):756-62). Further, AID expression has been shown to be correlated with blast crisis B lineage leukemia and therapy resistance in myeloid leukemia and to be associated with generally poor prognosis in chronic B lymphocytic leukemia (Mao et al., Br J Dermatol 2001, 145: 117-122; Chaudhuri et al., Nature 2004, 430:992-8). Further expression of AID in tumor cells from a variety of cancers has been reported including but not limited to lung, breast, gastric, colon, intestinal, liver cancer and choriangiocarcinoma (Greeve et al., Blood 2003, 1010, 3574-3580; Feldhahn et al., J Exp Med 2007, 204, 1157-1166; Kotani et al., PNAS USA 2007, 104, 1616-1620; Engels et al., 2008, Appl Immunohistochem Mol Morphol 16, 521-529; Klemm et al., 2009, Cancer Cell 6, 232-245; Palacios et al., 2010, Blood 115(22), 4488-4496; Leuenberger et al., 2009, Mod Pathol 32, 177-186; Gruber et al., 2010, Cancer Res 70, 7411-7420; inflammatory cancer (Marusawa 2008, Int J Biochem Cell Biol. 40, 399-402); follicular lymphoma (Hardianti et al., 2004, Leukemia 18, 826-831; Shikata et al., 2012, Cancer Sci. 103(3):415-21); thyroid cancer (Qiu et al. 2012, Mod Pathol 25(1), 36-45); breast cancer (Borchert et al. 2011, BMC Cancer 11:347); Marusawa, et al., 2011, Adv Immunol 111: 109-41; Zhang et al. 2012, Hum Pathol 43(3):423-34; Komori et al., 2008, Hepatology 47(3):888-896; Hockley 2010, Leukemia 24(5): 1084-6; adult T-cell leukemia (Nakamura et al., 2011, Br J Dermatol. 165(2):437-9). All of the references in the foregoing paragraph are incorporated by reference herein in their entireties.

Elevated levels of AID have been reported in arthritis (Xu et al. Scand. J. Immunol. 2009, 296, 2033-6) and in the MRL/Fas(lpr/lpr) mouse lupus model (White et al. 2011, Autoimmunity 44(8), 585-98). All of the references in the foregoing paragraph are incorporated by reference herein in their entireties.

When DSB repair is inhibited, the extent of the DSBs generated by AID is much higher than previously suspected and the extent of genomic damage is so severe as to result in cell death. Accordingly, in one embodiment of the technology described herein, there is provided a method of treatment comprising; (a) selecting a subject having cells that express elevated levels of activation-induced cytidine deaminase (AID); and (b) administering a therapeutically effective amount of an inhibitor of double strand break repair (e.g. a compound of the present application) to the subject; wherein an elevated level of AID is a level of AID that is higher than the level of AID in cells of the same type from a healthy individual. In some embodiments, the cells expressing elevated levels of AID are B cells. In some embodiments, the B cell expressing elevated levels of AID is a cancerous B cells or a B cell associated with autoimmune disease. In some embodiments, the subject can be a human subject.

Methods provided herein treat cancers and/or autoimmune disorders by inhibiting DNA double strand break repair. This inhibition proves lethal to cells expressing AID, as AID generates widespread genomic breaks, and the treatment with a double strand break repair inhibitor prevents the repair of these lesions which are being generated by the cell itself. This results in cell death in the subject which is specific to the cells expressing AID, e.g. cancerous B cells and/or autoimmune cells. Accordingly, as described herein, in one embodiment there is a provided a treatment paradigm that selectively induces self-destruction of certain diseased cells, while reducing the unintended side effects in healthy tissues.

In some embodiments, an increased level and/or activity of a DNA editing enzyme can be an increased level of DNA editing enzyme mRNA. mRNA levels can be assessed using, e.g., biochemical and molecular biology techniques such as Northern blotting or other hybridization assays, nuclease protection assay, reverse transcription (quantitative RT-PCR) techniques, RNA-Seq, high throughput sequencing and the like. Such assays are well known to those in the art. In one embodiment, nuclear "run-on" (or "run-off) transcription assays are used (see e.g. Methods in Molecular Biology, Volume: 49, Sep. 27, 1995, Page Range: 229-238). Arrays can also be used; arrays, and methods of analyzing mRNA using such arrays have been described previously, e.g. in EP0834575, EP0834576, WO96/31622, U.S. Pat. No. 5,837,832 or WO98/30883. WO97/10365 provides methods for monitoring of expression levels of a multiplicity of genes using high density oligonucleotide arrays.

In some embodiments, a subject can be determined to have an increased level of DNA damage occurring in one or more cell types relative to a reference level if the subject has been exposed to an agent that is known to cause such DNA damage. Non-limiting examples of such agents can include a viral infection with a DNA integrating virus (e.g. adeno-associated virus, retrovirus, human T-lymphotropic virus, HIV-1, oncovirus, hepatitis virus, hepatitis B virus); DNA damaging chemicals (e.g. acetaldehyde, polycyclic aromatic hydrocarbons, benzenes, nitrosamines, tobacco smoke, aflatoxin, and the like); DNA damaging chemotherapeutic agents (e.g. bleomycin, mitomycin, nitrogen mustards (e.g. mechlorethamine, cyclophosphamide, melphalan, chlorambucil, ifosfamide and busulfan), nitrosoureas (e.g., N-Nitroso-N-methylurea (MNU), carmustine (BCNU), lomustine (CCNU) and semustine (MeCCNU), fotemustine and streptozotocin), tetrazines (e.g., dacarbazine, mitozolomide and temozolomide),aziridines (e.g., thiotepa, mytomycin and diaziquone (AZQ)), cisplatins (e.g., cisplatin, carboplatin and oxaliplatin) procarbazine and hexamethylmelamine); and ionizing or ultraviolet radiation. Exposure to such agents can be the result of an accident, infection and/or environmental exposure or the result of a therapeutic administration of such agents.

In some embodiments, the increased level of DNA damage can be occurring in a cell type affected by the cancer, autoimmune disease, and/or neurodegenerative disease. In some embodiments, the subject is determined to have an increased level of DNA damage occurring in a cell selected from the group consisting of: a cancer cell; an immune system cell; or a nervous system cell.

In some embodiments, the DNA editing enzyme can be AID. In some embodiments, the level of AID can be the level of AID in a blood cell. In some embodiments, the level of AID can be the level of AID in a B cell.

In some embodiments, an increased level of AID can be a detectable level of AID, e.g., as described below herein.

In some embodiments, the subject can be a human subject.

Methods provided herein treat cancers and/or autoimmune disorders by inhibiting DNA double strand break repair. This inhibition proves lethal to cells expressing AID, as AID generates widespread genomic breaks, and the treatment with a double strand break repair inhibitor prevents the repair of these lesions which are being generated by the cell itself. This results in cell death in the subject which is specific to the cells expressing AID, e.g. cancerous B cells and/or autoimmune cells. Accordingly, as described herein, in one embodiment there is a provided a treatment paradigm that selectively induces self-destruction of certain diseased cells, while reducing the unintended side effects in healthy tissues.

Methods of defecting cancers in patients with increased levels of DNA damage or increased levels of DNA editing enzymes are disclosed in WO2016/094897, incorporated herein by reference.

In some embodiments, the cancer to be treated is a type with high expression of a DNA editing enzyme. In some embodiments, the cancer to be treated is a B-cell neoplasm.

Another embodiment is a method of treating a cancer by administering to the subject a therapeutically effective amount of one or more disclosed compounds, or a pharmaceutically acceptable salt thereof, or the corresponding pharmaceutical composition in combination with a PARP inhibitor or a pharmaceutically acceptable salt thereof or a pharmaceutical composition comprising a PARP inhibitor. In one aspect, the cancer is selected from the group consisting of lymphoma, leukemia, and a plasma cell neoplasm. In another aspect, the cancer selected from the group consisting of carcinoma and sarcoma.

In some embodiments, the cancer to be treated is a lymphoma. Lymphomas which can be treated by the disclosed methods include Non-Hodgkin's lymphoma; Burkitt's lymphoma; small lymphocytic lymphoma; lymphoplasmacytic lymphoma; MALT lymphoma; follicular lymphoma; diffuse large B-cell lymphoma; mantle cell lymphoma; and T-cell lymphoma.

Lymphoma is a malignancy in the lymphatic cells of the immune system (e.g. B cells, T cells, or natural killer (NK) cells). Lymphomas often originate in the lymph nodes and present as solid tumors. They can metastasize to other organs such as the brain, bone, or skin. Extranodal sites are often located in the abdomen. Lymphomas are closely related to the lymphoid leukemia and in some cases a particular form of cancer is categorized as both a lymphoma and a leukemia.

Leukemias which can be treated by the disclosed methods include acute lymphoblastic leukemia (ALL); Burkitt's leukemia; B-cell leukemia; B-cell acute lymphoblastic leukemia; chronic lymphocytic leukemia (CLL); acute myelogenous leukemia (AML); chronic myelogenous leukemia (CML); and T-cell acute lymphoblastic leukemia (T-ALL).

In some embodiments the cancer to be treated is B-cell neoplasms, B-cell leukemia, B-cell acute lymphoblastic leukemia, chronic lymphocytic leukemia, chronic myelogenous leukemia, Burkitt's leukemia, acute myelogenous leukemia and/or T-ALL. The maturation of B cells most typically ceases or substantially decreases when the foreign antigen has been neutralized. Occasionally, however, proliferation of a particular B cell will continue unabated; such proliferation can result in a cancer referred to as "B-cell lymphoma" or a "B-cell leukemia." In some embodiments the cancer to be treated is chronic lymphocytic leukemia (CLL) or chronic myelogenous leukemia (CML).

In some embodiments the cancer to be treated is a plasma cell neoplasm. Examples for plasma cell neoplasms include multiple myeloma; plasma cell myeloma; plasma cell leukemia and plasmacytoma.

Carcinomas which can be treated by the disclosed methods include colon cancer; liver cancer; gastric cancer; intestinal cancer; esophageal cancer; breast cancer; ovarian cancer; head and neck cancer; lung cancer; and thyroid cancer.

Sarcomas which can be treated by the disclosed methods include soft tissue sarcoma and bone sarcoma.

Any cancer characterized by high levels of DNA damage and/or DNA editing enzyme expression can be treated with a combination as described herein. For example, sarcomas, epithelial cell cancer (carcinomas), colon cancer, gastric cancer, intestinal cancer, liver cancer, hepatocellular cancer, breast cancer, thyroid cancer, esophageal cancer, lung cancer, brain cancer, head and neck cancer, melanoma, renal cancer, prostate cancer, hemangioma, rhabdomyosarcoma, chondrosarcoma, osteosarcoma, fibrosarcoma and cholangiocarcinoma may be characterized by high levels of a DNA editing enzyme expression, e.g. AID. In some embodiments the cancer to be treated is colon cancer, liver cancer, gastric cancer, intestinal cancer, breast cancer, lung cancer, thyroid cancer and/or cholangiocarcinoma.

Specific cancers that can be treated by the disclosed methods include cancer of the bladder, blood, bone, bone marrow, brain, breast, colon, esophagus, gastrointestine, gum, head, kidney, liver, lung, nasopharynx, neck, ovary, prostate, skin, stomach, testis, tongue, or uterus. In addition, the cancer may specifically be of the following histological type, though it is not limited to these: neoplasm, malignant; carcinoma; carcinoma, undifferentiated; giant and spindle cell carcinoma; sarcomas; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malig melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; Kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; Ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; hodgkin's; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

In another embodiment for the disclosed method, the cancer is characterized by mutations in the mutS homologues (e.g., MSH2, MSH3, and MSH6), mutL homologues (e.g. MLH1), or mismatch repair endonuclease PMS2. Mutations are changes in the genetic code. They include point mutations and frameshift mutations. In a point mutation, one nucleotide is swapped out for another. Therefore, the mutation occurs at a single point or location within the DNA strand. Frameshift mutations are due to either insertions or deletions of nucleotides. This causes the entire DNA strand to elongate or to shrink in size. Thus, frameshift mutations may alter all of the codons that occur after the deletion or insertion. The mutations referred to herein include, but are not limited to, insertions, deletions, duplications, inversions, or other recognized point mutations. It has now been found that RAD51 inhibitors are particularly effective in treating cancers with mutations in MSH (e.g. MSH6), MLH, or PMS2.

MutS Homolog 2 (MSH2) is a protein that in humans is encoded by the MSH2 gene, which is located on chromosome 2. MSH2 is a tumor suppressor gene and more specifically a caretaker gene that codes for a DNA mismatch repair (MMR) protein, MSH2, which forms a heterodimer with MSH6 to make the human MutSα mismatch repair complex. It also dimerizes with MSH3 to form the MutSβ DNA repair complex. MSH2 is involved in many different forms of DNA repair, including transcription-coupled repair, homologous recombination, and base excision repair. Examples of the mutations in MSH2 include, but are not limited to, g.47630253_47630254del, g.47702411_47702421del, g.47709913_47709915inv, g.47635629_47635634del, g.47637227_47637236dup, g.47639550_47639561del, g.(?_47630206)_(47710367?)del, g.(?_47630206)_(47643569_47656880)del, g.47630263_47643568del, g.(?_47630206)_(47657081_47672686)del, g.47630263_47657080del, g.(?_47630206)_(47672797_47690169)del, g.47630263_47672796del, g.(?_47630206)_(47672797_47690169)del, g.(?_47630206)_(47693948_47698103)del, g.47630263_47693947del, g.(?_47630206)_(47698202_47702163)del, g.(?_47630206)_(47630542_47635539)del, g.(?_47630206)_(47708011_47709917)del, g.(?_47630206)_(47635695_47637232)del, g.(?_47630206)_(47635695_47637232)del, g.(?_47630206)_(47637512_47639552)del, g.(?_47630206)_(47639700_47641407)del, g.(?_47630206)_(47641558_47643434)del, g.47618487_47650860delins(155), g.47628578_47638433del, g.47595033_47662777del, g.47583175_47667707del, g.47625602_47636880del, g.47554933_47699909del, g.47629508_47649552del, g.47629375_47651274del, g.(?_47630206)_(47630542_47635539)del, g.(?_47630206)_(47635695_47637232)del, g.47643509_47643510del, g.47643529_47643530dup, g.47656746_47657199dup, g.47656661_47663325del, g.(47643569_47656880)_(47710367_?)del, g.(47643569_47656880)_(47710367_?)del, g.47656881_47657080del, g.(47643569_47656880)_(47657081_47672686)del, g.(47643569_47656880)_(47657081_47672686)del, g.(47643569_47656880)_(47657081_47672686)del, g.(47643569_47656880)_(47657081_47672686)dup, g.(47643569_47656880)_(47657081_47672686)dup, g.(47643569_47656880)_(47672797_47690169)del, g.(47643569_47656880)_(47693948_47698103)del, g.47656881_47693947del, g.(47643569_47656880)_(47702410_47703505)del, g.47656881_47656882ins(173), g.47656901_47656902insA, g.47656903del, g.47656912del, g.47630440del, g.47656923del, g.47656931_47656932dup, g.47656943del, g.47656943_47656949delinsCCCAGA, g.47656948dup, g.47656996dup, g.47657000_47657001dup, g.47630449del, g.47657007dup, g.47657008del, g.47657020_47657023dup, g.47657025_47657026del, g.47657026dup, g.47657030_47657031 del, g.47657047_47657050del, g.47657053del, g.47657053_47657057057del, g.47657064del, g.47657073dup, g.47657312_47676594del, g.47668611_47674615del, g.47672116_47675123del, g.47666463_47677632del, g.47666403_47677572del, g.(47657081_47672686)_(47710367_?)del, g.(47657081_47672686)_(47710367_?)inv, g.47671507_47675022delinsCATTCTCTTTGAAAA, g.47657278_47676557del, g.47672687_47672796del, g.(47657081_47672686)_(47672797_47690169)del, g.(47657081_47672686)_(47672797_47690169)del, g.(47657081_47672686)_(47693948_47698103)del, g.(47657081_47672686)_(47698202_47702163)del, g.(47657081_47672686)_(47708011_47709917)del, g.47672691dup, g.47672697dup, g.47672721_47672744delins47672748_47672771inv, g.47672728_47672729del, g.47672731dup, g.47672750_47672751 insGG, g.47672755_47672758del, g.47672762_47672763del, g.47630466_47630494del, g.47686194_47697740del, g.(47672797_47690169)_(47710367_?)del, g.(476-72797_47690169)_(47690294_47693796)del, g.(47672797_47690169)_(47693948_47698103)del, g.47690170_47693947del, g.(47672797_47690169)_(47693948_47698103)del, g.(47672797_47690169)_(47693948_47698103)dup, g.(47672797_47690169)_(47705659_47707834)del, g.47690173del, g.47690191del, g.47690216_47690217dup, g.47690227del, g.47690227dup, g.47690228_47690232del, g.47690230_47690231 del, g.47690240del, g.47690240_47690243del, g.47630475del, g.47630475_47630476del, g.47690259_47690260delinsCT, g.47690277dup, g.47690280del, g.47690283dup, g.(47690294_47693796)_(47702410_47703505)del, g.47630484_47630485insG, g.47693838_47693839del, g.47693862del, g.47693864del, g.47693873del, g.47693880dup, g.47693913del, g.47693924_47693925dup, g.47630493del, g.47697730_47706125del, g.(47693948_47698103)_(47710367_?)del, g.(47693948_47698103)_(47698202_47702163)del, g.(47693948_47698103)_(47705659_47707834)del, g.47698107del, g.47698109del, g.47698109_47698110insA, g.47630496del, g.47698118del, g.47698125del, g.47698129dup, g.47698138_47698139del, g.47698142_47698146del, g.47698144dup, g.47698147_47698148del, g.47698147_47698148dup, g.47698147_47698148insT, g.47698159del, g.47698162del, g.47698506_47703472del, g.47701803_47708848del, g.(47698202_47702163)_(47710367_?)del, g.(47698202_47702163)_(47702410_47703505)del, g.(47698202_47702163)_(47703711_47705410)del, g.(47698202_47702163)_(47705659_47707834)del, g.47702164del, g.47702175_47702176insA, g.47702183_47702186del, g.47702185_47702186insCT, g.47702190_47702192del, g.47702191dup, g.47702192_47702193del, g.47702213del, g.47702231del, g.47702242dup, g.47702257del, g.47702262_47702263dup, g.47630516_47630517dup, g.47630517del, g.47630517dup, g.47702289_47702290inv, g.47702293_47702296del, g.47702301dup, g.47702315del, g.47702315del, g.47702328_47702329del, g.47630522dup, g.47702339del, g.47702371_47702374dup, g.47702384_47702385del, g.47702386_47702389del, g.47702388del, g.47702388_47702389del, g.47702390del, g.47702390_47702391del, g.47702400_47702401 del, g.47703506_47703710 del, g.47703506_47708010del, g.47703510del, g.47703515del, g.47703521_47703522del, g.47703535_47703536del, g.47703546_47703547del, g.47703548_47703611dup, g.47630534del, g.47703571-dup, g.47703574_47703581del, g.47703585dup, g.47630350del, g.47632107_47668733del, g.47703613del, g.(47630542_47635539)_(47643569_47656880)del, g.(47630542_47635539)_(47643569_47656880)inv, g.(47630542_47635539)_(47657081_47672686)del, g.47635540_47657080del, g.(47630542_47635539)_(47672797_47690169)del, g.(47630542_47635539)_(47690294_47693796)del, g.(47630542_47635539)_(47705659_47707834)del, g.47635540_47635694del, g.(47630542_47635539)_(47635695_47637232)del, g.(47630542_47635539)_(47635695_47637232)del, g.(47630542_47635539)_(47637512_47639552)del, g.47703635dup, g.47703641dup, g.47635542_47635549del, g.47703660_47703663del, g.47703667dup, g.47630351dup, g.47703704del, g.47703826_47707938del, g.(47703711_47705410)_(47705659_47707834)del, g.47705428_47705431 del, g.47705437_47705438insA, g.47635551_47635552del, g.47705440_47705441 del, g.47705461del, g.47705490del, g.47705494del, g.47705495del, g.47635557_47635558del, g.47705505del, g.47705535dup, g.47705547del, g.47705560_47705561dup, g.47705561dup, g.47705562dup, g.47705588del, g.47705608_47705609del, g.47705618dup, g.47705627dup, g.47635571_47635601delins(217), g.(47705659_47707834)_(47710367?)del, g.(47705659_47707834)_(47708011_47709917)del, g.47707842_47707843del, g.47707861del, g.47707861_47707874dup, g.47707878_47707884del, g.47707878_47707884del, g.47707883del, g.47707895_47707905del, g.47707897del, g.47707901_47707902del, g.47707905_47707906del, g.47707921del, g.47635583dup, g.47635583_47635584del, g.47707969_47707973del, g.47707996_47707997ins(115), g.47708009_47708010del, g.(47708011_47709917)_(47710367 ?)del, g.47635591_47635592del, g.47635597_47635618dup, g.47635606_47635607del, g.47630359dup, g.47635672del, g.47635675_47635678del, g.47630364dup, g.47635680dup, g.47636862_47639040del, g.47636781_47638831del, g.47636753_47638155del, g.47636552_47638597del, g.(47635695_47637232)_(47643569_47656880)del, g.(47635695_47637232)_(47643569_47656880)del, g.(47635695_47637232)_(47657081_47672686)del, g.(47635695_47637232)_(47672797_47690169)del, g.(47635695_47637232)_(47698202_47702163)del, g.(47635695_47637232)_(47637512_47639552)del, g.(47635695_47637232)_(4764155847643434)del, g.47637234del, g.47637246_47637247del, g.47637253_47637254del, g.47637254_47637255del, g.47637254_47637255del, g.47637265del, g.47637274del, g.47637282del, g.47637320del, g.47637372_47637375del, g.47637377_47637449dup, g.47637379del, g.47637384del, g.47637394_47637395del, g.47637396_47637397del, g.47637417del, g.47637427_47637435del, g.47637437_47637439del, g.47637453del, g.47637458dup, g.47637479_47637482dup, g.47637482dup, g.47637504_47637505del, g.47637508_47637511 del, g.47638050_47653430del, g.47638302_47648462del, g.47638478_47648643del, g.(47637512_47639552)_(47710367_?)del, g.(47637512_47639552)_(47643569_47656880)del, g.47639553_47643568del, g.(47637512_47639552)_(47657081_47672686)del, g.(47637512_47639552)_(47657081_47672686)del, g.(47637512_47639552)_(47672797_47690169)del, g.(47637512_47639552)_(47639700_47641407)del, g.(47637512_47639552)_(47641558_47643434)del, g.47639557_47639561 del, g.47639582_47639586delinsTAAT, g.47639583_47639584del, g.47639594del, g.47639594dup, g.47639598del, g.47639603_47639604del, g.47639611_47639612del, g.47639612del, g.47639618_47639621del, g.47639624_47639628delinsTTA, g.47630401dup, g.47639632dup, g.47639638_47639641dup, g.47639638_47639641dup, g.47639639del, g.47639639del, g.47639642dup, g.47630403_47630404insC, g.47639653-del, g.47639666del, g.47639666_47639669del, g.47639-668del, g.47639670_47639673delinsTT, g.47639674_47639675dup, g.47639695_47639696del, g.47639707_47642985del, g.47641402_47642007del, g.(47639700_47641407)(4764356947656647656880)del, g.47641408_47643658del, g.(47639700_47641407)_(47657081_47672686)del, g.(47639700_47641407)_(47672797_47690169)del, g.(47639700_47641407)_(47641558_47643434)del, g.(47639700_47641407)_(47641558_47643434)del, g.47641410del, g.47641425_47641426del, g.47641426_47641429del, g.47630412del, g.47641451del, g.47641454dup, g.47641455dup, g.47641469del, g.47641478del, g.47641488_47641491del, g.47641496_47641497del, g.47641503del, g.47641513_47641514dup, g.47641530_47641537dup, g.47642509_47655432del, g.(47641558_4764343434)(4764356947656880)del, g.(47641558_47643434)_(47693948_47698103)del, g.47630424_47630433del, g.47643450dup, g.47643462_47643463del, g.47643462_47643463ins(4), g.47643464_47643465insNC_000022.10:35788169_35788352, g.47643465dup.

MutS Homolog 3 (MSH3) is a human homologue of the bacterial mismatch repair protein MutS that participates in the mismatch repair (MMR) system. MSH3 typically forms the heterodimer MutSβ with MSH2 in order to correct long insertion/deletion loops and base-base mispairs in microsatellites during DNA synthesis. Deficient capacity for MMR is found in approximately 15% of colorectal cancers, and somatic mutations in the MSH3 gene can be found in nearly 50% of MMR-deficient colorectal cancers. Examples of the mutations in MSH3 include, but are not limited to, g.79970809del.

MSH6 encodes MutS homologue 6 (MSH6), a member of the Mutator S (MutS) family of proteins that are involved in DNA mismatch repair (MMR). The MSH6 protein forms a heterodimer with MutS homologue 2 (MSH2) in both human and yeast. Human MSH2/6 recognizes single base-base mismatches and short insertion/deletion loops. Upon recognition of a mismatch, MSH2/6 complex binds and exchanges ADP for ATP, resulting in a conformational change to the complex that precedes base pair dissolution, base excision, and repair.

MSH6 mutations include frameshift and/or nonsense mutations and can result in non-functional MSH6 and loss of protein expression. Examples include a frameshift mutation at MSH6 amino acid residue 290 and a compounding missense T1189I.

Inactivating MSH6 mutations can be detected in cancers by routine diagnostics methods. These methods include, but are not limited to, obtaining cancer cells and other diagnostic indicators such as peripheral blood mononuclear cells (PBMCs), PBMC subpopulations, circulating blasts (CD34+ cells), circulating tumor cells and circulating exosomescancer cells by biopsy and blood tests and by obtaining lymphatic or other bodily fluids. It is then determined from the cancer cells or other diagnostic indicators whether the cancer exhibits an inactivating MSH6 mutation is by methodology known in the art, for example, direct DNA sequencing and multiplex ligation dependent probe amplification, RNA sequencing (RNA-Seq), microarray, quantitative PCR, or NanoString™ gene expression panels, or MSH6 protein by immunohistochemistry, flow cytometry, immunocytochemistry or Western blot. Methods for identifying inactivating MSH6 mutations are disclosed in Houlleberghs H, Goverde A, Lusseveld J, Dekker M, Bruno M J, et al. (2017) Suspected Lynch syndrome associated MSH6 variants: A functional assay to determine their pathogenicity. PLOS Genetics 13(5): e1006765. https://doi.org/10.1371/journal.pgen.1006765.

Examples of the mutations in MSH6 include, but are not limited to, g.48032846_48032849del, g.48032846_48032849del, g.48032846_48032849del, g.48033377_48033342del, g.48033420_48033422del, g.(?_48010221)_(48034092_?)del, g.(?_48010221)_(48018263_48023032)del, g.47998510_48020183del, g.48007276_48020272del, g.48026207del, g.48026223del, g.48026223del, g.48026257_48026261del, g.48026261_48026265del, g.48026312_48026313del, g.48026398del, g.48026543_48026544dup, g.48026693dup, g.48026702del, g.48026712del, g.48026718dup, g.48026736_48026737delinsAG, g.48026736_48026737delinsG, g.48026750_48026751 del, g.48026754_48026757del, g.48026756_48026759del, g.48026759_48026760del, g.48026906del, g.48026928_48026931del, g.48026941dup, g.48026991del, g.48027023_48027024del, g.48027079del, g.48027079_48027082dup, g.48027167_48027168del, g.48027172_48027173dup, g.48027178_48027185del, g.48027184_48027185del, g.48027272_48027275del, g.48027470_48027471del, g.48027501_48027502del, g.48027501_48027502del TG, g.48027657dup, g.48027691_48027694del, g.48027733_48027736dup, g.48027794_48027796delinsC, g.48027841_48027842del, g.48027887del, g.48027890dup, g.48027973_48027980del, g.48028067del, g.48028098del, g.48028106del, g.48028175_48028176del, g.48028241_48028242del, g.48028241_48028242delTT, g.48028272_48028284dup, g.48028277_48028278del, g.48030558_48030559del, g.48030126_48032394del, g.48030568del, g.48030581_48030584del, g.48030584_48030585dup, g.48030607del, g.48030645_48030646insT, g.48030647del, g.48030-647dup, g.48030649dup, g.48030654_48030660del, g.48030659dup, g.48030697_48030698del, g.48030698del, g.48030706del, g.48030710dup, g.48030727_48030728insC, g.48030765_48030829del, c.3438+797_3438+798insTATins1839_3439-428, c.3438+797_3438+798insTATins1839_3439-428, g.48032121_48032122del, g.48032123_48032124del, g.48032124dup, g.48032126_48032129del, g.48032129_48032130insA, g.48032129_48032132dup, g.(48032167_48032756)_(48034092_?)del, g.48032809_48032812del, g.480328-35dup, g.48032846_48032849del, g.48033374_48033402dup, g.48033395_48033398del, g.48033421_48033433del, g.48033425_48033428dup, g.48033453_48033454insA, g.48033494_48033523del, g.48033495_48033496del, g.48033593dup, g.48033610_48033613dup, g.48033629_48033635del, g.48033636_48033639dup, g.48033676_48033682del, g.48033707dup, g.48033709_48033716dup, g.48033721_48033724dup, g.48033727_48033730dup, g.48033728_48033746dup, g.(48033742_48033743)_(48033742_48033743)ins(32), g.48033746dup, g.48033748_48033751del, g.48033758_48033768del, g.48033773_48033774insATCA, g.48033773_48033776dup, g.48033785_48033789dup, g.48033887_48033910inv, g.(48018263_48023032)_(48032167_48032756)del, g.(48018263_48023032)_(48023203_48025749)del, g.48023097_48023098del, g.48025773dup, g.48025832del, g.48025860_48025861insT, g.48025884_48025885del, g.48025967dup.

MutL homolog 1, colon cancer, nonpolyposis type 2 (*E. coli*) is a protein that in humans is encoded by the MLH1 gene located on Chromosome 3. It is a gene commonly associated with hereditary nonpolyposis colorectal cancer.

Examples of the mutations in MSH6 include, but are not limited to, g.37089113_37089115del, g.37089175del, g.37090379_37090393del, g.37038201_37038202del, g.37042531_37042542del, g.37053339_37053355del, g.37053354del, g.37053590_37053591insT, g.37034841_37092337del, g.(?_37034841)_(37092337_?)del, g.(?_37034841)_(37061955_37067127)del, g.(?_37034841)_(37035155_37038109)del, g.(?_37034841)_(37035155_37038109)del, g.(?_37034841)_(37070424_37081676)del, g.(?_37034841)_(37083823_37089009)del, g.37034841_37083822del, g.(?_37034841)_(37038201_37042445)del, g.(?_37034841)_(37042545_37045891)del, g.37034841_37042544del, g.(?_37034841)_(37042545_37045891)del, g.(?_37034841)_(37042545_37045891)del, g.(?_3703-4841)_(37045966_37048481)del, g.(?_37034841)_(37050397_37053310)del, g.(?_37034841)_(37059091_37061800)del, g.37034658_37038806del, g.36961079_37138741del, g.37061923del, g.37061927del, g.37061933del, g.37061939del, g.37061942dup, g.37035140_37035141del, g.37070417del, g.37070417_37070418insT, g.37070419dup, g.37070422_37070423insT, g.37080355_37083368del, g.(37070424_37081676)_(37092337_?)del, g.(37070424_37081676)_(37081786_37083758)del, g.(37070424_37081676)_(37083823_37089009)del, g.37038148_37038151del, g.37038149del, g.37038149dup, g.37081690_37081691del, g.37081691_37081692del, g.37081706_37081708del, g.37081710_37081711del, g.37035053_37035066del, g.37038154_37038157del, g.37081738_37081739del, g.37081740del, g.37081753dup, g.37081757_37081761dup, g.37081782_37081783insAAGT, g.37081787_37081793delinsATTT, g.(37081786_37083758)_(37083823_37089009)del, g.(37081786_37083758)_(37089175_37090007)del, g.37083759del, g.37083780dup, g.37083781_37083784del, g.37083781_37083784delCTCA, g.37083808_37083809del, g.37083816del, g.37086069_37089606del, g.37084092_37089247del, g.37084590_37089786del, g.(37083823_37089009)_(37092337_?)del, g.(37083823_37089009)_(37089175_37090007)del, g.37089010_37089174del, g.(37083823_37089009)_(37090509_37091976)del, g.37089023del, g.37089026_37089027del, g.37089027del, g.37089036del, g.37089036dup, g.37038168dup, g.37089042del, g.37089047del, g.37089050_37089053del, g.37089056_37089057del, g.37089061_37089062del, g.37089078_37089096del, g.37089090dup, g.37089099dup, g.37089107_37089110dup, g.37089109_37089110del, g.37089130_37089132del, g.37089130_37089132delAAG, g.37089131delinsTTCTT, g.37089133del, g.37089133delG, g.37089144del, g.37089155del, g.37089155_37089161del, g.37089158_37089161del, g.37089162_37089166del, g.37089171del, g.(37089175_37090007)_(37090101_37090394)del, g.37035056_37035072del, g.37090013del, g.37090015dup, g.37038183_37038184del, g.37090024_37090037dup, g.37090025_37090053dup, g.37090027dup, g.37038184del, g.37090031_37090032insT, g.37090041del, g.37090057del, g.37090064_37090067del, g.37038188del, g.37090082del, g.37090086_37090087del, g.37090087_37090088del, g.37090097_37090101delinsC, g.37090099del, g.37038191dup, g.(37090101_37090394)_(37092337_?)del, g.37035057_37035073del, g.37090405dup, g.37090411_37090415del, g.37090414del, g.37038194del, g.37038198del, g.37090472_37090478del, g.37039445_37059613dup, g.37039760_37052440del, g.37090481_37090482del, g.37090483_37090484del, g.37090483_37092045del, g.37040732_37043185delinsACATAGTA, g.37042445_37042446del, g.(37038201_37042445)_(37042545_37045891)del, g.(37038201_37042445)_(37048555_37050304)del, g.(37038201_37042445)_(37050397_37053310)del, g.(37038201_37042445)_(37053591_37055922)del, g.37090497_37090498del, g.37090497_37090498delTC, g.37090504_37090507del, g.(37090509_37091976)_(37092337_?)del, g.(37090509_37091976)_(37092337_?)dup, g.37091977_37091978del, g.37091978_37091987del, g.37042448_37042451del, g.37091984_37091990del, g.37042451_37042453del, g.37092020_37092021del, g.37092022_37092068dup, g.37092027_37092028del, g.37092027_37092028dup, g.37092030dup, g.37092052_37092055del, g.37092054_37092055del, g.37092068_37092071dup, g.37092091dup, g.37092094_37092097delins(30), g.37092096_37092106del, g.37092097del, g.37092125_37092126delAA, g.37092125_37092126del, g.37092139_37092142dup, g.37092142dup, g.37035060dup, g.37042469_37042470del, g.37042470del, g.37042482dup, g.37042485del, g.37042499del, g.37042546dup, g.37044472_37046589del, g.37045648_37049941del, g.37045095_37054651del, g.37045072_37046861del, g.(37042545_37045891)_(37045966_37048481)del, g.(37042545_37045891)_(37092337_?)del, g.(37042545_37045891)_(37048555_37050304)del, g.(37042545_37045891)_(37050397_37053310)del, g.37045892_37050396del, g.37035069del, g.37045926del, g.37045931del, g.37035939_37045940dup, g.37045957_37045958del, g.37045963del, g.37035075del, g.37048067_37049287del, g.(37045966_37048481)_(37048555_37050304)del, g.(37045966_37048481)_(37050397_37053310)del, g.37048483del, g.37048483_37048503delinsT, g.37048486_37048487delinsGTT, g.37048489del, g.37048490del, g.37035076_37035077insCCCA, g.37035077_37035078dup, g.37048505_37048508del, g.37048521del, g.37048529dup, g.37035082dup, g.37049873_37052281del, g.37049839_37052249del, g.37049800_37052209del, g.37049640_37050445del, g.37050305_37050396del, g.(37048555_37050304)_(37050397_37053310)del, g.37050305_37050396del, g.37050319_37050320del, g.37050339del, g.37050348del, g.37050353_37050354del, g.37050354dup, g.37050364del, g.37050375_37050376insGA, g.37035090del, g.37050382_37050383delinsAT, g.37050382_37050383delinsCT, g.37050390_37050396del, g.37052950_37060990del, g.(37050397_37053310)_(37067499_37070274)dup, g.(37050397_37053310)_(37053591_37055922)del, g.(37050397_37053310)_(37056036_37058996)del, g.37053353del, g.37053510_37053511del, g.37035099del, g.37053545_37053546insT, g.37053562del, g.37053578del, g.37053578dup, g.37053585del, g.37053586_37053589del, g.37053591del, g.37053590_37053591delinsAT, g.37055920_37055921del, g.37055914_37055938del, g.(37053591_37055922)_(37070424_37081676)del, g.(37053591_37055922)_(37083823_37089009)del, g.(37053591_37055922)_(37059091_37061800)del, g.37035105del, g.37055928dup, g.37035106_37035116del, g.37055938del, g.37035108del, g.37055972_37055975del, g.37055976_37055979del, g.37035111del, g.37055990dup, g.37035114del, g.37035116del, g.37056036del, g.37056037dup, g.37058993_37059001del, g.(37056036_37058996)_(37070424_37081676)del, g.(37056036_37058996)_(37059091_37061800)del, g.37058997_37059000del, g.37059014_37059017del, g.37059017_37059021del, g.37059027_37059030dup, g.37035122del, g.37059062_37059063insT, g.37059065_37059066del, g.37059066del, g.37059066dup, g.37059072_37059073del, g.37059072_37059073dup, g.37059090_37059093del, g.37061595_37061913del, g.37061308_37066756del, g.37061207_37063077del, g.(37059091_37061800)_(37092337_?)del, g.(37059091_37061800)_(37061955_37067127)del, g.37061801_37061954del, g.(37059091_37061800)_(37083823_37089009)del, g.37061803dup, g.37061804del, g.37061817del, g.37061837_37061838dup, g.37061844del, g.37061851dup, g.37061855dup, g.37061870del, g.37061904_37061906del, g.37061910del, g.37035047del, g.[37049179_37051317delinsTG; 37051667_37054327delinsCA].

Human PMS2 related genes are located at bands 7p12, 7p13, 7q11, and 7q22. Exons 1 through 5 of these homologues share high degree of identity to human PMS2. The product of this gene is involved in DNA mismatch repair. The protein forms a heterodimer with MLH1 and this complex interacts with MSH2 bound to mismatched bases. Defects in this gene are associated with hereditary nonpolyposis colorectal cancer, with Turcot syndrome, and are a cause of supratentorial primitive neuroectodermal tumors.

Examples of the mutations in PMS2 include, but are not limited to, g.(?_6012870)_(6048737_?)del, g.6012870_6048737del, g.(6027252_6029430)_(6048737_?)del, g.(6045663_6048627)_(6048737_?)del, g.6029554del, g.6029499dup, g.6029495_6029496del, g.6029462_6029463delinsTAAA, g.5992485_6028601del, g.(6018328_6022454)_(6027252_6029430)del, g.(6013174_6017218)_(6027252_6029430)del, g.6027226_6027227ins(20), g.6027175del, g.6027090dup, g.6036705_6044207delinsCG, g.6026666dup, g.6026628del, g.6043671del, g.6026565dup, g.6026565dupT, g.6018315_6018316del, g.6018306_6018310del, g.6018306_6018310delAGTTA, g.6043633_6043634dup, g.6018256_6018259del, g.6015623_6017501del, g.6016429_6017479del, g.6017300_6017303del, g.6045579_6045674 delinsATTT, g.(6043690_6045522)_(6045663_6048627)del, g.(?_6012870)_(6042268_6043320)del, g.(6035265_6036956)_(6042268_6043320)del, g.6038283_6039384del, g.6038901del, g.6038851dup, g.(6035265_6036956)_(6037055_6038738)del, g.6037019_6037024delinsCTTCACACAC A, g.6036980del, g.6036958dup, g.6035323_6035324insJN866832.1, g.(6022623_6026389)_(6035265_6036956)del, g.(6031689_6035164)_(6035265_6036956)del, g.6035204_6035207del, g.6035205_6035206del, g.(?_6012870)_(6031689_6035164)del, g.(6027252_6029-430)_(6031689_6035164)del, g.(6029587_6031603)_(6031-689_6035164)del, g.6028725_6029882del, g.(?_6012870)_(6029587_6031603)del.

The present application provides a method of treating patients with Lynch syndrome to reduce the likelihood of from developing or treating cancers derived from Lynch syndrome, by administering to the subject a therapeutically effective amount of one or more disclosed compounds, or a pharmaceutically acceptable salt thereof, or the corresponding pharmaceutical composition in combination with a PARP inhibitor or a pharmaceutically acceptable salt thereof or a pharmaceutical composition comprising a PARP inhibitor.

Lynch syndrome is a hereditary disorder caused by a mutation in a mismatch repair gene in which affected individuals have a higher than normal chance of developing colorectal cancer, endometrial cancer, and various other types of aggressive cancers, often at a young age—also called hereditary nonpolyposis colon cancer (HNPCC).

The mutations of specific mismatch repair (MMR) genes including but not limited to MLH1, MSH2, MSH6, PMS2, and EPCAM-TACSTD1 deletions are responsible for Lynch syndrome. These genes work in repairing mistakes made when DNA is copied in preparation for cell division. The defects in the genes disallow repair of DNA mistakes and as cells divide, errors stack and uncontrollable cell growth may result in cancer.

Those with Lynch syndrome carry up to an 85% risk of contracting colon cancer as well as a higher than average risk for endometrial cancer, stomach cancer, pancreatic cancer, kidney/ureter tract cancer, hepatobiliary tract cancer, gastric tract cancer, prostate cancer, ovarian cancer, gallbladder duct cancer, brain cancer, small intestine cancer, breast cancer, and skin cancer.

Thus, in one embodiment for the disclosed method, the method is a method of treating cancer derived from Lynch syndrome, selected from the group consisting of colon cancer, endometrial cancer, stomach cancer, pancreatic cancer, kidney/ureter tract cancer, hepatobiliary tract cancer, gastric tract cancer, prostate cancer, ovarian cancer, gallbladder duct cancer, brain cancer, small intestine cancer, breast cancer, and skin cancer.

In yet another embodiment, the method is a method of treating autoimmune disease. Exemplary autoimmune diseases include lupus erythematosus; Wiskott-Aldrich syndrome; autoimmune lymphoproliferative syndrome; myasthenia gravis; rheumatoid arthritis (RA); lupus nephritis; multiple sclerosis; systemic lupus erythematosis; discoid lupus; subacute cutaneous lupus erythematosus; cutaneous lupus erythematosus including chilblain lupus erythematosus; chronic arthritis; Sjogren's syndrome; inflammatory chronic rhinosinusitis; colitis; celiac disease; inflammatory bowel disease; Barrett's esophagus; inflammatory gastritis; autoimmune nephritis; autoimmune vasculitis; autoimmune hepatitis; autoimmune carditis; autoimmune encephalitis; autoimmune diabetes; autoimmune diabetes nephritis; psoriasis; Graft-versus-host disease (GvHD); and autoimmune mediated hematological disease.

In one aspect of this embodiment, the method is a method of treating immune deficiency selected from the group consisting of Autoimmune Lymphoproliferative Syndrome (ALPS), Autoimmune polyglandular syndrome type 1 (APS-1), BENTA Disease, Caspase Eight Deficiency State (CEDS), Chronic Granulomatous Disease (CGD), Common Variable Immunodeficiency (CVID), Congenital Neutropenia Syndromes, CTLA4 Deficiency, DOCK8 Deficiency, GATA2 Deficiency, Glycosylation Disorders With Immunodeficiency, hyper-immunoglobulin E syndrome (HIES), Hyper-Immunoglobulin M (Hyper-IgM) Syndromes, Leukocyte adhesion deficiency (LAD), LRBA deficiency, PI3 Kinase disease, PLCG2-associated antibody deficiency and immune dysregulation (PLAID), severe combined immunodeficiency (SCID), STAT3 gain-of-function disease, Warts, Hypogammaglobulinemia, Infections, and Myelokathexis Syndrome (WHIMS), X-Linked Agammaglobulinemia (XLA), X-Linked Lymphoproliferative Disease (XLP), and XMEN Disease.

As used herein, the term "immune deficiency" refers to a condition in which a portion or some portions of cell components constituting an immune system are defective or dysfunction, so that a normal immune mechanism is damaged. In other words, "immune deficiency" means a condition under which: congenital immunity and/or acquired immunity are suppressed and/or decreased. In some embodiments, the immune-deficiency subject is an immunocompromised subject. Non-limiting examples of immune deficiencies can include AIDS, hypogammaglobulinemia, agammaglobulinemia, granulocyte deficiency, chronic granulomatous disease, asplenia, SCID, complement deficiency, and/or sickle cell anemia.

In another aspect of this embodiment, the method is a method of treating a neurodegenerative disorder selected from the group consisting of multiple sclerosis, Parkinson's disease (PD), Alzheimer's disease (AD), Dentatorubropallidoluysian atrophy (DRPLA), Huntington's Disease (HD), Spinocerebellar ataxia Type 1 (SCA1), Spinocerebellar ataxia Type 2 (SCA2), Spinocerebellar ataxia Type 3 (SCA3), Spinocerebellar ataxia 6 (SCA6), Spinocerebellar ataxia Type 7 (SCA7), Spinocerebellar ataxia Type 8 (SCA8), Spinocerebellar ataxia Type 12 (SCA12), Spinocerebellar ataxia Type 17 (SCA17), Spinobulbar Muscular Ataxia/Kennedy Disease (SBMA), Fargile X syndrome (FRAXA), Fragile XE mental retardation (FRAXE), and Myotonic dystrophy (DM).

A "subject" is a mammal, preferably a human, but can also be an animal in need of veterinary treatment, e.g., companion animals (e.g., dogs, cats, and the like), farm animals (e.g., cows, sheep, pigs, horses, and the like) and laboratory animals (e.g., rats, mice, guinea pigs, and the like).

In some embodiments, the methods disclosed herein further comprise co-administering a therapeutically effective amount of a DNA repair inhibitor, a DNA damage response (DDR) inhibitor, a DNA damaging agent or an immunomodulatory agent to the subject being treated for cancer, in addition to a therapeutically effective amount of a disclosed RAD51 inhibitor.

The term "DNA repair inhibitor" refers to any agent that targets components/processes which a cell uses to repair mutations or changes in DNA and restore the DNA to its original state and prevents the repair of DNA. Examples of DNA repair inhibitors include: RPA inhibitors, APE1 inhibitors, DNA ligase inhibitors, DNA polymerase inhibitors, Parp inhibitors etc.

The term "DNA damage response inhibitor" refers to any agent that targets components/processes involved in detecting DNA lesions, signaling the presence of DNA damage, and/or promote the repair of DNA damage. Examples of DNA damage response inhibitors include checkpoint inhibitors, ATM and ATR inhibitors, DNA-PK inhibitors, etc.

The term "DNA damaging agent" refers to any agent that directly or indirectly damages DNA for which homologous recombination could repair the damage. The DNA damaging agents is selected from the group consisting of: exposure to a DNA damaging chemical; exposure to a chemotherapeutic agent; exposure to a radiochemotherapy, and exposure to ionizing or ultraviolet radiation. Specific examples of DNA-damaging chemotherapeutic agents include alkylating agents, nitrosoureas, anti-metabolites, plant alkaloids, plant extracts and radioisotopes. Specific examples of the chemotherapeutic agents also include DNA-damaging drugs, for example, 5-fluorouracil (5-FU), capecitabine, S-1 (Tegafur, 5-chloro-2,4-dihydroxypyridine and oxonic acid), 5-ethynyluracil, arabinosyl cytosine (ara-C), 5-azacytidine (5-AC), 2',2'-difluoro-2'-deoxycytidine (dFdC), purine antimetabolites (mercaptopurine, azathiopurine, thioguanine), gemcitabine hydrochlorine (Gemzar), pentostatin, allopurinol, 2-fluoro-arabinosyl-adenine (2F-ara-A), hydroxyurea, sulfur mustard (bischloroetyhylsulfide), mechlorethamine, melphalan, chlorambucil, cyclophosphamide, ifosfamide, thiotepa, AZQ, mitomycin C, dianhydrogalactitol, dibromoducitol, alkyl sulfonate (busulfan), nitrosoureas (BCNU, CCNU, 4-methyl CCNU or ACNU), procarbazine, decarbazine, rebeccamycin, anthracyclins such as doxorubicin (adriamycin; ADR), daunorubicin (Cerubicine), idarubicin (Idamycin) and epirubicin (Ellence), anthracyclin analogs such as mitoxantrone, actinimycin D, non-intercalating topoisomerase inhibitors such as epipodophyllotoxins (etoposide or VP 16, teniposide or VM-26), podophylotoxin, bleomycin (Bleo), pepleomycin, compounds that form adducts with nucleic acid including platinum derivatives, e.g., cisplatin (CDDP), trans analog of cisplatin, carboplatin, iproplatin, tetraplatin and oxaliplatin, as well as camptothecin, topotecan, irinotecan (CPT-11), and SN-38. Specific examples of nucleic acid damaging treatments include radiation e.g., ultraviolet (UV), infrared (IR), or .alpha.-, .beta.-, or .gamma.-radiation, as well as environmental shock, e.g., hyperthermia.

"Immunomodulatory agent" means an agent that modulates an immune response to an antigen but is not the antigen or derived from the antigen. "Modulate", as used herein, refers to inducing, enhancing, suppressing, directing, or redirecting an immune response. Such agents include immunostimulatory agents, such as adjuvants, that stimulate (or boost) an immune response to an antigen but is not an antigen or derived from an antigen. There are several distinct types of immunomodulatory agents, which include, but are not limited to, Toll-like Receptor (TLR) agonists and Toll-like Receptor (TLR) antagonists. Such agents also include immunosuppressants. The immunomodulatory agent is selected from the group consisting of immune checkpoint modulators, Toll-like receptor (TLR) agonists, cell-based therapies, cytokines and cancer vaccines.

In some embodiments, the subject is determined to have an increased level and/or activity of a DNA damage process or DNA editing enzyme. In one aspect of this embodiment, the DNA editing enzyme is selected from the group consisting of activation induced cytidine deaminase (AID or AICDA), APOBEC2, APOBEC3A, APOBEC3C, APOBEC3D, APOBEC3F, APOBEC3G, APOBEC3H, APOBEC4, a Type 1 Topoisomerase, a Type 2 Topoisomerase, Recombination Activating Gene 1 (RAG 1), and Recombination Activating Gene 2 (RAG2).

In some embodiments, blood cells obtained from the subject have been determined to have a detectable level of activation-induced cytidine deaminase (AID).

In some embodiments, B cells obtained from the subject have been determined to have a detectable level of activation-induced cytidine deaminase (AID).

In some embodiments, the detectable level of activation-induced cytidine deaminase (AID) is statistically significantly higher than the level of AID expressed in unactivated B-cells or normal non-immune cells from a healthy subject.

Methods of Administration and Dosage Forms

The precise amount of compound administered to provide an "effective amount" to the subject will depend on the mode of administration, the type, and severity of the disease, and on the characteristics of the subject, such as general health, age, sex, body weight, and tolerance to drugs. The skilled artisan will be able to determine appropriate dosages depending on these and other factors. When administered in combination with other therapeutic agents, e.g., when administered in combination with an anti-cancer agent, an "effective amount" of any additional therapeutic agent(s) will depend on the type of drug used. Suitable dosages are known for approved therapeutic agents and can be adjusted by the skilled artisan according to the condition of the subject, the type of condition(s) being treated and the amount of a compound of the application and a PARP inhibitor being used by following, for example, dosages reported in the literature and recommended in the *Physician's Desk Reference* (57th ed., 2003).

The term "effective amount" means an amount when administered to the subject which results in beneficial or desired results, including clinical results, e.g., inhibits, suppresses or reduces the symptoms of the condition being treated in the subject as compared to a control. For example, a therapeutically effective amount can be given in unit dosage form (e.g., 0.1 mg to about 50 g per day, alternatively from 1 mg to about 5 grams per day).

The terms "administer", "administering", "administration", and the like, as used herein, refer to methods that may be used to enable delivery of compositions to the desired site of biological action. These methods include, but are not limited to, intraarticular (in the joints), intravenous, intramuscular, intratumoral, intradermal, intraperitoneal, subcutaneous, orally, topically, intrathecally, inhalationally, transdermally, rectally, and the like. Administration techniques that can be employed with the agents and methods described herein are found in e.g., Goodman and Gilman, *The Pharmacological Basis of Therapeutics*, current ed.; Pergamon; and Remington's, *Pharmaceutical Sciences* (current edition), Mack Publishing Co., Easton, Pa.

The particular mode of administration and the dosage regimen will be selected by the attending clinician, taking into account the particulars of the case (e.g., the subject, the disease, the disease state involved, the particular treatment). Treatment can involve daily or multi-daily or less than daily (such as weekly or monthly etc.) doses over a period of a few days to months, or even years. However, a person of ordinary skill in the art would immediately recognize appropriate and/or equivalent doses looking at dosages of approved compositions for treating a RAD51 mediated disease using the disclosed RAD51 inhibitors for guidance.

The compounds or the corresponding pharmaceutical compositions taught herein and the PARP inhibitor or a pharmaceutically acceptable salt thereof or a pharmaceutical composition comprising a PARP inhibitor can be administered to a patient in a variety of forms depending on the selected route of administration, as will be understood by those skilled in the art. The compounds of the present application and the PARP inhibitors may be administered, for example, by oral, parenteral, buccal, sublingual, nasal, rectal, patch, pump or transdermal administration and the pharmaceutical compositions formulated accordingly. Parenteral administration includes intravenous, intraperitoneal, subcutaneous, intramuscular, transepithelial, nasal, intrapulmonary, intrathecal, rectal and topical modes of administration. Parenteral administration can be by continuous infusion over a selected period of time.

The pharmaceutical composition of the application is formulated to be compatible with its intended route of administration. In some embodiments, the composition is formulated in accordance with routine procedures as a pharmaceutical composition adapted for intravenous, subcutaneous, intramuscular, oral, intranasal, or topical administration to human beings. In some embodiments, the pharmaceutical composition is formulated for intravenous administration.

In some embodiments for oral therapeutic administration, a compound of the present application and the PARP inhibitors may be incorporated with excipient and used in the form of ingestible tablets, buccal tablets, troches, capsules, elixirs, suspensions, syrups, wafers, and the like.

In some embodiments for parenteral administration, solutions of a compound of the present application and the PARP inhibitors can generally be prepared in water suitably mixed with a surfactant such as hydroxypropylcellulose. Dispersions can also be prepared in glycerol, liquid polyethylene glycols, DMSO and mixtures thereof with or without alcohol, and in oils. Under ordinary conditions of storage and use, these preparations contain a preservative to prevent the growth of microorganisms.

In some embodiments for injectable use, sterile aqueous solutions or dispersion of, and sterile powders of, a compound described herein for the extemporaneous preparation of sterile injectable solutions or dispersions are appropriate.

EXAMPLES

Abbreviations

Ac acetyl
ACN acetonitrile
aq aqueous
Bn benzyl
Boc tert-butoxycarbonyl
br. broad
d doublet (only when used within 1H NMR spectra)
DCM dichloromethane
DIEA (DIPEA) diisopropylethylamine
DMA dimethylacetamide
DMAP 4-dimethylaminopyridine
DMF N,N-dimethylformamide
DMSO dimethylsulfoxide
dppf 1,1'-bis(diphenylphosphino) ferrocene
eq equivalent
EtOAc ethyl acetate
hr hour
HBTU N,N,N,N',-tetramethyl-O-(1H-benzotriazol-1-yl) uronium hexafluorophosphate
HPLC high performance liquid chromatography
LC-MS liquid chromatography coupled to mass spectrometry
m multiplet
MS ESI mass spectra, electrospray ionization
NBS N-bromosuccinimide
NMR nuclear magnetic resonance
prep preparative
Py pyridine
s singlet
sat saturated
SFC supercritical fluid chromatography
t triplet
TEA triethylamine
TFA trifluoroacetic acid
THF tetrahydrofuran
TLC thin layer chromatography
Tol toluene

| General Method | Reaction Name |
|---|---|
| A | Substitution Reaction |
| B | Suzuki Reaction A |
| C | Deprotection of Boc group A (TFA) |
| D | Acylation Reaction |
| E | Urea Formation |
| F | Deprotection of Boc group B (HCl) |
| G | Reduction with Fe |
| H | Carbamate Formation |
| I | Hydrogenation |
| J | Bromination |
| K | Suzuki Reaction B |
| L | Thionation |
| M | Cyclization |
| N | Coupling Reaction |
| O | Hydrolysis Reaction |

Example 1. Synthesis of Compounds Compound 67A and Compound 67B

Compounds of the present application can be prepared according to the schemes, methods, and examples described in US 20190077799. The procedures below describe the synthesis of compounds Compound 67A and Compound 67B.

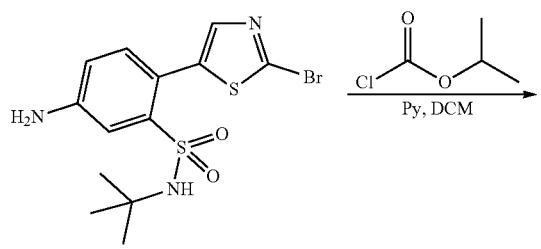

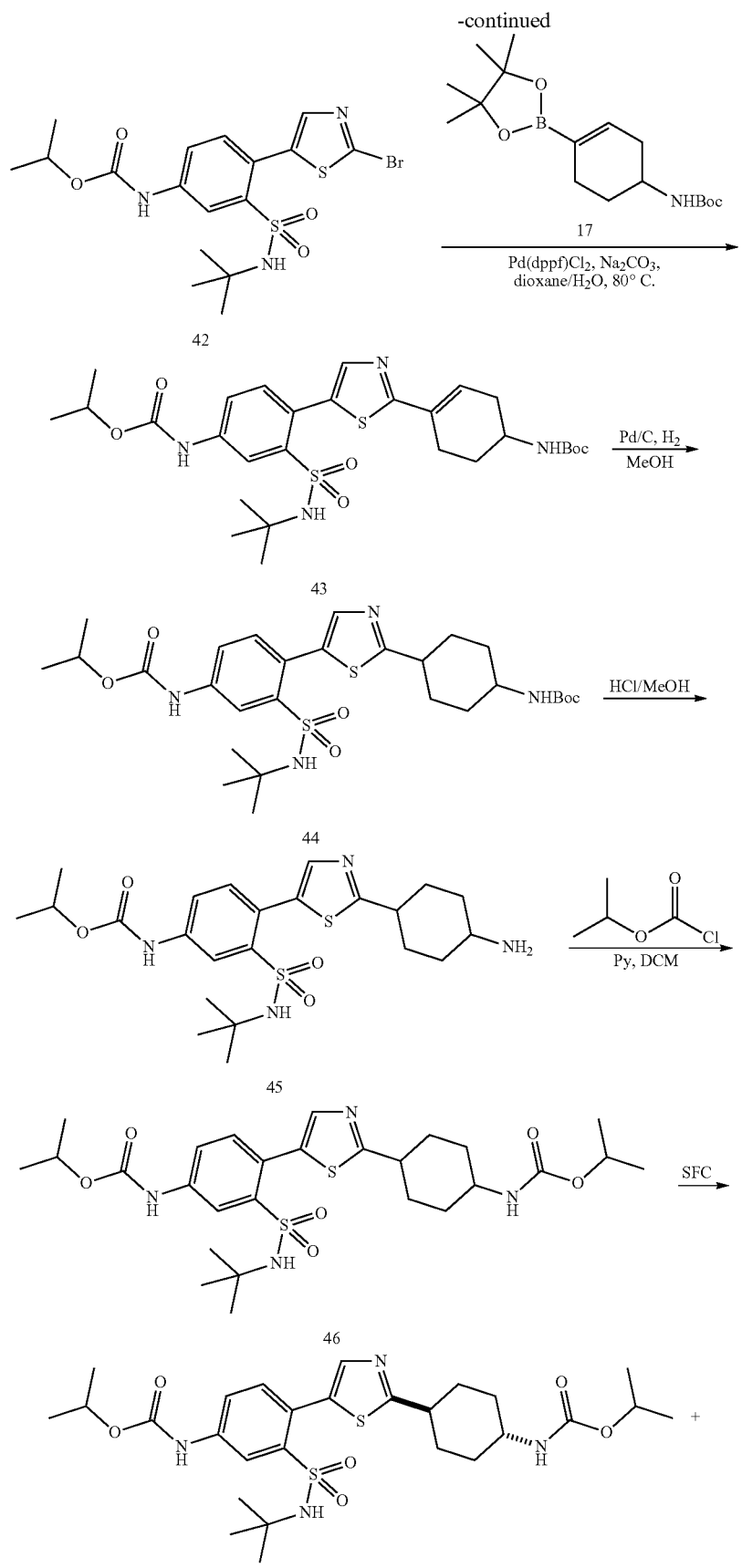
Ex. 67A

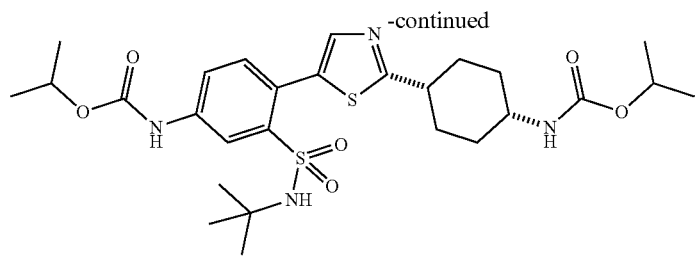
Ex. 67B
Preparation of compound 42
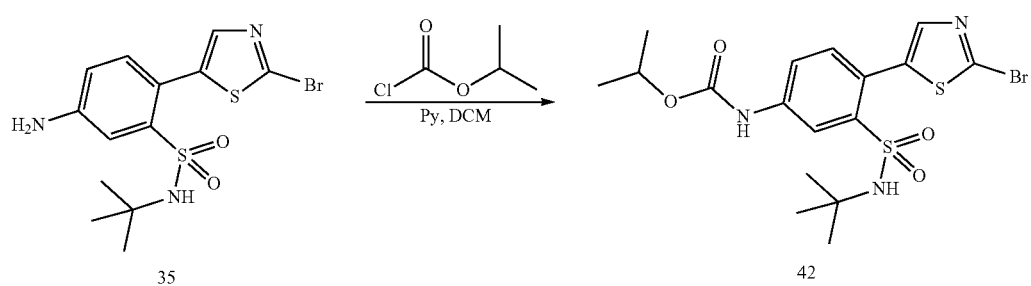
General Method D, isopropyl N-[4-(2-bromothiazol-5-yl)-3-(tert-butylsulfamoyl) phenyl]carbamate. ESI [M+H]=476.0/478.0
Preparation of Compound 43
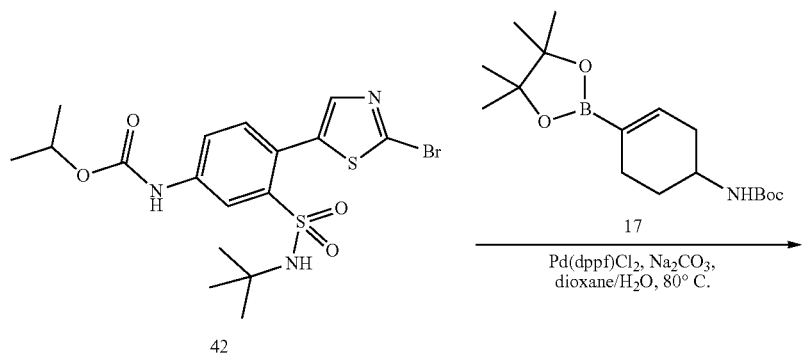
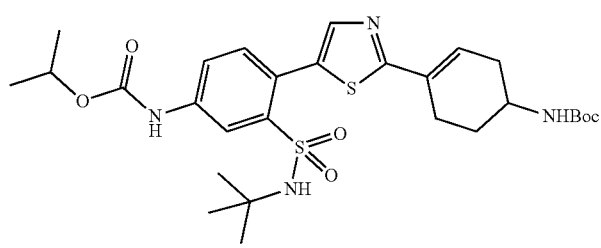

General Method B, isopropyl N-[4-[2-[4-(tert-butoxycarbonylamino)cyclohexen-1-yl]thiazol-5-yl]-3-(tert-butylsulfamoyl)phenyl]carbamate.
ESI [M+H]=593.3

Preparation of Compound 44

General Method I, isopropyl N-[4-[2-[4-(tert-butoxycarbonylamino)cyclohexyl] thiazol-5-yl]-3-(tert-butylsulfamoyl)phenyl]carbamate.
ESI [M+H]=595.3

Preparation of Compound 45

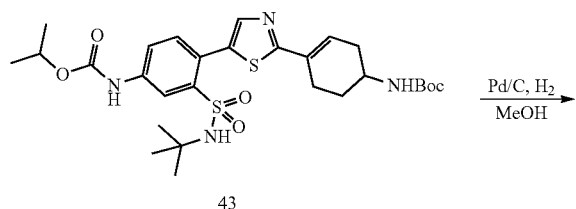

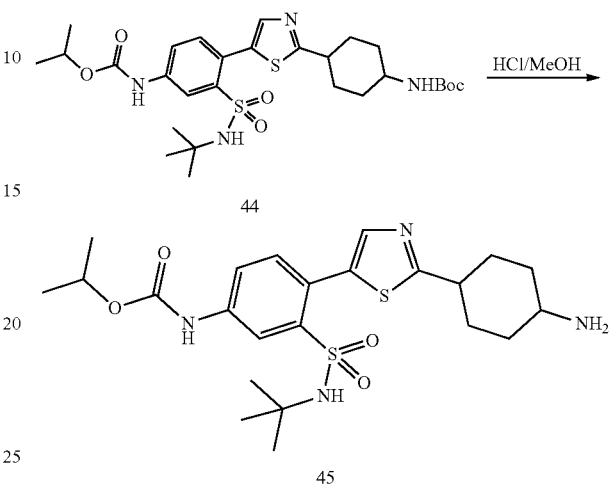

General Method F, isopropyl N-[4-[2-(4-aminocyclohexyl) thiazol-5-yl]-3-(tert-butylsulfamoyl)phenyl]carbamate. ESI [M+H]=495.2

Preparation of Compound 46

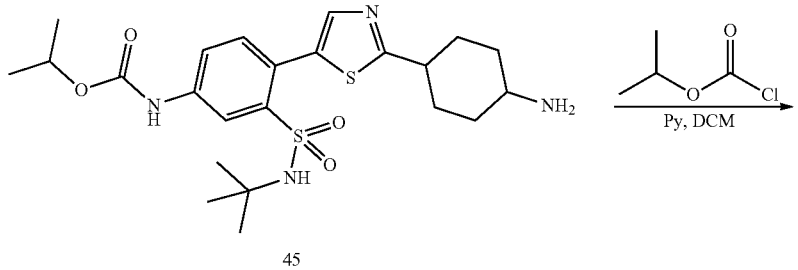

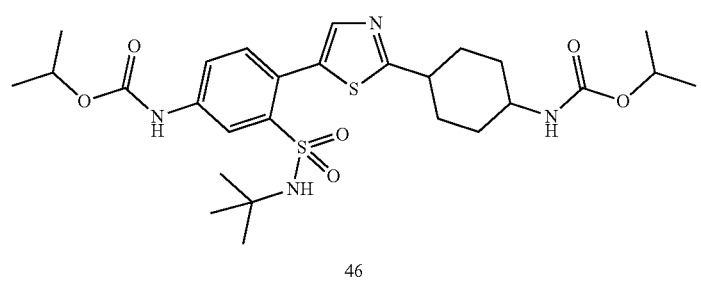

General Method D, isopropyl N-[3-(tert-butylsulfamoyl)-4-[2-[4-(isopropoxycarbonylamino)cyclohexyl]thiazol-5-yl]phenyl]carbamate. ESI [M+H]=581.2

Preparation of Compound 67A and Compound 67B.

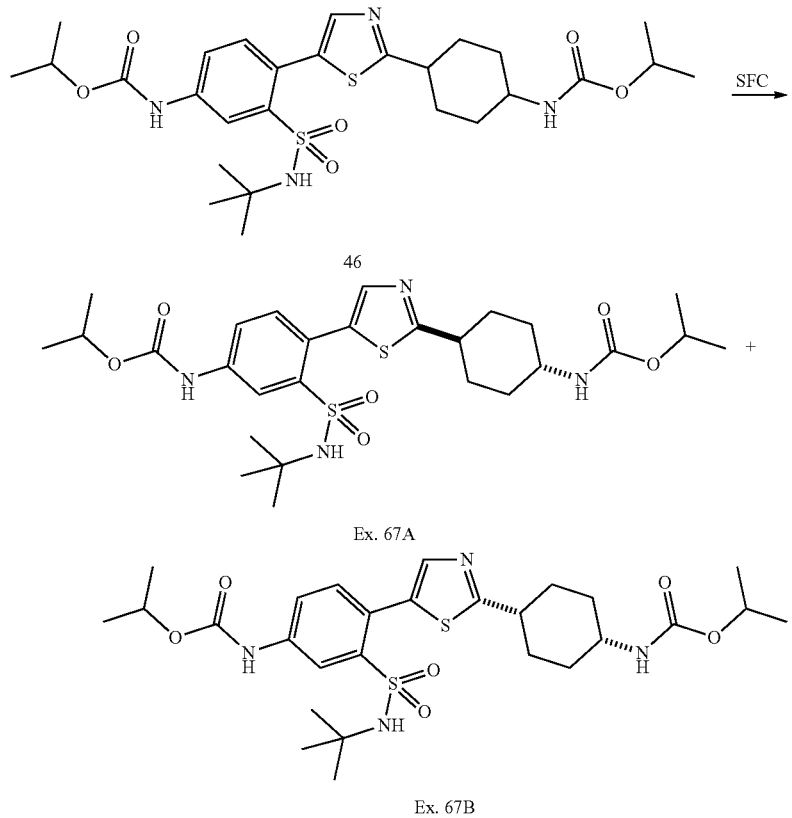

Compound 46 was separated by SFC (Instrument: Thar SFC80 preparative SFC; Column: ChiralpakAD-H 250*30 mm i.d. 5u; Mobile phase: A for $CO_2$ and B for IPA(0.1% $NH_3H_2O$); Gradient: B %=30%; Flow rate: 70 g/min; Wavelength: 220 nm; Column temperature: 40° C.; System back pressure: 100 bar; Cycle time: 8 min; Injection amount: 3 mg per injection); and then purified by prep-HPLC (Column: Agela Durashell C18 150*25 5u; mobile phase: [water(0.1% TFA)-ACN]; B %: 55%-85%,12 min), trans-isopropylN-[3-(tert-butylsulfamoyl)-4-[2-[4-(isopropoxycarbonylamino)cyclohexyl]thiazol-5-yl]phenyl]carbamate Compound 67A (5.76 mg, 100% purity) and cis-isopropylN-[3-(tert-butylsulfamoyl)-4-[2-[4-(isopropoxycarbonylamino) cyclohexyl]thiazol-5-yl]phenyl]carbamate Compound 67B (3.95 mg, 100% purity) were obtained as a pale yellow solid.

Trans-isopropylN-[3-(tert-butylsulfamoyl)-4-[2-[4-(isopropoxycarbonylamino)cyclohexyl]thiazol-5-yl]phenyl]carbamate (Compound S12)

$^1$H NMR (400 MHz, METHANOL-d4) δ=8.37 (d, J=2.3 Hz, 1H), 7.75 (s, 1H), 7.69 (dd, J=2.2, 8.4 Hz, 1H), 7.40 (d, J=8.3 Hz, 1H), 5.01 (td, J=6.3, 12.5 Hz, 1H), 4.86-4.82 (m, 1H), 3.52-3.42 (m, 1H), 3.04 (tt, J=3.5, 12.0 Hz, 1H), 2.35-2.19 (m, 2H), 2.15-1.99 (m, 2H), 1.72 (dq, J=3.0, 12.9 Hz, 2H), 1.43 (dq, J=3.3, 12.6 Hz, 2H), 1.34 (d, J=6.2 Hz, 6H), 1.25 (br d, J=6.1 Hz, 6H), 1.14 (s, 9H). ESI [M+H]=581.2.

Cis-isopropylN-[3-(tert-butylsulfamoyl)-4-[2-[4-(isopropoxycarbonylamino)cyclohexyl]thiazol-5-yl]phenyl]carbamate (Compound S13)

$^1$H NMR (400 MHz, METHANOL-d4) δ=8.37 (d, J=2.2 Hz, 1H), 7.76 (s, 1H), 7.70 (dd, J=2.2, 8.3 Hz, 1H), 7.40 (d, J=8.3 Hz, 1H), 5.01 (td, J=6.3, 12.5 Hz, 1H), 4.84 (br s, 1H), 3.77 (br s, 1H), 3.23-3.15 (m, 1H), 2.05-1.98 (m, 4H), 1.89-1.72 (m, 4H), 1.34 (d, J=6.2 Hz, 6H), 1.25 (d, J=6.1 Hz, 6H), 1.16 (s, 9H). ESI [M+H]=581.2

Example 2. Compound Primary Screening

Background

Primary screening was a phenotypic screen that utilized the synthetic lethal interaction between AID and RAD51 to identify compounds that were both potent and on target. AID expressing cells are dependent upon RAD51 for survival; inhibiting RAD51 in AID positive cells results in a cytotoxic effect. Based on such an effect, compounds that were potent in AID positive cells and were significantly less potent in AID negative cells were identified.

Materials and Supplies

Plastic ware and consumables needed for this experiment include: Cell Culture media; Evaporation Buffer media; 100% DMSO; 96 well U-bottom sterile culture plates; 250 mL bottle; 1.5 mL Opaque amber epi tubes; Epi Tube rack; 300 mL reservoirs; 25 mL reservoir; 25 mL serological pipette tips; 5 mL serological pipette tips P1000 Pipette Tips; and P200 Pipette Tips.

Equipment needed for this experiment include: Viaflo 384 liquid handler; Eppendorf serological pipette; Eppendorf P1000 Pipette; and Eppendorf P200 Pipette Daudi Cell Culture and WI-38 Cell Cultures were also needed for this experiment.

Lastly, compounds (e.g., the compounds of this application) to be tested are needed.

Procedure

All steps were performed in a sterile environment inside the Biosafety cabinet.

The first step was to set up a cell killing assay in the Daudi cell line (AID positive). A 96 well u-bottom plate was prepared by writing the experiment number, plate number, date and initials in the top right corner of the plate lid. With a sterile 300 ml reservoir, and 25 ml serological pipette, evaporation buffer media was pipetted into reservoir in 25 ml increments. Using the liquid handler, 150 ul of evaporation buffer media was pipetted from reservoir into rows A and H, and Columns 1 and 12 of the 96 well u-bottom plate. Cell cultures were counted to obtain the density of cells per ml, and the culture viability. The cell density information was used to obtain 1,000,000 cells from culture using a 5 mL serological pipette into an epi tube. The cell density information from the culture was used to calculate the number of cells and volume of media needed for the assay to seed 1250 cells in 130 ul of media per available culture well in the 96 well u-bottom plate. Rows B through F were used for cells (50 wells in total), with row G left for an empty media control. The calculation was overestimated by 10 mL to account for the dead volume in the 300 ml reservoir. Once the media volume was calculated, the appropriate volume of media was pipetted in 25 mL increments into the 250 mL bottle using a 25 mL serological pipette. The 250 ml bottle was capped tightly, and placed into a 37° C. water bath for 2 minutes. While the culture media was warming, 10 mL of fresh media was pipetted from the 500 mL culture media bottle into a sterile 25 mL reservoir. Using the Eppendorf multichannel pipette, 130 ul of media was piptted from the 25 mL reservoir into row G of the 96 well u-bottom plate. Once the 250 mL bottle of media was warmed, the volume of culture needed was pipetted into the bottle, and mixed gently with a 25 mL serological pipette as to not create bubbles, and then the contents of the bottle were pipetted into a new 300 mL reservoir. Using the liquid handler, 130 ul of culture was pipetted from the 300 mL reservoir into rows B through F of the 96 well u-bottom plate. Once the culture was added, the plate was placed into a 37° C. incubator until the compound master plate was prepared for use.

Two 96 well u-bottom plates were prepared by writing the master plate name in the upper right corner of the plate lid. Labeling one DMSO master and the other Media Master. The compounds of interest were obtained from the laboratory freezer, and placed into a 25 well storage box with a lid, and set the box aside. The compounds were vortexed after thawing but before use. Using an automatic multichannel pipette, 20 ul of 100% DMSO was pipetted into wells B3-B11 through G3-G11 of the DMSO master plate. For each compound on the master plate, 50 ul of the compound were pipetted in the appropriate well of row 2 (reference plate map to determine appropriate well). A serial dilution was prepared beginning by aspirating 20 ul from row 2 and mixing with row 3, repeating until row 11 was reached. Using the liquid handler, 194 ul of Daudi media was dispensed into wells B2-B11 through G2-G11 of the Media master plate. Using the liquid handler, 6 ul from the DMSO master plate was aspirated and dispensed into the media master plate, mixing 100 ul twice.

Compounds from master plate were then added to the culture plate. The culture plates were removed from the incubator, and set inside the biosafety cabinet. Using a liquid handler, 20 ul from wells B2 to B11 through G2 to G11 of master plate were aspirated, and dispensed into wells B2 to B11 through G2 to G11 of culture plate. This set was continued with each culture plate. Once the culture plates acquired their 20 ul of compound dilutions, they were placed back into the incubator, until their reads on Day 7 of experiment. Cell death was measured on Day 7 of the experiment using Cell-Titer Glo and a Promega Plate reader.

Percent cell death and $EC_{50}$ values were calculated by comparing the cell viability of the compound treated wells to the non-treated wells. Normalized RLU values were obtained by subtracting the media well values from each of the wells in the same column, and then dividing that value by the DMSO treated cells values. The percent kill was then calculated by subtracting the normalized RLU value from 1 and multiplying by 100. The average normalized percent kill value and standard error of the mean was then calculated. The kill values were then inputted into Prism with the corresponding standard errors. In Prism a non-linear regression line was plotted with the data points using a semi-log scale, and the $EC_{50}$ value was calculated. For compounds that showed good potency in the Daudi cell line, the assay was repeated using WI-38 cells (AID negative).

Screening Data

TABLE 1

Compounds of the Present Application

| Cmpd. No. | Structure | AID+ $EC_{50}$ (μM)<br>A = ≤0.1 μM<br>B = ≤1 μM<br>C = >1 μM<br>ND = Not Determined | AID− $EC_{50}$ (μM)<br>A = ≤0.1 μM<br>B = ≤1 μM<br>C = >1 μM<br>ND = Not Determined |
|---|---|---|---|
| 1 | 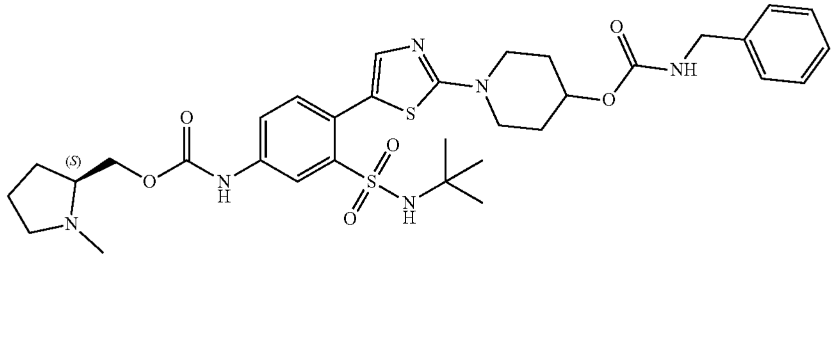 | C | ND |

TABLE 1-continued

Compounds of the Present Application

| Cmpd. No. | Structure | AID+ EC$_{50}$ (μM) A = ≤0.1 μM B = ≤1 μM C = >1 μM ND = Not Determined | AID− EC$_{50}$ (μM) A = ≤0.1 μM B = ≤1 μM C = >1 μM ND = Not Determined |
|---|---|---|---|
| 2 | 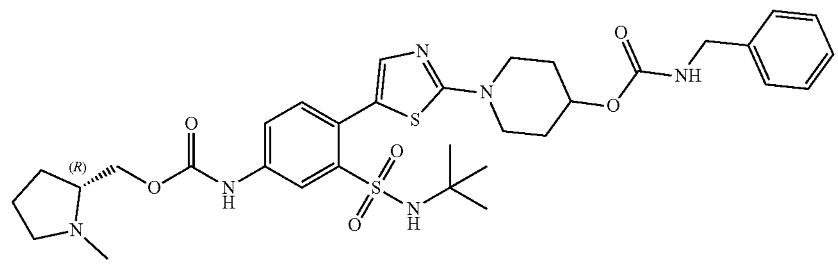 | C | ND |
| 3 | 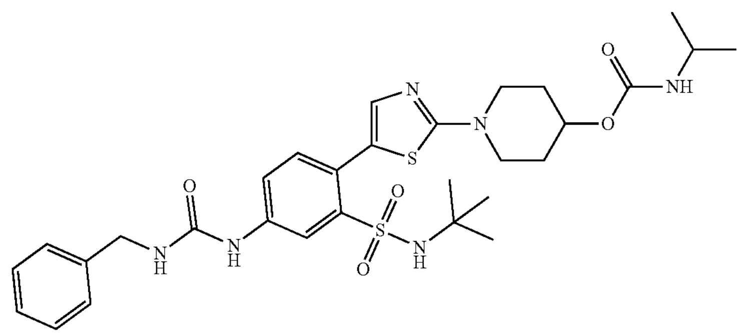 [SMILES: CC(C)NC(=O)OC1CCN(c2ncc(-c3ccc(NC(=O)NCc4ccccc4)cc3S(=O)(=O)NC(C)(C)C)s2)CC1] | A | C |
| 4 | 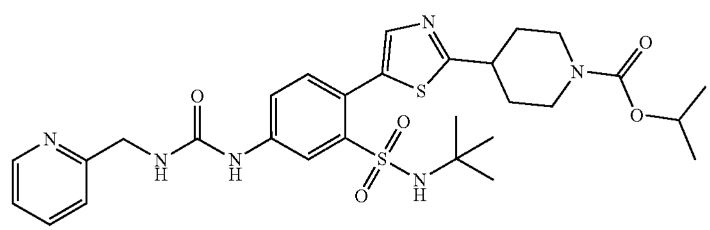 [SMILES: CC(C)OC(=O)N1CCC(c2ncc(-c3ccc(NC(=O)NCc4ccccn4)cc3S(=O)(=O)NC(C)(C)C)s2)CC1] | C | C |
| 5 | 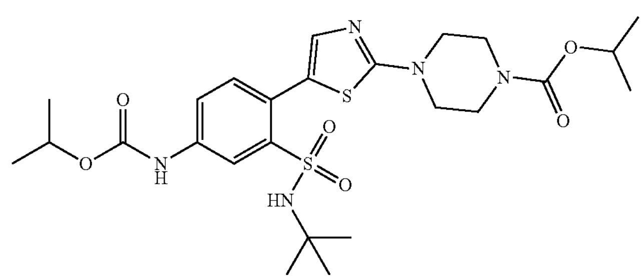 [SMILES: CC(C)OC(=O)Nc1ccc(-c2cnc(N3CCN(C(=O)OC(C)C)CC3)s2)c(S(=O)(=O)NC(C)(C)C)c1] | C | ND |
| 6 | 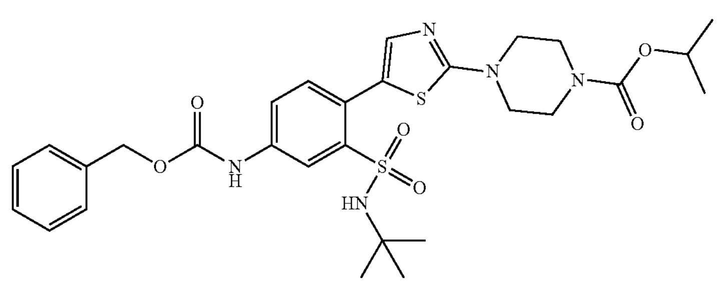 [SMILES: CC(C)OC(=O)N1CCN(c2ncc(-c3ccc(NC(=O)OCc4ccccc4)cc3S(=O)(=O)NC(C)(C)C)s2)CC1] | C | ND |

TABLE 1-continued

Compounds of the Present Application

| Cmpd. No. | Structure | AID+ EC$_{50}$ (µM)<br>A = ≤0.1 µM<br>B = ≤1 µM<br>C = >1 µM<br>ND = Not Determined | AID− EC$_{50}$ (µM)<br>A = ≤0.1 µM<br>B = ≤1 µM<br>C = >1 µM<br>ND = Not Determined |
|---|---|---|---|
| 7 | 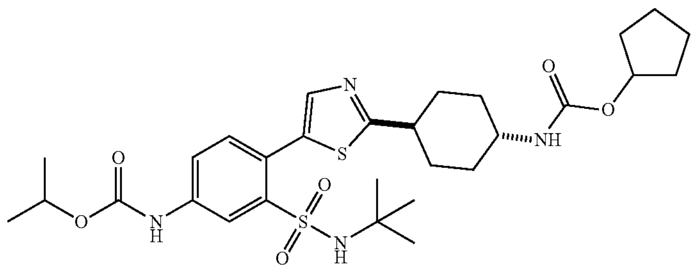 | B | ND |
| 8 | 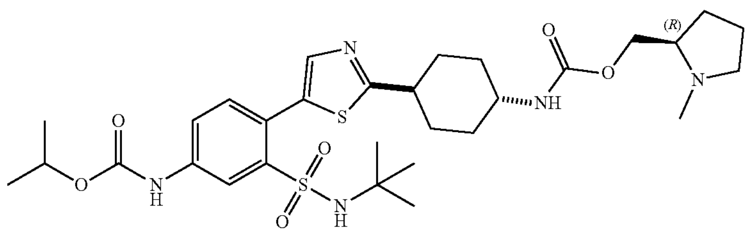 | C | ND |
| 9 | 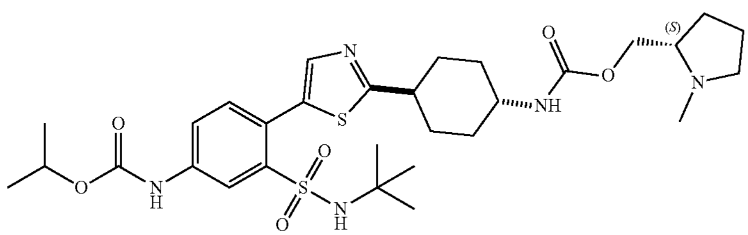 | B | ND |
| 10 | 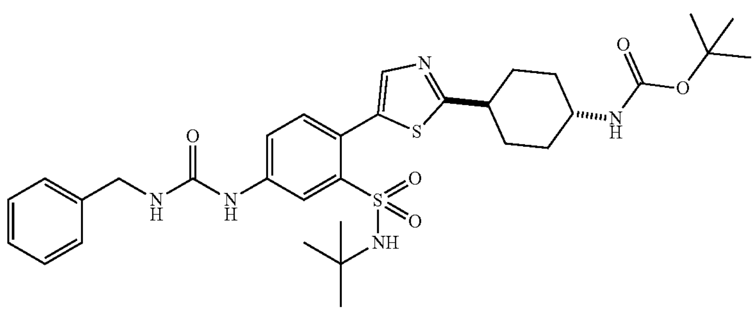 | A | C |
| 11 | 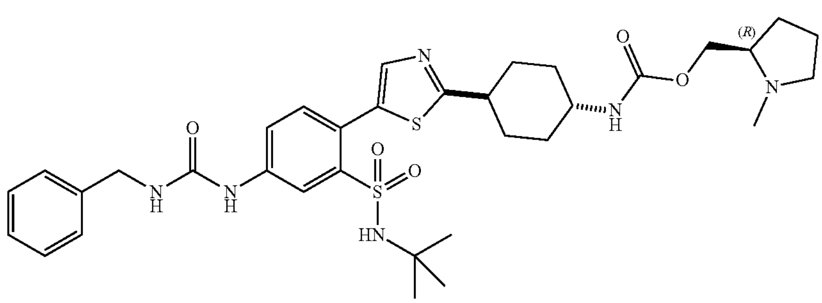 | B | ND |

TABLE 1-continued

Compounds of the Present Application

| Cmpd. No. | Structure | AID+ EC$_{50}$ (μM)<br>A = ≤0.1 μM<br>B = ≤1 μM<br>C = >1 μM<br>ND = Not Determined | AID− EC$_{50}$ (μM)<br>A = ≤0.1 μM<br>B = ≤1 μM<br>C = >1 μM<br>ND = Not Determined |
|---|---|---|---|
| 12 | 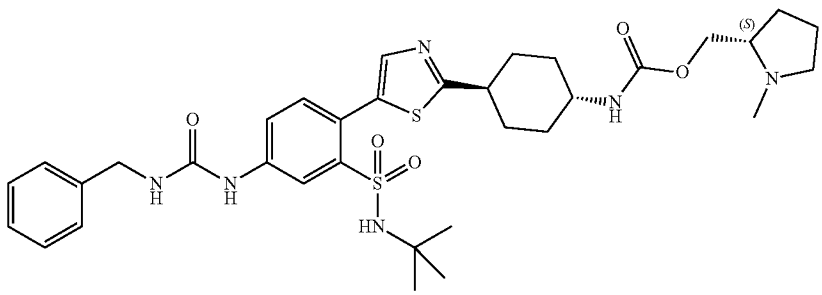 | B | ND |
| 13 | 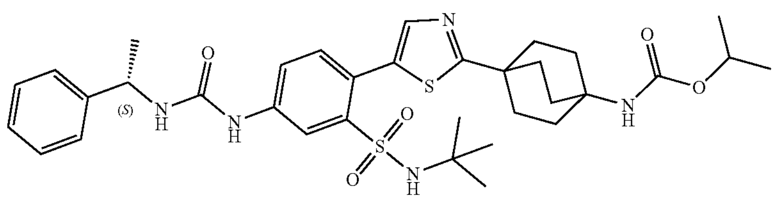 | A | C |
| 14 | 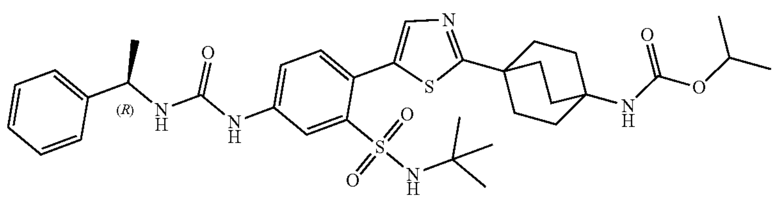 | A | C |
| 15 | 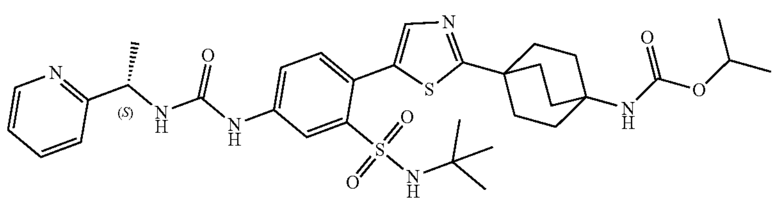 | A | C |
| 16 | 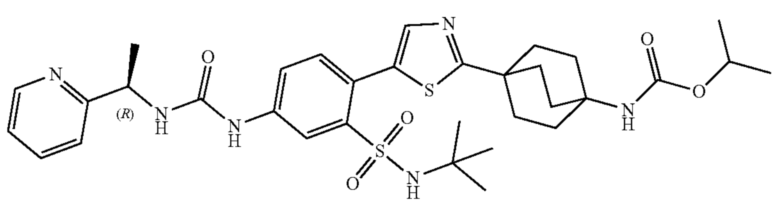 | A | C |
| 17 | 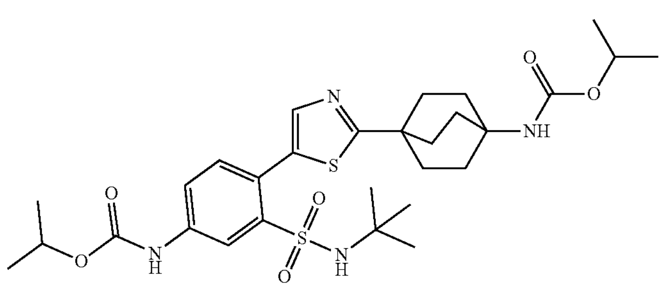 [SMILES: CC(C)OC(=O)Nc1ccc(-c2cnc(C34CCC(NC(=O)OC(C)C)(CC3)CC4)s2)c(S(=O)(=O)NC(C)(C)C)c1] | B | C |

TABLE 1-continued

Compounds of the Present Application

| Cmpd. No. | Structure | AID+ EC$_{50}$ (μM) A = ≤0.1 μM B = ≤1 μM C = >1 μM ND = Not Determined | AID− EC$_{50}$ (μM) A = ≤0.1 μM B = ≤1 μM C = >1 μM ND = Not Determined |
|---|---|---|---|
| 18 | 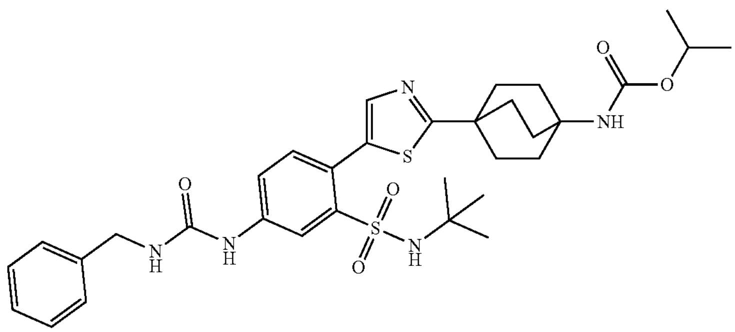 [SMILES: CC(C)OC(=O)NC12CCC(c3ncc(-c4ccc(NC(=O)NCc5ccccc5)cc4S(=O)(=O)NC(C)(C)C)s3)(CC1)CC2] | A | C |
| 19 | 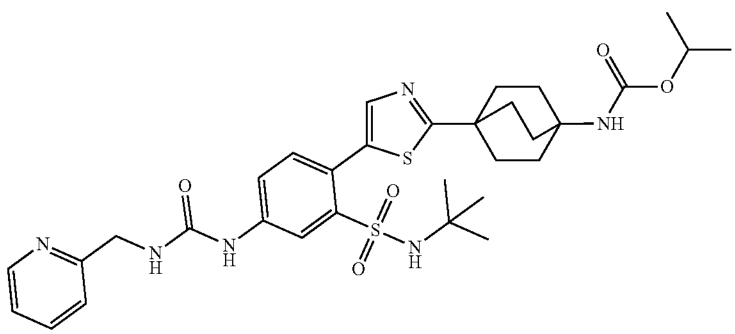 [SMILES: CC(C)OC(=O)NC12CCC(c3ncc(-c4ccc(NC(=O)NCc5ccccn5)cc4S(=O)(=O)NC(C)(C)C)s3)(CC1)CC2] | A | C |
| 20 | 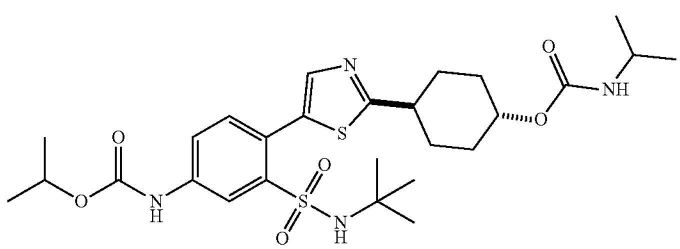 | C | ND |
| 21 | 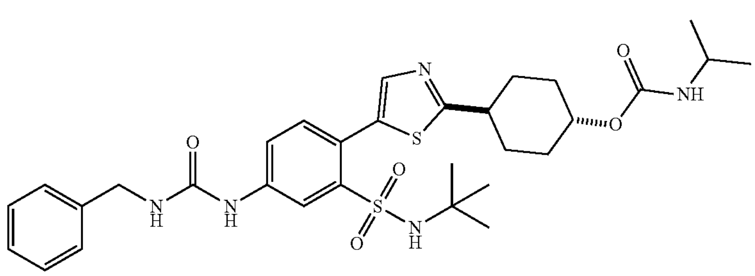 | A | ND |

TABLE 1-continued

Compounds of the Present Application

| Cmpd. No. | Structure | AID+ EC$_{50}$ (μM)<br>A = ≤0.1 μM<br>B = ≤1 μM<br>C = >1 μM<br>ND = Not Determined | AID− EC$_{50}$ (μM)<br>A = ≤0.1 μM<br>B = ≤1 μM<br>C = >1 μM<br>ND = Not Determined |
|---|---|---|---|
| 22 | 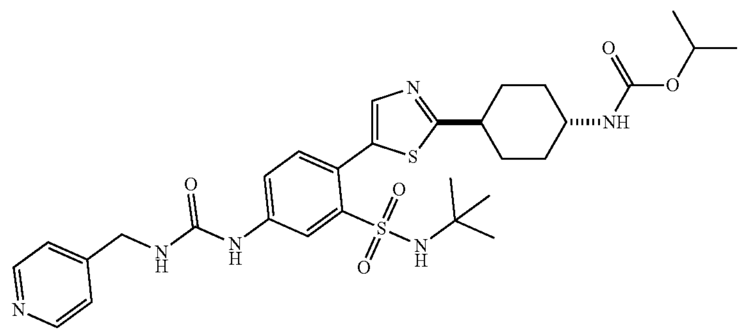 | B | ND |
| 23 | 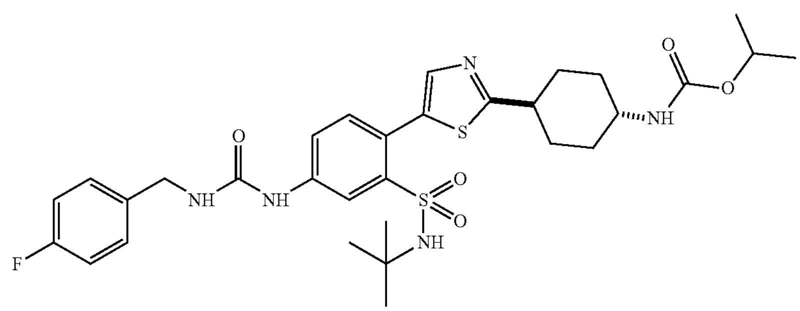 | A | ND |
| 24 | 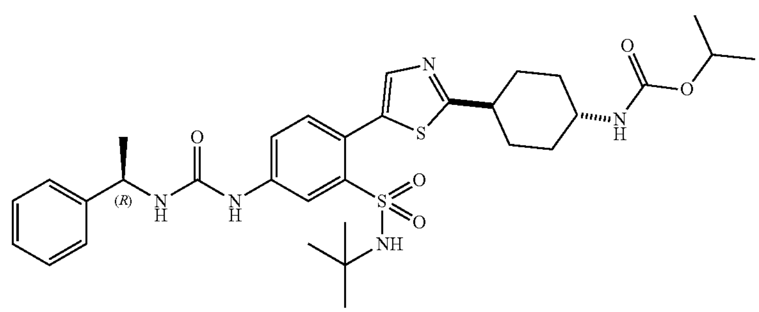 | A | C |
| 25 | 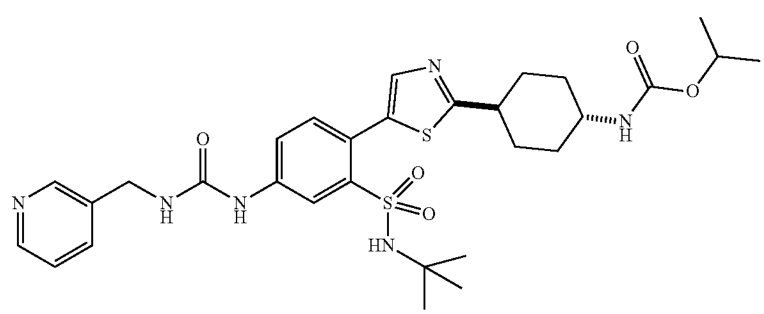 | A | ND |

TABLE 1-continued
Compounds of the Present Application
| Cmpd. No. | Structure | AID+ EC$_{50}$ (μM) A = ≤0.1 μM B = ≤1 μM C = >1 μM ND = Not Determined | AID− EC$_{50}$ (μM) A = ≤0.1 μM B = ≤1 μM C = >1 μM ND = Not Determined |
|---|---|---|---|
| 26 | 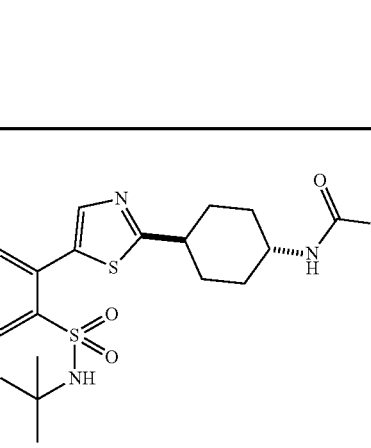 | A | C |
| 27 | 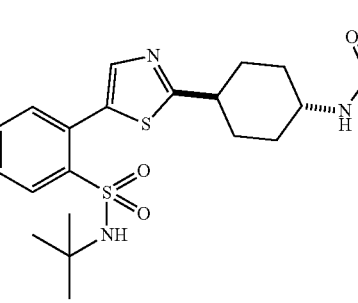 | A | C |
| 28 | 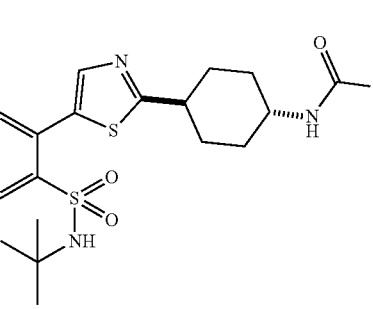 | A | ND |
| 29 | 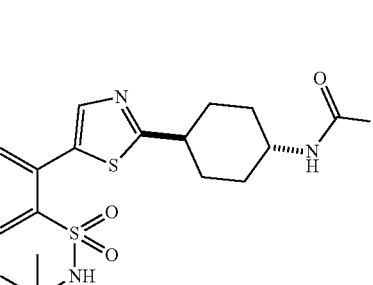 | A | C |

TABLE 1-continued

Compounds of the Present Application

| Cmpd. No. | Structure | AID+ EC$_{50}$ (μM)<br>A = ≤0.1 μM<br>B = ≤1 μM<br>C = >1 μM<br>ND = Not Determined | AID- EC$_{50}$ (μM)<br>A = ≤0.1 μM<br>B = ≤1 μM<br>C = >1 μM<br>ND = Not Determined |
|---|---|---|---|
| 30 | 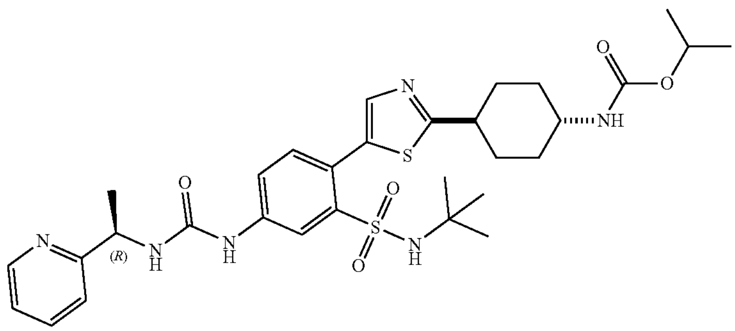 | A | C |
| 31 | 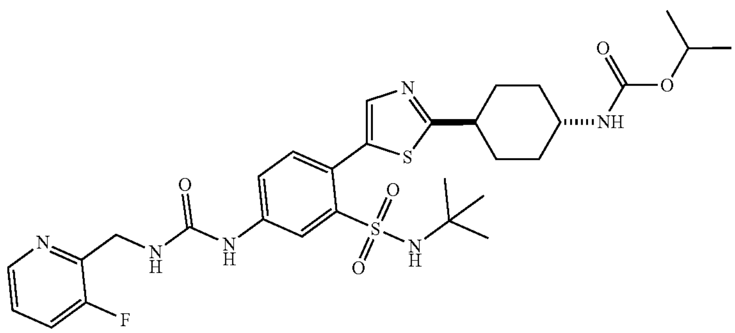 | A | C |
| 32 | 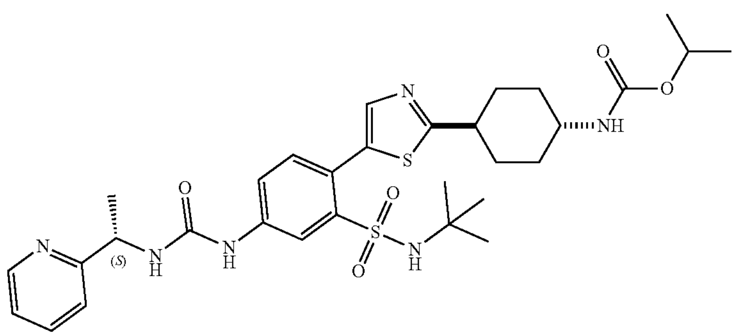 | A | C |
| 33 | 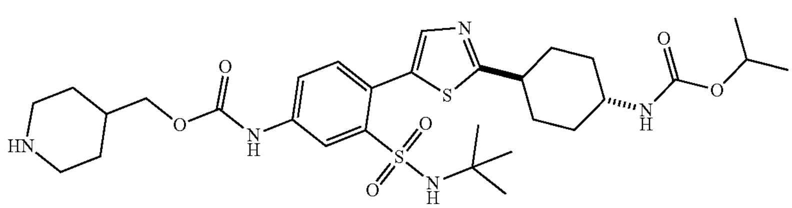 | C | ND |
| 34 | 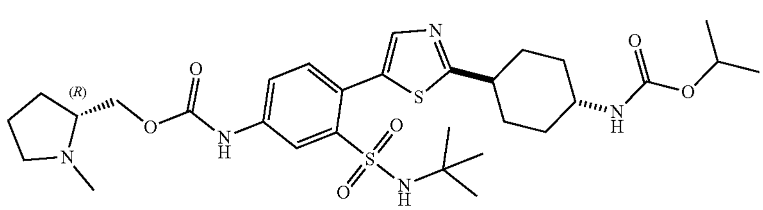 | B | ND |

TABLE 1-continued

Compounds of the Present Application

| Cmpd. No. | Structure | AID+ EC$_{50}$ (μM) A = ≤0.1 μM B = ≤1 μM C = >1 μM ND = Not Determined | AID− EC$_{50}$ (μM) A = ≤0.1 μM B = ≤1 μM C = >1 μM ND = Not Determined |
|---|---|---|---|
| 35 | 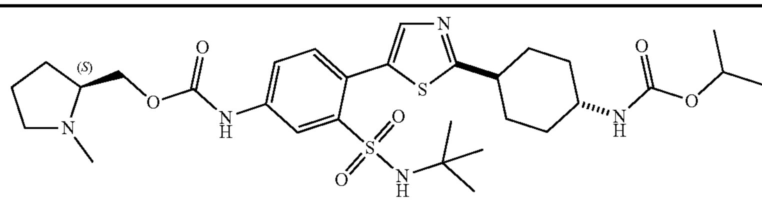 | B | ND |
| 36 | 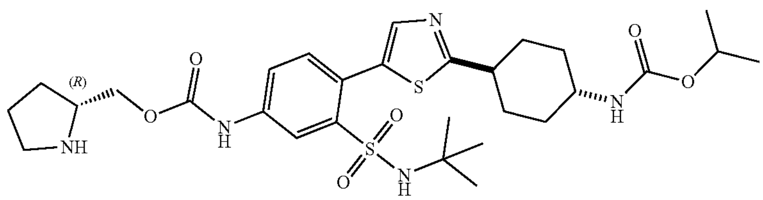 | B | ND |
| 37 | 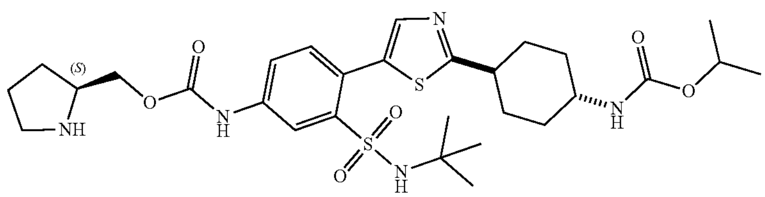 | B | ND |
| 38 | 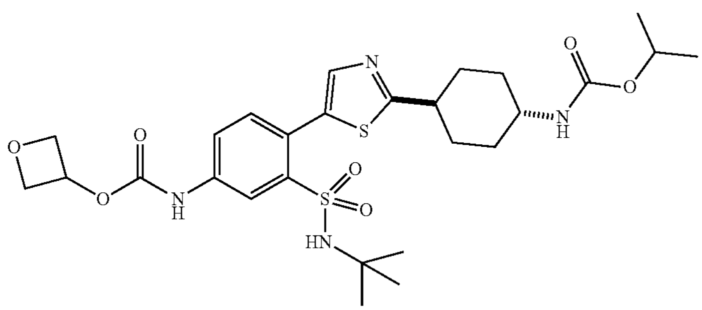 | A | C |
| 39 | 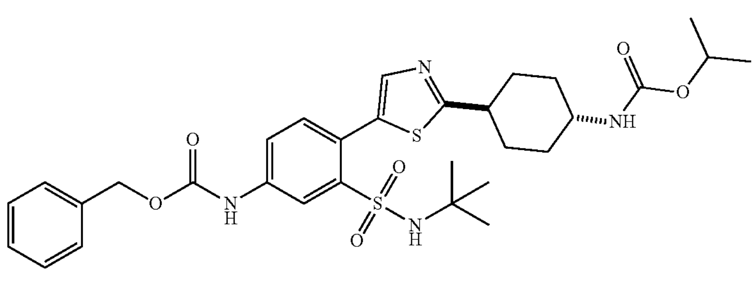 | A | C |
| 40 | 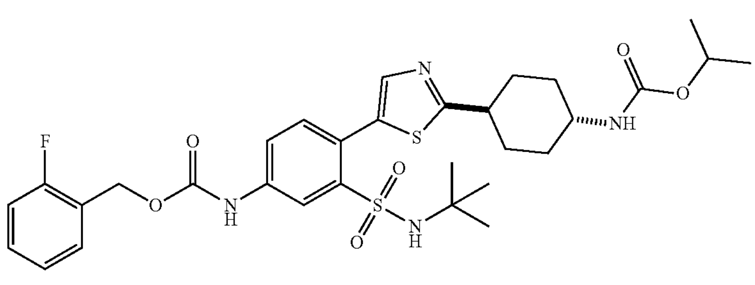 | A | C |

TABLE 1-continued

Compounds of the Present Application

| Cmpd. No. | Structure | AID+ EC$_{50}$ (μM) A = ≤0.1 μM B = ≤1 μM C = >1 μM ND = Not Determined | AID- EC$_{50}$ (μM) A = ≤0.1 μM B = ≤1 μM C = >1 μM ND = Not Determined |
|---|---|---|---|
| 41 | 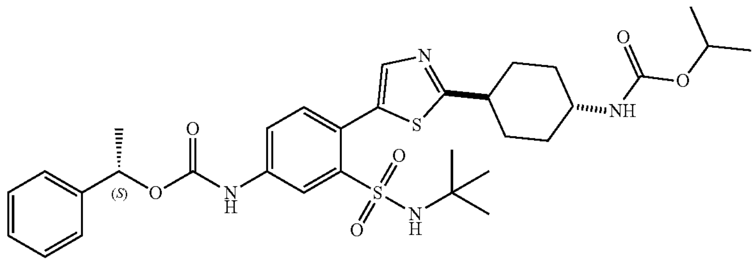 | A | C |
| 42 | 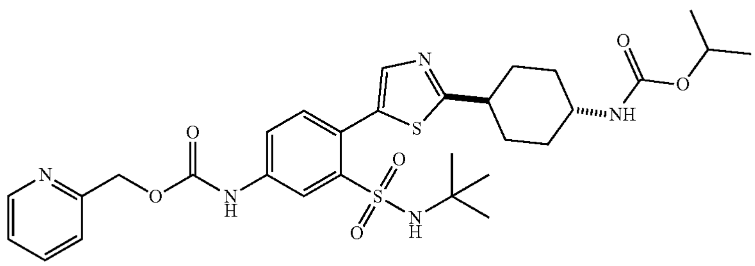 | A | C |
| 43 | 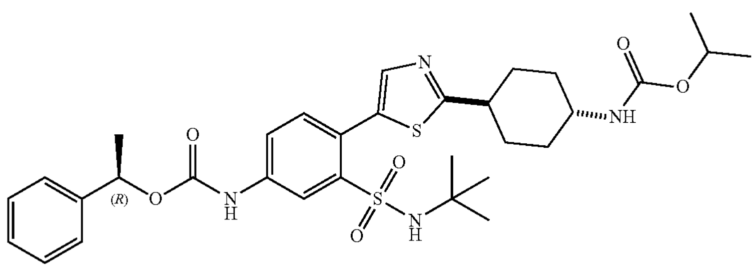 | B | C |
| 44 | 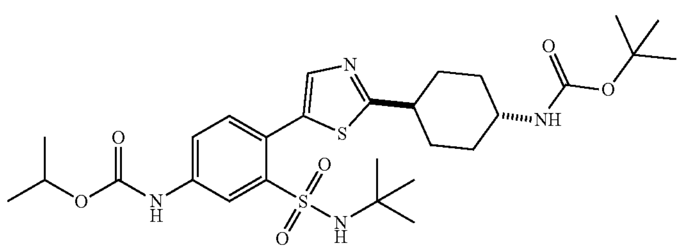 | C | ND |
| 45 | 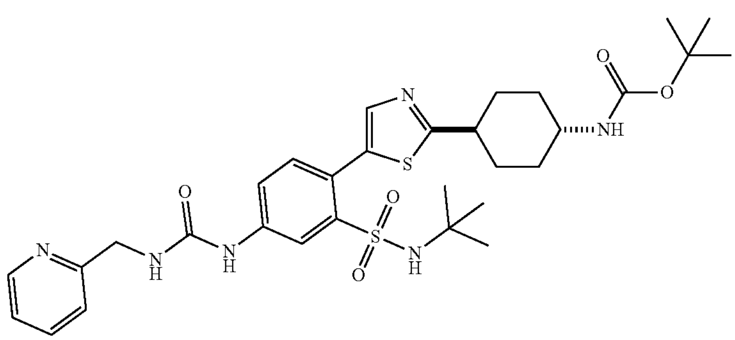 | A | ND |

TABLE 1-continued

Compounds of the Present Application

| Cmpd. No. | Structure | AID+ EC$_{50}$ (μM)<br>A = ≤0.1 μM<br>B = ≤1 μM<br>C = >1 μM<br>ND = Not Determined | AID− EC$_{50}$ (μM)<br>A = ≤0.1 μM<br>B = ≤1 μM<br>C = >1 μM<br>ND = Not Determined |
|---|---|---|---|
| 46 | 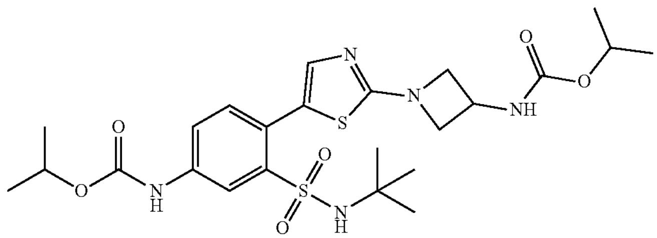 [SMILES: CC(C)OC(=O)Nc1ccc(-c2cnc(N3CC(NC(=O)OC(C)C)C3)s2)c(S(=O)(=O)NC(C)(C)C)c1] | C | C |
| 47 | 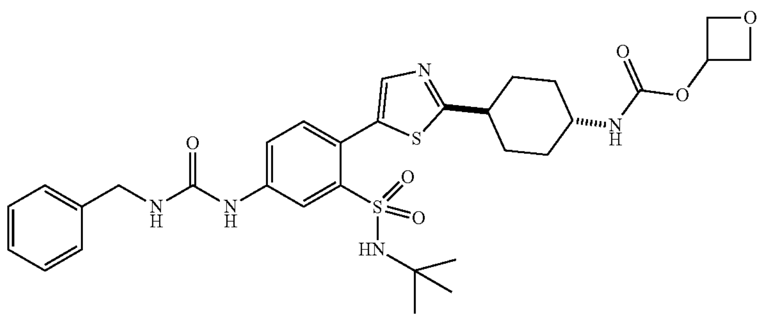 | A | C |
| 48 | 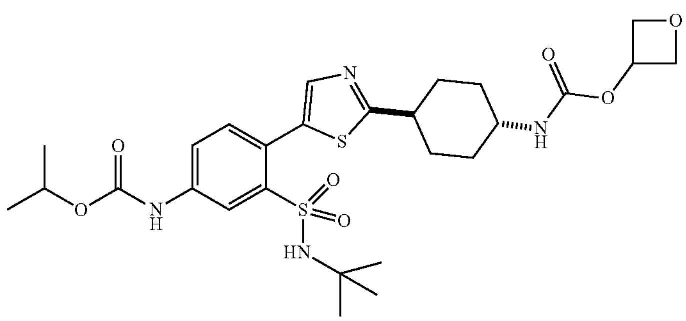 | B | C |
| 49 | 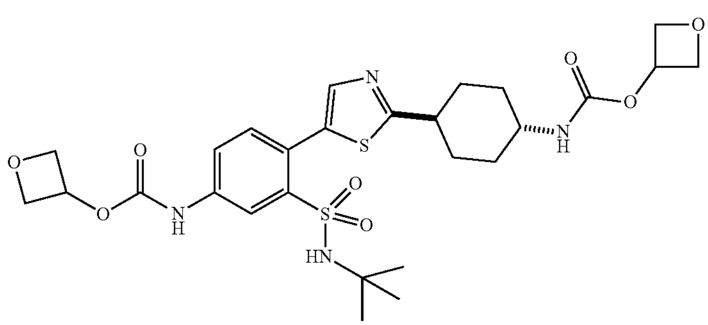 | B | C |

TABLE 1-continued

Compounds of the Present Application

| Cmpd. No. | Structure | AID+ EC$_{50}$ (μM) A = ≤0.1 μM B = ≤1 μM C = >1 μM ND = Not Determined | AID− EC$_{50}$ (μM) A = ≤0.1 μM B = ≤1 μM C = >1 μM ND = Not Determined |
|---|---|---|---|
| 50 | 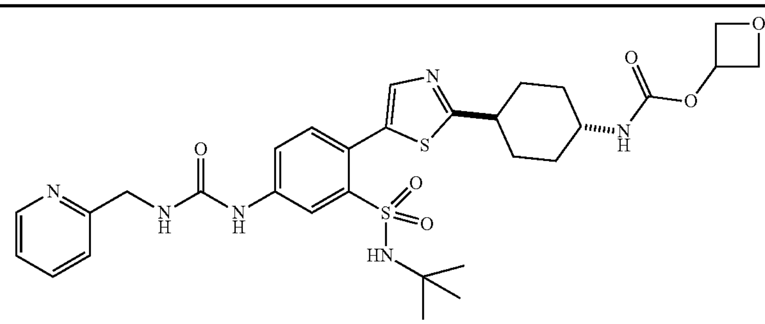 | A | C |
| 51 | 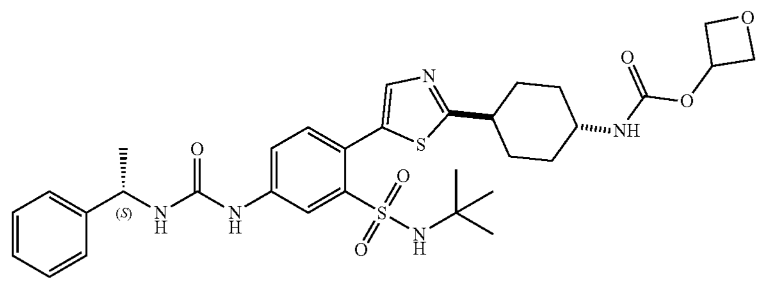 | A | C |
| 52 | 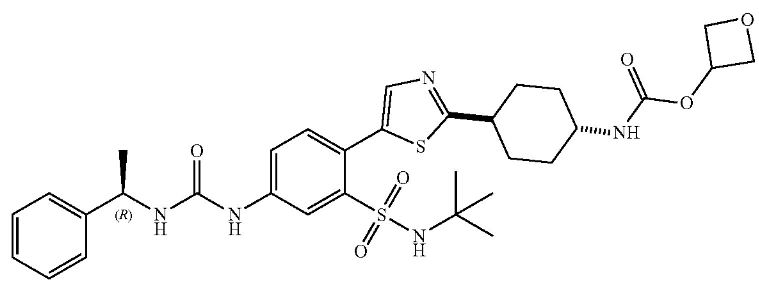 | A | C |
| 53 | 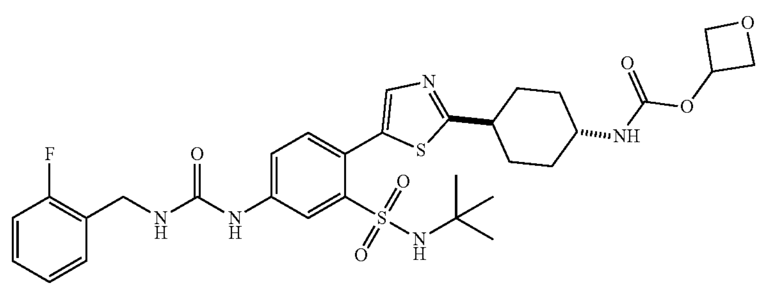 | A | C |
| 54 | 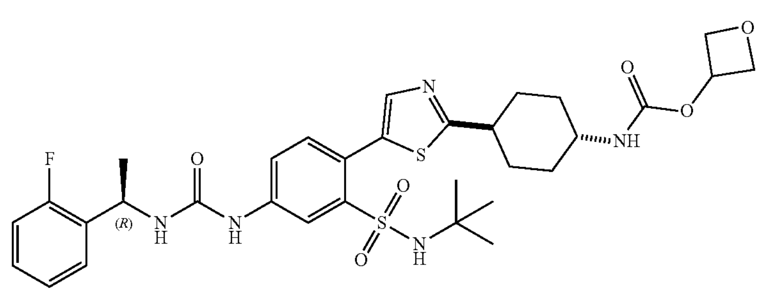 | A | C |

TABLE 1-continued

Compounds of the Present Application

| Cmpd. No. | Structure | AID+ EC$_{50}$ (μM) A = ≤0.1 μM B = ≤1 μM C = >1 μM ND = Not Determined | AID− EC$_{50}$ (μM) A = ≤0.1 μM B = ≤1 μM C = >1 μM ND = Not Determined |
|---|---|---|---|
| 55 | 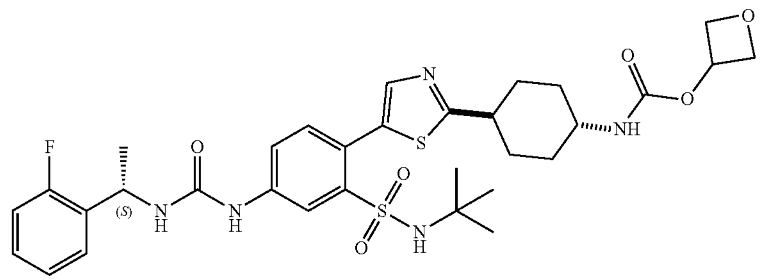 | A | C |
| 56 | 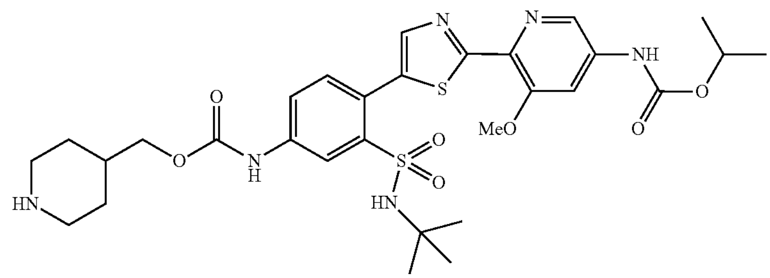 [SMILES: COc1cc(NC(=O)OC(C)C)cnc1-c1ncc(-c2ccc(NC(=O)OCC3CCNCC3)cc2S(=O)(=O)NC(C)(C)C)s1] | B | ND |
| 57 | 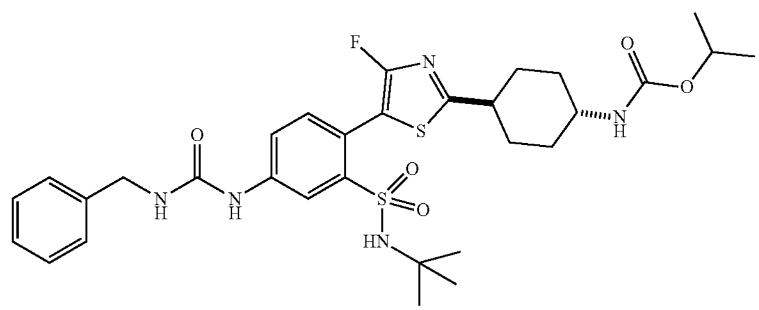 | A | C |
| 58 | 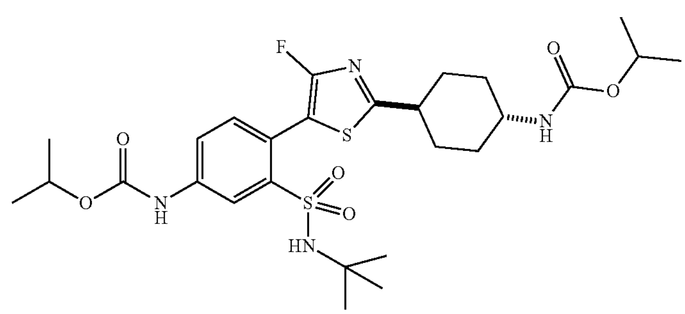 | B | C |
| 59 | 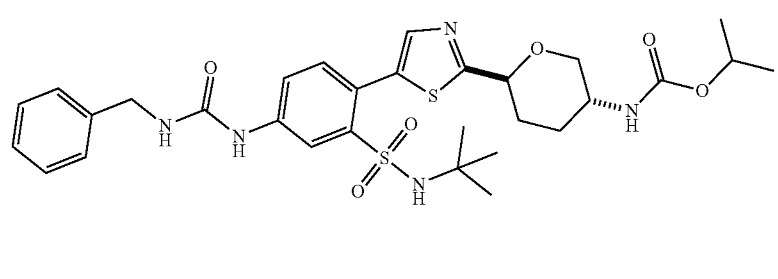 | A | C |

TABLE 1-continued

Compounds of the Present Application

| Cmpd. No. | Structure | AID+ EC$_{50}$ (μM) A = ≤0.1 μM B = ≤1 μM C = >1 μM ND = Not Determined | AID− EC$_{50}$ (μM) A = ≤0.1 μM B = ≤1 μM C = >1 μM ND = Not Determined |
|---|---|---|---|
| 59A | 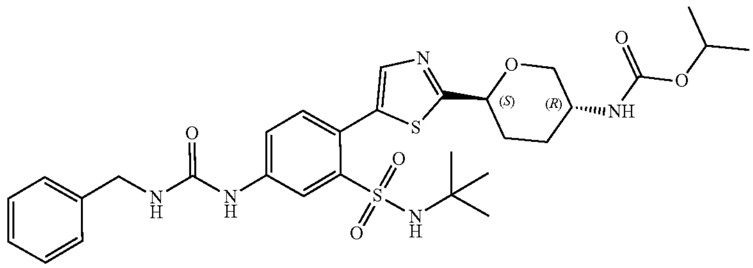 | B | C |
| 59B | 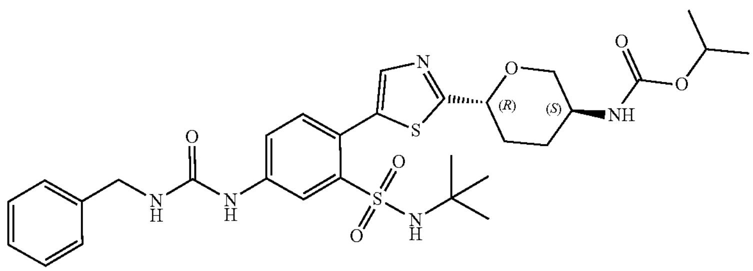 | A | C |
| 60 | 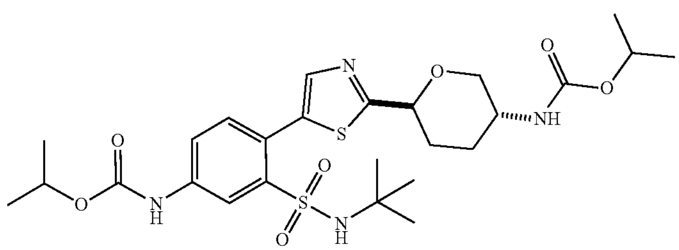 | B | C |
| 60A | 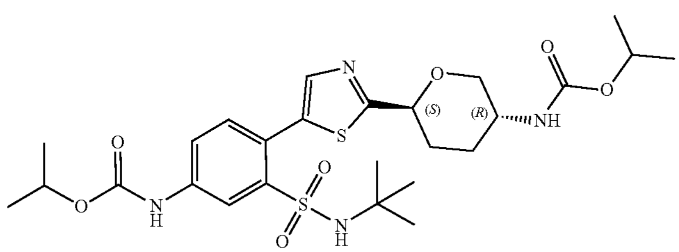 | C | C |
| 60B | 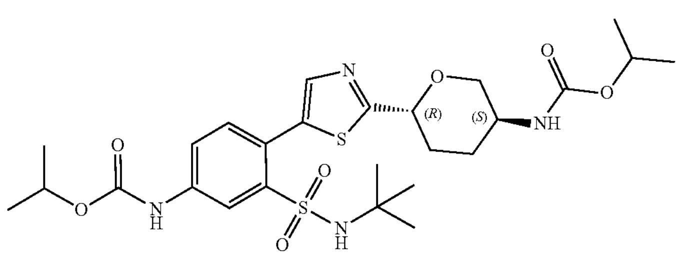 | B | C |

TABLE 1-continued

Compounds of the Present Application

| Cmpd. No. | Structure | AID+ EC$_{50}$ (μM) A = ≤0.1 μM B = ≤1 μM C = >1 μM ND = Not Determined | AID− EC$_{50}$ (μM) A = ≤0.1 μM B = ≤1 μM C = >1 μM ND = Not Determined |
|---|---|---|---|
| 61 | 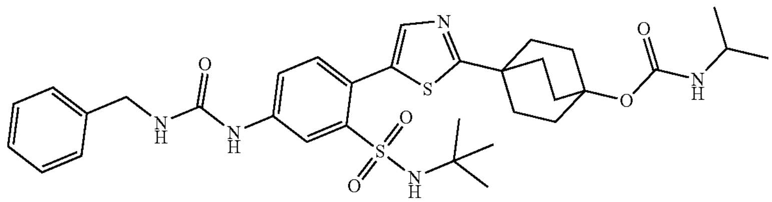 [SMILES: CC(C)NC(=O)OC12CCC(c3ncc(-c4ccc(NC(=O)NCc5ccccc5)cc4S(=O)(=O)NC(C)(C)C)s3)(CC1)CC2] | C | C |
| 62 | 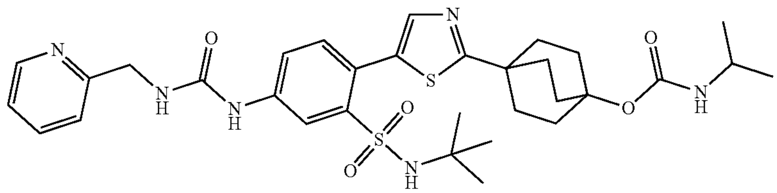 [SMILES: CC(C)NC(=O)OC12CCC(c3ncc(-c4ccc(NC(=O)NCc5ccccn5)cc4S(=O)(=O)NC(C)(C)C)s3)(CC1)CC2] | C | C |
| 63 | 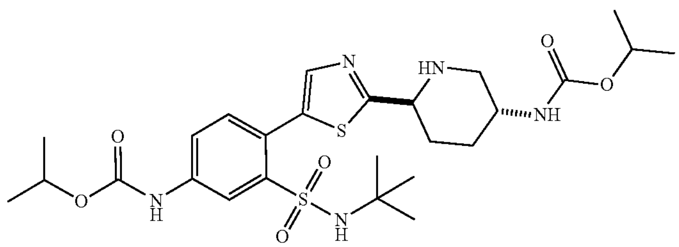 | B | ND |
| 64 | 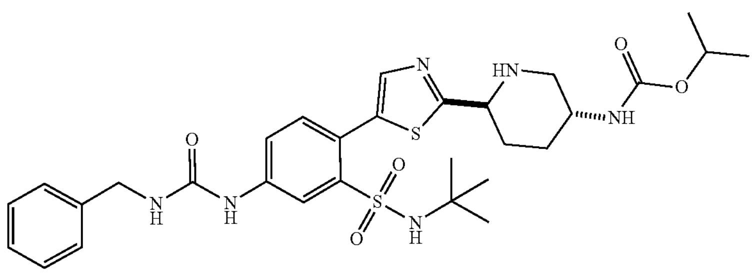 | A | C |
| 65 | 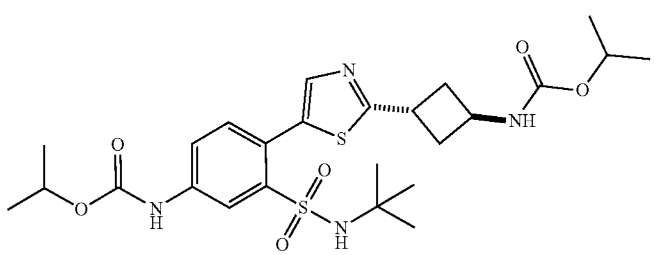 | B | C |
| 66A | 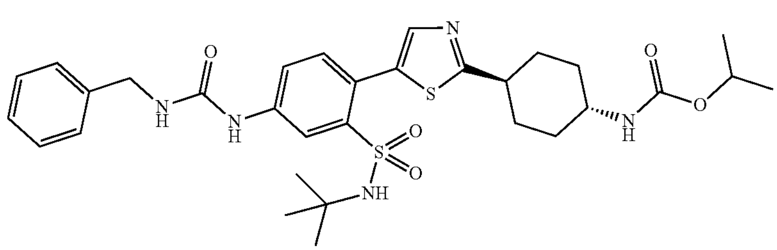 [SMILES: CC(C)OC(=O)N[C@H]1CC[C@H](c2ncc(-c3ccc(NC(=O)NCc4ccccc4)cc3S(=O)(=O)NC(C)(C)C)s2)CC1] | A | C |

TABLE 1-continued

Compounds of the Present Application

| Cmpd. No. | Structure | AID+ EC$_{50}$ (μM)<br>A = ≤0.1 μM<br>B = ≤1 μM<br>C = >1 μM<br>ND = Not Determined | AID− EC$_{50}$ (μM)<br>A = ≤0.1 μM<br>B = ≤1 μM<br>C = >1 μM<br>ND = Not Determined |
|---|---|---|---|
| 66B | 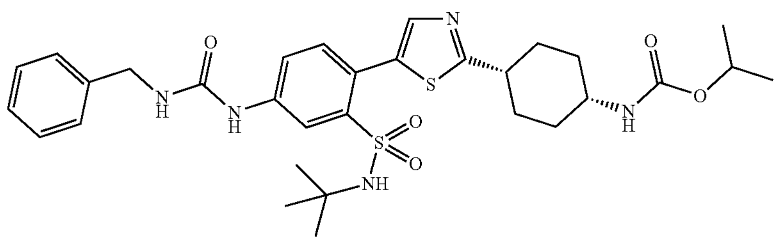 [SMILES: CC(C)OC(=O)N[C@H]1CC[C@@H](c2ncc(-c3ccc(NC(=O)NCc4ccccc4)cc3S(=O)(=O)NC(C)(C)C)s2)CC1] | B | ND |
| 67A | 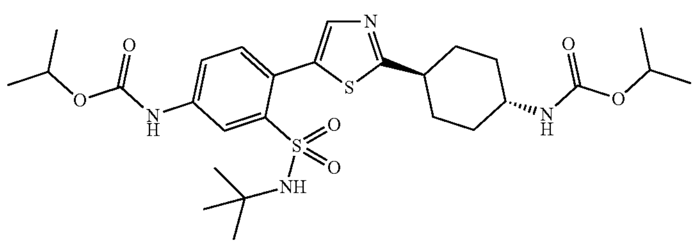 [SMILES: CC(C)OC(=O)Nc1ccc(-c2cnc([C@H]3CC[C@H](NC(=O)OC(C)C)CC3)s2)c(S(=O)(=O)NC(C)(C)C)c1] | B | C |
| 67B | 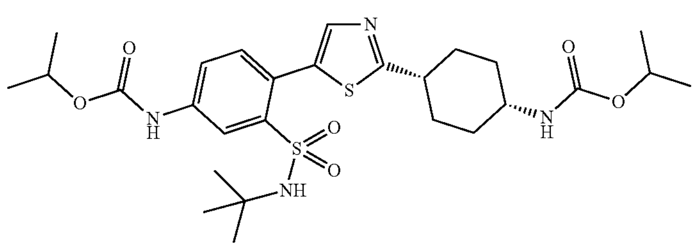 [SMILES: CC(C)OC(=O)Nc1ccc(-c2cnc([C@H]3CC[C@@H](NC(=O)OC(C)C)CC3)s2)c(S(=O)(=O)NC(C)(C)C)c1] | C | ND |
| 68 | 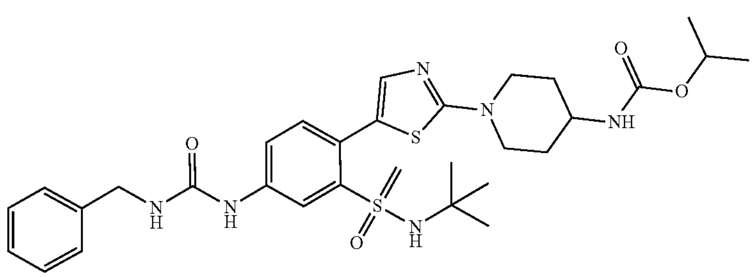 [SMILES: C=S(=O)(NC(C)(C)C)c1cc(NC(=O)NCc2ccccc2)ccc1-c1cnc(N2CCC(NC(=O)OC(C)C)CC2)s1] | B | ND |
| 69 | 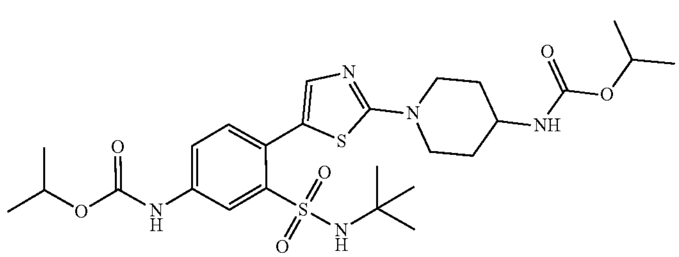 [SMILES: CC(C)OC(=O)Nc1ccc(-c2cnc(N3CCC(NC(=O)OC(C)C)CC3)s2)c(S(=O)(=O)NC(C)(C)C)c1] | C | ND |

TABLE 1-continued

Compounds of the Present Application

| Cmpd. No. | Structure | AID+ EC$_{50}$ (μM)<br>A = ≤0.1 μM<br>B = ≤1 μM<br>C = >1 μM<br>ND = Not Determined | AID− EC$_{50}$ (μM)<br>A = ≤0.1 μM<br>B = ≤1 μM<br>C = >1 μM<br>ND = Not Determined |
|---|---|---|---|
| 70 | 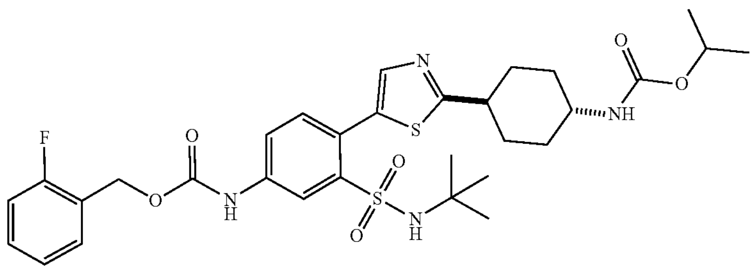 | A | C |
| 71 | 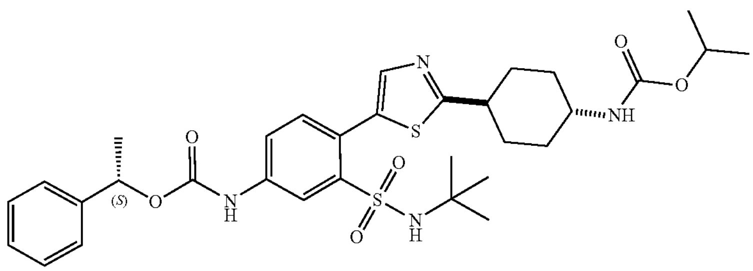 | A | C |
| 72 | 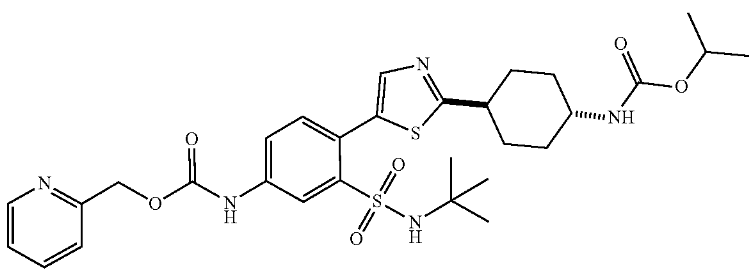 | A | C |
| 73 | 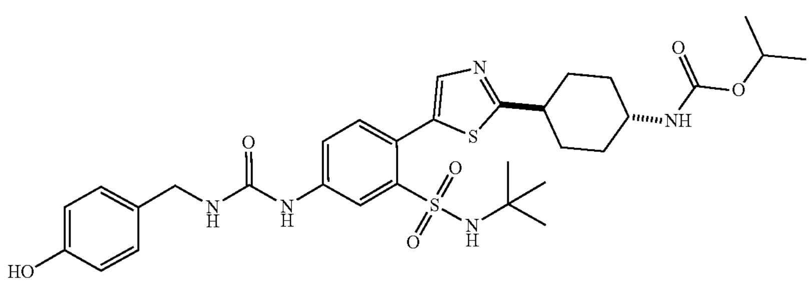 | A | C |
| 74 | 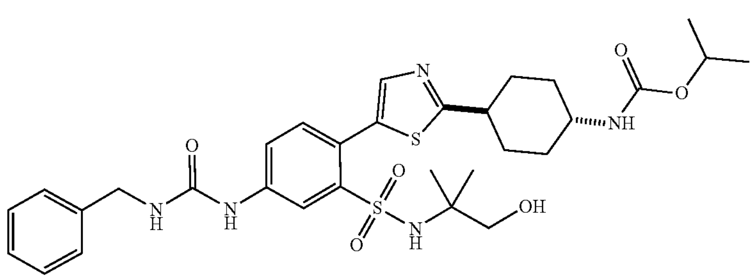 | A | C |

Example 3. Bi-Directional Caco-2 Permeability

Bi-directional Caco-2 permeability was assayed. Caco-2 cells were seeded onto permeable polycarbonate supports and allowed to differentiate for about 3 weeks prior to being used in the assays. The cells were then exposed to the compounds from either the apical or basolateral sides and incubated at 37 C for up to 90 minutes under light agitation. Compound transport was then measured using LC/MS/MS analysis at 30, 60, and 90 minutes.

TABLE 2

Caco-2 Results

| Compound No. | AB Papp (cm/sec × $10^6$) | BA Papp (cm/sec × $10^6$) | BA/AB Ratio | AB Recovery % | BA Recovery % |
|---|---|---|---|---|---|
| 5 | 5.9 | 2.2 | 0.4 | 34.7 | 80.8 |
| 7 | 1.7 | 2.1 | 1.2 | 55.9 | 92 |
| 10 | 1.2 | 1.5 | 1.3 | 59.9 | 87.2 |
| 17 | 2.8 | 2.1 | 0.8 | 47.2 | 81.9 |
| 20 | 9.4 | 10.4 | 1.1 | 44.8 | 96.6 |
| 21 | 3.6 | 10.7 | 3 | 58.6 | 78.3 |
| 22 | 1.1 | 21 | 18.7 | 83.1 | 89 |
| 27 | 0.7 | 0.5 | 0.7 | 92 | 107.1 |
| 28 | 1.9 | 3.3 | 1.7 | 66.9 | 81 |
| 29 | 10.9 | 24.1 | 2.2 | 93.9 | 90.9 |
| 30 | 11.5 | 15.7 | 1.4 | 79.8 | 115.6 |
| 31 | 12.8 | 13.6 | 1.1 | 70.5 | 92.3 |
| 34 | 0.4 | 45.2 | 103.9 | 98.2 | 96.8 |
| 35 | 0.4 | 41 | 99.1 | 98.8 | 107.5 |
| 38 | 17.9 | 22.9 | 1.3 | 73.3 | 82.3 |
| 44 | 3.2 | 4.2 | 1.3 | 36.2 | 69.4 |
| 45 | 7.6 | 10.8 | 1.4 | 73.6 | 84.4 |
| 47 | 8.7 | 12.4 | 1.4 | 65.3 | 80.7 |
| 48 | 23.1 | 16 | 0.7 | 80.1 | 90.3 |
| 50 | 2 | 29.1 | 14.6 | 87.7 | 98.1 |
| 51 | 9.9 | 10.5 | 1.1 | 65 | 85.7 |
| 52 | 7.4 | 10.9 | 1.5 | 64.1 | 91.7 |
| 53 | 9.3 | 9.7 | 1 | 63.1 | 90.9 |
| 55 | 6.5 | 7 | 1.1 | 65.2 | 83.8 |
| 57 | 1.3 | 3.5 | 2.7 | 61.9 | 86.8 |
| 58 | 5.1 | 3.4 | 0.7 | 52.3 | 83.5 |
| 59 | 3.1 | 15 | 4.8 | 61.5 | 91.5 |
| 59A | 3.1 | 9.6 | 3.1 | 55.6 | 85.5 |
| 59B | 4.6 | 9.7 | 2.1 | 56.2 | 82 |
| 60 | 15.6 | 13.3 | 0.9 | 59.8 | 90.8 |
| 60A | 12 | 11.2 | 0.9 | 55.3 | 86 |
| 60B | 11.6 | 13.5 | 1.2 | 51.2 | 84.3 |
| 63 | 10.5 | 26.7 | 2.5 | 83.6 | 90 |
| 64 | 2.2 | 27.4 | 12.5 | 79.7 | 95.9 |
| 66A | 2.9 | 3.9 | 1.4 | 64.9 | 81.2 |
| 67A | 10.5 | 6.9 | 0.7 | 50.7 | 78.6 |

Example 4. Human Liver Microsome Stability

The stability of the claimed compounds was determined in the presences of human liver microsomes. The compounds were incubated with the microsomes at 37° C. for 45 minutes. Samples were analyzed using LC-MS/MS. Data analysis included half-life, clearance rate, and the percentage of hepatic blood flow (% QH) for each of the compounds in the different species. Below are liver microsome assat data of representative compounds, which show that the claimed compounds have superior metabolic stability.

TABLE 3

| Compound No. | Human Liver Microsome Stability | | |
|---|---|---|---|
| | Half Life (min) | Clearance (μg/min/mg) | % QH |
| 29 | 20.5 | 68.0 | 78.8 |
| 31 | 22.4 | 61.9 | 77.3 |

TABLE 3-continued

| Compound No. | Human Liver Microsome Stability | | |
|---|---|---|---|
| | Half Life (min) | Clearance (μg/min/mg) | % QH |
| 66A | 77.6 | 18.2 | 49.6 |
| 67A | >300 | <4.6 | <20.3 |

Example 5. Cell Line Screen

The activity of the claimed compounds was measured in a variety of cell lines with different expression levels of activation induced cytidine deaminase (AICDA). The potency assay was repeated in all of the listed cell lines and the $EC_{50}$ values recorded.

TABLE 4

| Cell Line (Cancer Type) | AICDA Expression | EC$_{50}$ (nM) Cmpd. 29 | EC$_{50}$ (nM) Cmpd. 31 | EC$_{50}$ (nM) Cmpd. 66A | EC$_{50}$ (nM) Cmpd. 67A |
|---|---|---|---|---|---|
| Daudi (Lymphoma) | High | 43 | 20 | 18 | 311 |
| WSU-FSCCL (Lymphoma) | Negative | 67 | <40 | 25 | 344 |
| U-698-M (Lymphoma) | High | 113 | 31 | 88 | 791 |
| CCRF-SB (Leukemia) | High | 1283 | 2164 | 183 | 932 |
| KYSE-70 (Head and Neck) | Low | 4660 | 4701 | 2639 | 2629 |
| SNU-1 (Gastric) | Negative | n.d. | n.d. | 609 | 2927 |
| KG-1 (Leukemia) | Negative | >10000 | 8785 | 3067 | 2995 |
| KYSE-510 (Head and Neck) | Negative | >10000 | >10000 | 4516 | 3403 |
| SNU-5 (Gastric) | Low | n.d. | n.d. | 2941 | 3845 |
| TOV-1120D (Ovary) | Negative | 9172 | n.d. | 2377 | 4924 |
| OV56 (Ovary) | Low | 9086 | n.d. | 5944 | 7228 |
| ARPE19/HPV16 (HPV Immortalized RPE) | Negative | >10000 | >10000 | >10000 | >10000 |
| WI-38 (Normal Human Lung Fibroblast) | Negative | >10000 | >10000 | >10000 | >10000 | n.d. not determined

Example 6. Pharmacokinetic (PK)

PK studies in mice were used to determine the fate of the compounds in a whole organism. Rats were treated with the compounds either orally of via IV at the indicated doses and followed for up to 24 hours. Plasma samples were taken at different time points and analyzed by LC-MS.

TABLE 5

| po @ 80 mg/kg (Formulation: 30% PEG400, 10% Vitamin E TPGS in water) | | Cmpd. 29 | Cmpd. 31 | Cmpd. 66A | Cmpd. 67A |
|---|---|---|---|---|---|
| Rat Female | T$_{1/2}$ (hr) | 4.66 | 4.75 | 2.59 | 11.5 |
| | F (%) @ 5 mg/kg | 8.39 | 2.77 | 3.31 | 86.5 |
| Rat Male | T$_{1/2}$ (hr) | 3.97 | 3.79 | 1.86 | 6.46 |
| | F (%) @ 5 mg/kg | 3.69 | 1.49 | 2.55 | 46.9 |

Example 7. Combination Treatment of Compound 67A with PARP Inhibitors

Genomic instability is a driver of tumorigenesis and cancer progression. Loss of tumor suppressors or activation of oncogenes can induce DNA damage stress, promoting genomic instability and creating dependencies upon key DNA repair pathways. These dependencies can be targeted therapeutically to induce synthetic lethality. Without being bound by any theory, RAD51 inhibitor, Compound 67A, which is selectively active in Activation Induced Cytidine Deaminase (AID) expressing cells. In cancer cells, AID causes significant genotoxic stress through DNA replication fork collapse which creates a dependency upon the homologous recombination repair factor, RAD51, for survival. Compound 67A acts by destabilizing RAD51 focus formation, leading to it premature nuclear export and subsequent degradation. PARP inhibitors use another synthetic lethal mechanism, in which PARP1, a protein important for repairing single strand breaks, is inhibited in BRCA1/2 deficient cancers. A main resistance mechanism to PARP inhibitors is the overexpression of RAD51; therefore, Compound 67A could act as a sensitizer to PARP inhibitors.

A matrix study was performed with Compound 67A (concentration range of 20 nM to 5 µM) and 5 different PARP inhibitors including olaparib (20 nM to 2.5 µM), niraparib (20 nM to 2.5 µM), veliparib (2.5 µM to 50 µM), rucaparib (156 nm to 10 µM), and talazoparib (9 nM to 0.625 µM). The combination matrix was tested in 3 cell lines of varying AID expression: ARPE19/HPV16 (HPV immortalized normal epithelial cell line), KYSE-70 (head and neck cancer cell line) and Daudi (Burkitt's Lymphoma cell line). PARP indicated cells lines were also tested including HCC1143 and BT20, both of which are derived from triple negative breast cancers and were selected for their varying responsiveness to olaparib. Both the Loewe Additivity model and the Bliss Independence model were used to determine drug interaction (synergistic, independent, or antagonistic). In general, synergy with the PARP inhibitors was observed in the tumor derived cell lines. Only with olaparib was synergy observed in the non-tumor derived cell line ARPE19/HPV16. Greater synergistic activity with Compound 67A with increasing PARP trapping efficiency was observed. Veliparib, as a pure catalytic inhibitor of PARP, deviated from that trend and showed similar levels of synergy as that observed with niraparib. These data suggest that Compound 67A may be active as a combinatorial therapy with PARP inhibitors. This Example shows there is significant synergy in combining RAD51 and PARP inhibition as a cancer treatment strategy.

Bliss Independence model was used and calculated in Excel. The model assumes that the drugs act with probabilistic independence.

Bliss: $y_{exp} = y_A + y_B - y_A y_B$

This expected value was generated by examining single-agent effects and then tested against the observed value using a two-tailed Welch's T-Test. For visualization purposes, the values generated from this test were transformed to a "Synergy Score" by doing the computation:

$$\text{Synergy Score} = \frac{-\log(p)}{\log(0.05)} \times \frac{t}{|t|}$$

Loewe Additivity model was used and calculated by the "Synergyfinder" R package.

$$\frac{x_1}{f_1^{-1}(y_{Loewe})} + \frac{x_2}{f_2^{-1}(y_{Loewe})} = 1$$

The graphs generated describe the difference between the expected value generated by the additivity model and the observed value generated by the experiment. If the effect determined by the additivity model<the effect observed the space is colored red, if the effect determined by the additivity mode>the effect observed then the space is colored green. The saturation of the color is proportional to the magnitude of the difference between these two values.

TABLE 6

Results from Combination Compound 67A + PARP Inhibitor Treatment in Cells

| Drug/ Combination | Cell Conditions Tested | Conclusion |
|---|---|---|
| Compound 67A/ olaparib | AICDA Expression Range (Low, Med, High) | All cells tested showed strong synergy with olaparib regardless of AICDA expression |
| Compound 67A/ olaparib | BRCA-Status (wt, —/—) | In both conditions combination treatment showed concentration-dependent synergy and antagonism. |
| Compound/ 67A veliparib | AICDA Expression Range (Low, Med, High) | The combination was strongly synergistic in AICDA-low and AICDA-high cells. |
| Compound 67A/ veliparib | BRCA-Status (wt, —/—) | In both conditions combination treatment showed concentration-dependent synergy and antagonism. |
| Compound 67A/ rucaparib | AICDA Expression Range (Low, Med, High) | The combination was synergistic only in the AICDA-high cells at low concentrations |
| Compound 67A/ talazoparib | AICDA Expression Range (Low, Med, High) | The combination was synergistic in AICDA-high cells and in AICDA low cells. |

TABLE 6-continued

Results from Combination Compound 67A + PARP Inhibitor Treatment in Cells

| Drug/ Combination | Cell Conditions Tested | Conclusion |
|---|---|---|
| Compound 67A/ niraparib | AICDA Expression Range (Low, Med, High) | The combination was strongly synergistic in AICDA-low and AICDA-high cells. |

Example 8. Treatment with Compound 67A in Combination with Olaparib

Immunodeficient mice were subcutaneously engrafted in the rear flank with the tumor cells. The tumors were allowed to grow to a size of about 100 to about 200 mm$^3$ prior to being randomized and grouped into treatment arms. For models HBCx1 through HBCx1 the four treatment arms were vehicle, Compound 67A at 80 mg/kg QD, olaparib at 100 mg/kg QD, and Compound 67A+Olaparib at 80 mg/kg QD and 100 mg/kg QD, respectively. For models J000101173 through TM00091 the treatment arms were vehicle, Compound 67A at 40 mg/kg QD, olaparib at 50 mg/kg QD, and Compound 67A+Olaparib at 40 mg/kg QD and 50 mg/kg QD, respectively. The tumors were measured either once weekly or twice weekly.

Percent Tumor Growth Inhibition (% TGI) was calculated by taking the mean volume of each of the treatment arms, and comparing the treatment arms to the vehicle arms using the following equation $$\left(1 - \frac{\text{treatment arm mean volume}}{\text{vehicle mean volume}}\right) * 100 = TGI\ \%.$$

Results for each treatment arm are present in Table 7.

TABLE 7

Cellular Growth Inhibition by the Combination of Compound 67A and Olaparib

| Model | % TGI 67A | % TGI Olaparib | % TGI Combo | HRD Status | RAD51 Exp. | BRCA Status | PALB2 Status |
|---|---|---|---|---|---|---|---|
| HBCx11 | 23.39 | 60.95 | 88.42 | Positive | High | BRCA1 Mut | WT |
| HBCx17 | −51.13 | 122 | 124.2 | Positive | High | BRCA2 Mut | WT |
| HBCx23 | NA | 84.48 | 78.79 | Positive | High | BRCA1 Meth | WT |
| HBCx27 | 13.14 | 7.819 | 51.50 | Negative | High | WT | WT |
| T298 | NA | 107 | 101 | Positive | Low | WT | Mut |
| HBCx16 | −22.45 | −25.61 | −22 | Positive | High | BRCA1 Meth | WT |
| HBCx12B | −3.27 | 42.56 | 57.26 | Positive | High | BRCA1 Meth | WT |
| HBCx1 | 28.75 | 51.07 | 114.9 | Positive | High | WT | WT |
| J000101173 | 19.87 | 4.71 | −27.7 | Positive | Low | WT | WT |
| J000100675 | 36.69 | −17 | 48.07 | Negative | Low | WT | WT |
| TM000113 | 7.24 | 2.37 | 45.74 | Negative | Low | WT | WT |
| TM01079 | 26.73 | 68.7 | 99.69 | Positive | Low | BRCA1 Meth | WT |
| TM00090 | 51.82 | 86.05 | 109.8 | Positive | Low | BRCA1 Meth; BRCA2 Mut | WT |
| TM00096 | −25.4 | −1.94 | −33.2 | Positive | Low | WT | WT |
| TM00091 | 27 | 21.26 | 61.79 | Positive | High | BRCA1 Mut | WT |

EQUIVALENTS

The details of one or more embodiments of the invention are set forth in the accompanying description above. Although any methods and materials similar or equivalent to those described herein can be used in the practice or testing of the present disclosure, the preferred methods and materials are now described. Other features, objects, and advantages of the disclosure will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this disclosure belongs. All patents and publications cited in this specification are incorporated by reference.

The foregoing description has been presented only for the purposes of illustration and is not intended to limit the invention to the precise form disclosed, but by the claims appended hereto.

The invention claimed is:

1. A method of treating a cancer selected from a hematological cancer and a solid tumor, comprising administering to a subject in need thereof a therapeutically effective amount of a compound of the following structure:

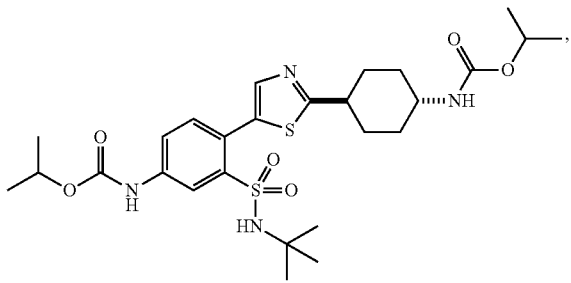

or a pharmaceutically acceptable salt thereof, and
a therapeutically effective amount of a PARP inhibitor selected from the group consisting of olaparib, veliparib, and niraparib, or a pharmaceutically acceptable salt thereof.

2. The method of claim 1, wherein the PARP inhibitor is olaparib.

3. The method of claim 1, wherein the cancer is a hematological cancer.

4. The method of claim 3, wherein the hematological cancer is selected from lymphoma, leukemia, and a plasma cell neoplasm.

5. The method of claim 4, wherein the lymphoma is a B-cell lymphoma.

6. The method of claim 5, wherein the B-cell lymphoma is diffuse large B-cell lymphoma.

7. The method of claim 4, wherein the lymphoma is mantle cell lymphoma.

8. The method of claim 4, wherein the lymphoma is Burkitt's Lymphoma.

9. The method of claim 1, wherein the cancer is a solid tumor.

10. The method of claim 9, wherein the solid tumor is selected from breast cancer, ovarian cancer, pancreatic cancer, prostate cancer, fallopian tube cancer, peritoneal cancer, and lung cancer.

11. The method of claim 1, wherein the PARP inhibitor is veliparib.

12. The method of claim 1, wherein the PARP inhibitor is niraparib.

* * * * *